US008916380B2

(12) United States Patent
Lim et al.

(10) Patent No.: US 8,916,380 B2
(45) Date of Patent: Dec. 23, 2014

(54) EMBRYONIC STEM CELL-LIKE CELLS

(75) Inventors: Jeong Mook Lim, Seoul (KR); Jae Yong Han, Seoul (KR); Hee Bal Kim, Seoul (KR); Seoung Tae Lee, Anyang-si (KR); Eun Ju Lee, Seoul (KR); Seung Pyo Gong, Busan (KR)

(73) Assignee: Seoul National University Industry Foundation, Seoul (KR)

( * ) Notice: Subject to any disclaimer, the term of this patent is extended or adjusted under 35 U.S.C. 154(b) by 748 days.

(21) Appl. No.: 12/377,493

(22) PCT Filed: Dec. 20, 2006

(86) PCT No.: PCT/KR2006/005593

§ 371 (c)(1), (2), (4) Date: Feb. 13, 2009

(87) PCT Pub. No.: WO2008/020666

PCT Pub. Date: Feb. 21, 2008

(65) Prior Publication Data

US 2010/0227396 A1 Sep. 9, 2010

(30) Foreign Application Priority Data

Aug. 14, 2006 (KR) ................ PCT/KR2006/003187

(51) Int. Cl.

| | |
|---|---|
| ***C12N 5/07*** | (2010.01) |
| ***C12N 5/02*** | (2006.01) |
| ***C12N 5/10*** | (2006.01) |
| ***C12N 5/074*** | (2010.01) |

(52) U.S. Cl.

CPC .......... *C12N 5/0696* (2013.01); *C12N 2502/03* (2013.01); *C12N 2501/235* (2013.01); *C12N 2502/21* (2013.01); *C12N 2502/04* (2013.01)

USPC ........................... 435/347; 435/325; 435/352

(58) Field of Classification Search

CPC .................................................... C12N 5/0696

USPC ........................................................ 435/347

See application file for complete search history.

(56) References Cited

FOREIGN PATENT DOCUMENTS

WO 2004/092357 A1 10/2004

OTHER PUBLICATIONS

Rodolfa and Eggan, 2006, Cell, 126:652-655.*
Takahashi 2006, Cell, 126:663-676.*
Ying et al. (2003) Cell 115:281-292.*
Sato et al. (2004) Nat. Med. 10:55-63.*
Humphrey et al. (2004) Stem Cells 22: 522-530.*
Kanatsu-Shinohara, M., et al., "Generation of Pluripotent Stem Cells from Neonatal Mouse Testis," Cell, 119: Dec. 29, 2004, 1001-1012.
Kanatsu-Shinohara, M., et al., "Long-Term Proliferation in Culture and Germ Line Transmission of Mouse Male Germline Stem Cells," Biology of Reproduction, 69: Apr. 16, 2003, 612-612.
Hackney, J.A., et al., "A molecular profile of a hematopoietic stem cell niche," Proceedings of the National Academy of Science of USA, 99:20, Oct. 1, 2002, 13061-66.
Nagano, M., et al., "Maintenance of Mouse Male Germ Line Stem Cells In Vitro," Biology of Reproduction, 68: 2003, 2207-14.

* cited by examiner

*Primary Examiner* — Valarie Bertoglio
(74) *Attorney, Agent, or Firm* — Sughrue Mion, PLLC

(57) ABSTRACT

Disclosed is a method for preparing an embryonic stem cell (ESC)-like cell, which includes the steps of: (a) obtaining a first cell population from a mammalian tissue or body fluid, wherein the first cell population comprises adult stem cells; (b) obtaining a second somatic cell population from a mammalian tissue, wherein the mammalian tissue is different from the mammalian tissue in step (a) and the second cell population is different from the first cell population; (c) coculturing the first cell population and the second cell population in a medium for a period of time sufficient to form a colony from either the first cell population or the second cell population; and (d) subculturing a cell from the colony in a medium for a period time sufficient to prepare the ESC-like cell.

4 Claims, 26 Drawing Sheets

EMBRYONIC STEM CELL-LIKE CELLS

This is a National Stage application under 35 U.S.C. §371 of PCT/KR2006/005593 filed on Dec. 20, 2006, which claims priority from PCT/KR2006/003187 filed on Aug. 14, 2006, all of which are incorporated herein by reference.

BACKGROUND OF THE INVENTION

1. Field of the Invention

The present invention relates to a method for preparing an embryonic stem cell-like cell having pluripotency, and a mammalian tissue-derived embryonic stem cell-like cell.

2. Description of the Related Art

Although patient-specific somatic cell nuclear transfer (SCNT) is an absolute method for developing an immune reaction-free cell therapy, several methods have been suggested for replacing SCNT to avoid human cloning[1-10]. However, each alternative suggested has various limitations for developing as the patient-specific therapy. Oocyte parthenogenesis is one possible alternative. Embryonic stem (ES) cells have been derived from the parthenogenesis of ovulated oocytes in primates (Vrana, K. E. et al. Nonhuman primate parthenogenetic stem cells. *Proc. Natl. Acad. Sci. USA* 100, 11911-11916 (2003)) and recently in human (Brevini et al., ESHRE annual meeting in 2006). We have established autologous ES cells via the parthenogenesis of immature oocytes collected from preantral follicles (unpublished data, PCT/KR2006/001891). However, these methods do not eliminate completely the need for human cloning.

Throughout this application, various publications and patents are referenced and citations are provided in parentheses. The disclosures of these publications and patents in their entities are hereby incorporated by references into this application in order to more fully describe this invention and the state of the art to which this invention pertains.

SUMMARY OF THE INVENTION

Under such circumstances, the present inventors have made intensive researches to meet long-felt need in the art, and as a result, developed a novel method for successfully preparing an embryonic stem cell (ESC)-like cell having pluripotency without embryos and gametes.

Accordingly, it is an object of this invention to provide a method for preparing an embryonic stem cell (ESC)-like cell.

It is another object of this invention to provide a mammalian tissue or body fluid-derived embryonic stem cell (ESC)-like cell.

It is still another object of this invention to provide a culture medium for dedifferentiating a mammalian cell having no pluripotency into an embryonic stem cell (ESC)-like cell having pluripotency.

It is further object of this invention to provide a culture medium for producing an embryonic stem cell (ESC)-like cell from a mammalian tissue cell.

Other objects and advantages of the present invention will become apparent from the detailed description to follow and together with the appended claims and drawings.

BRIEF DESCRIPTION OF THE DRAWINGS

FIG. **5*a*-5*b*. Characterization of embryonic stem cell (ESC)-like cells derived from the coculturing of F1 (B6D2F1; C57BL/6×DBA2) embryonic fibroblasts and adult F1 (B6CBAF1; C57BL/6×CBA/Ca) ovarian cells.

FIG. 9*a*, EBs observed on day 4 of culture in LIF-free medium. Immunocytochemistry of EBs was used to detect three germ layer-specific differentiation using the specific markers of S-100 (b; ectodermal), nestin (c; ectodermal), smooth muscle actin (d; mesodermal), Desmin (e; mesodermal), α-fetoprotein (f; endodermal), and Troma-1 (g; endodermal-specific). FIG. 9*b*, Real-time PCR analysis of the EBs derived from E14 ES cells (h) or the ESC-like cells (i) was performed to detect the expression of stem cell-specific or three germ layer-specific genes. The stem cell-specific Oct-4 and Nanog genes or the three germ layer-specific Ncam (ectoderm), Nestin (ectoderm), Smooth muscle actin (mesoderm), Desmin (mesoderm), α-fetoprotein (endoderm), and Troma1 (endoderm) genes were used and real-time PCR analysis was performed on day 0 (d0; ES or ESC-like cells), day 7 (d7; using EBs), and day 21 (d21; using EBs). Regardless of EB origin, the levels of Oct-4 and Nanog expression decrease with increasing time of EB culture. In contrast, the expression levels of Ncam, Nestin, Smooth muscle actin, Desmin, α-fetoprotein, and Troma1 are higher in EBs maintained for 21 days than in either ESC-like cells or EB maintained for 7 days. E14 ES cells and their derived EBs (h); ESC-like cells and their derived EBs (i). N/D, not detected. Scale bar=100 μm.

FIG. 2*a*, Expression of Oct-4, Nanog, Rex-1, and Cripto genes in the brain, heart, lung, liver, stomach, kidney, ovary, small intestine, skin, and spleen retrieved from 8-week-old, female mice. Oct-4 expression is detected in the ovary, small intestine, and spleen, while all the tissues examined express the Nanog gene. Most of the organs, with the exceptions of the stomach and skin express the Cripto gene. FIG. 2*b*, Expression of Oct-4, Nanog, Rex-1, Cripto, Dnmt3b, Tert, and Lif Rc genes in individual ovaries retrieved from 8-week-old female mice. E14 embryonic stem cells (ESC) were used as the control cells. All the genes tested are expressed in the E14 ESCs. +, Reverse transcription using isolated total RNA; −, non-reverse transcription using isolated total RNA.

DETAILED DESCRIPTION OF THIS INVENTION

Figure 1:
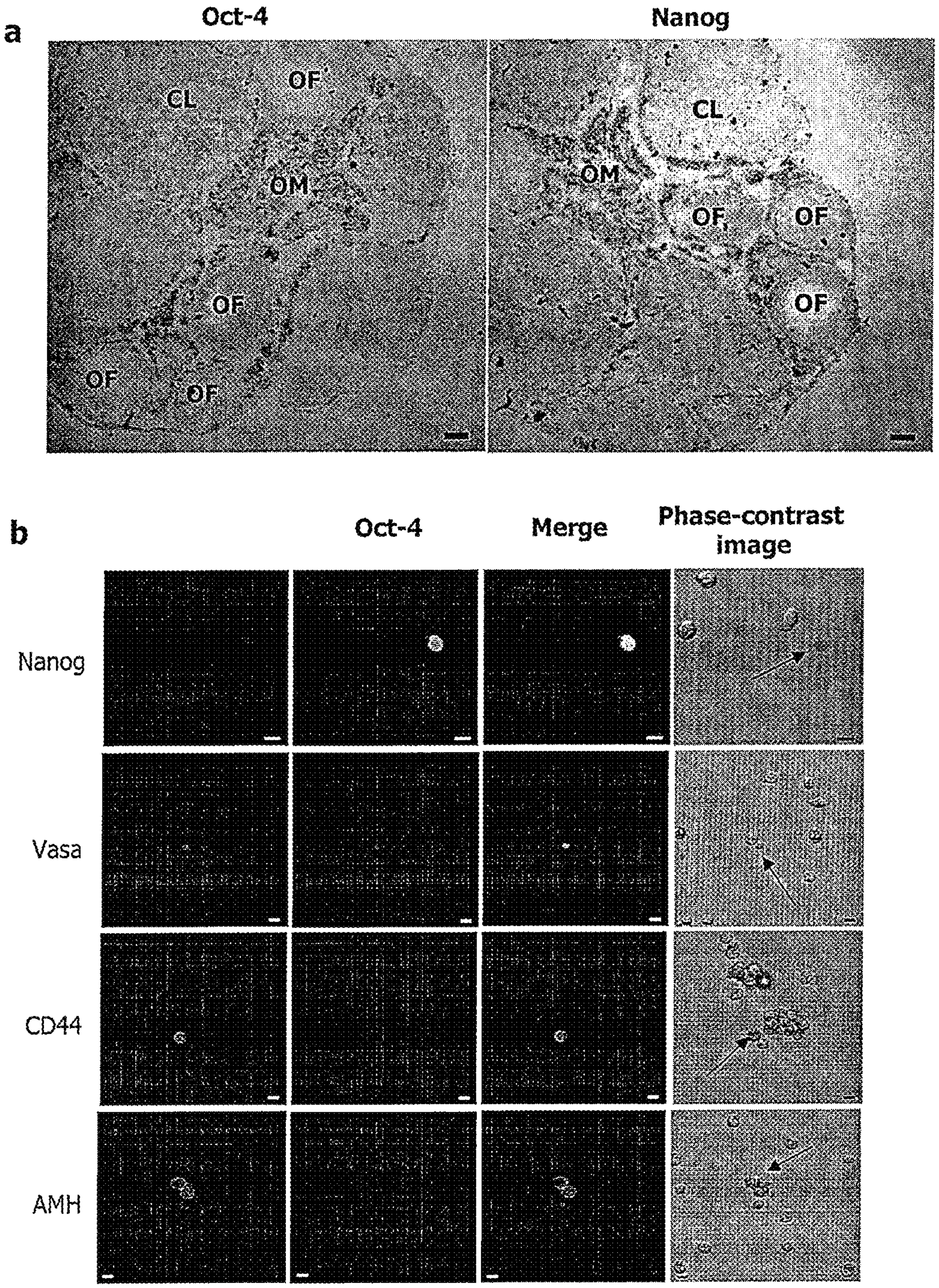
FIG. 1. In situ hybridization of ovarian tissue for the detection of Oct-4 and Nanog mRNA expression, and double immunostaining of Oct-4-positive ovarian tissue-dissociated cells for the Oct-4, Vasa, AMH, and CD44 markers of stem cells, germ cells, follicular cells, and mesenchymal stem cells, respectively. (a) In situ hybridization of ovaries retrieved from an 8-week-old, adult mouse (B6CBAF1; C57BL/6×CBA/Ca) with Oct-4- and Nanog-specific mRNA probes. Oct-4 and Nanog mRNA expression is evident in the numerous ovarian medullae near the blood vessel (OM). The theca cell region of different stage ovarian follicles (OF) also show the mRNA expression. (CL) corpus luteum. Scale bar=100 μm. (b) The ovarian tissue cells immediately after dissociation were double-immunostained. The Oct-4-positive cells are concomitantly immunostained with anti-Nanog, anti-Vasa or anti-CD44 antibodies, while they are not positive for AMH staining (confocal microscope image). Phase-contrast image of Oct-4-positive plus Nanog-, Vasa- or CD44-positive cells and of AMH-positive, but Oct-4 negative cell (arrows). Scale bar=10 μm.

In one aspect of this invention, there is provided a method for preparing an embryonic stem cell (ESC)-like cell, which comprises the steps of: (a) obtaining a first cell population from a mammalian tissue or body fluid, wherein the first cell population comprises adult stem cells; (b) obtaining a second somatic cell population from a mammalian tissue, wherein the mammalian tissue is different from the mammalian tissue in step (a) and the second cell population is different from the first cell population; (c) coculturing the first cell population and the second cell population in a medium for a period of time sufficient to form a colony from either the first cell population or the second cell population; and (d) subculturing a cell from the colony in a medium for a period time sufficient to prepare the ESC-like cell.

The present invention is directed to a novel approach for establishing embryonic stem cell (ESC)-like cells having pluripotency from mammalian tissue cells without undertaking SCNT and without using embryos and even gametes. Therefore, the present method is also expressed as methods for preparing ESC-like cells without using embryo. The present invention makes it possible and practicable to establish an immune reaction-free, patient-specific cell therapy without human cloning. To our best knowledge, the present invention provides for the first time the generation of ESC-like cells from mammalian cells, e.g., differentiated somatic cells, with no help of gamete manipulation. According to the present method, two cell populations can be induced to form ESC-like cells by adjusting culture conditions and/or environment.

The term "embryonic stem cell (ESC)-like cell" is used herein to refer to a cell having pluripotency that is induced by the present method, to exhibit a property of an embryonic stem cell, including, but not limited to, proliferation without transformation, continuous proliferation, self-renewal and capacity of developing into any cell derived from the three main germ cell layers, and the like. That is, the ESC-like cells induced by the present invention acquire an embryonic-like stage.

The present invention will be described in more detail as follows:

Preparation of First Cell Population Containing Adult Stem Cells

The first cell population containing adult stem cells may be obtained by various conventional methods from a multitude of sources. The source for the first cell population containing adult stem cells may comprise any mammalian tissue or fluid previously known to contain adult stem cells.

The term "adult stem cell" used herein refers to an undifferentiated (unspecialized) cell that occurs in a differentiated (specialized) tissue, renews itself, and becomes specialized to yield all of the specialized cell types of the tissue from which it originated.

According to a preferred embodiment, the mammalian tissue or body fluid as sources for the adult stem cells-containing first cell population is derived from ovary, testis, bone marrow, peripheral blood, umbilical cord blood, amniotic fluid, brain, blood vessel, skeletal muscle, epithelia of skin or gastrointestinal tract, cornea, dental pulp of tooth, retina, liver, spleen or pancreas. For example, stem cells derived from brain have been isolated in the subventricular zone, ventricular zone and hippocampus of the CNS (central nervous system). Bone marrow has been reported to have hematopoietic stem cells and mesenchymal (stromal) stem cells.

More preferably, the mammalian tissue or body fluid as sources for the adult stem cells-containing first cell population is ovary, liver, stomach, skin or spleen, most preferably, ovary.

The first cell population containing adult stem cells for preparing ESC-like cells may be obtained by various methods known in the art. For example, cells may be obtained by disassociation of tissue by mechanical (e.g., chopping and mincing) or enzymatic means (e.g., trypsinization) to obtain a cell suspension followed by culturing the cells until a confluent monolayer is obtained. The cells may then be harvested and prepared for cryopreservation. The isolation of somatic cells, for example, ovarian cell, is described in Examples.

The first cell population containing adult stem cells may further contain any type of cells that contains a genome or genetic material (e.g., nucleic acid), such as a somatic cell and germ cell. The term "somatic cell" as used herein refers to a differentiated cell. The cell may be a somatic cell or a cell that is committed to a somatic cell lineage. Preferably, the cell useful in this invention is a differentiated somatic cell.

The first cell population may be obtained from tissues at any development stage, e.g., post-puberty mammalian tissue, pre-embryonic, embryonic, neonatal or fetal tissue at any time after fertilization. According to a preferred embodiment, the first cell population is obtained from a mammalian tissue or body fluid at any development stage after birth, more preferably, from a post-puberty mammalian tissue or body fluid. The term "post-puberty mammalian" is intended to refer to a mammal after a puberty stage in development of mammals. That is, the term "post-puberty mammalian" has the identical meaning to the term "adult mammalian" generally used in this art. There is no intended distinction between the terms "post-puberty mammalian" and "adult mammalian", and these terms will be used interchangeably. For example, the average age at puberty for mice, cow, pig and human is approximately, 3 to 4 weeks, 10 to 14 months, 2 to 3 months and 10 to 15 years, respectively.

Where cells from the ovary, i.e., ovarian cells are used, it is preferred that they are substantially freed from ovarian stromal cells, oocytes, and preantral and antral follicles. The removal of oocytes, and preantral and antral follicles from ovarian cell preparations may be carried out using a 40-μm cell strainer. Ovarian cells containing adult stem cells used in this invention may contain adult somatic cells, mesenchymal stem cells, primordial follicle and/or ovarian stem cells.

The first cell population provides the second cell population with microenvironment (a niche) suitable in the transformation (dedifferentiation) of cells into ESC-like cells. Without wishing to be bound by theory, it is believed that the niche may secrete and/or provide the factors required to induce dedifferentiation. The term used herein "niche" refers to components (cells and/or substances) composed of tissues or organs (e.g., ovary) supporting the development and proliferation of tissue cells such as stem cells and other somatic cells. In the cases of using ovarian cells, the ovarian niche is provided.

In contrast, under suitable conditions and environment, the first cell population itself is dedifferentiated to ESC-like cells, rather than providing a niche for the dedifferentiation of the second cell population.

According to a preferred embodiment, the first cell population is a heterogeneous cell population comprising at least two cell types. For example, where the first cell population is derived from the ovary, it may comprise mesenchymal stem cells as well as adult somatic cells, primordial follicle and/or ovarian stem cells.

According to a preferred embodiment, the first cell population used in this invention is originated from human, bovine, sheep, ovine, pig, horse, rabbit, goat, mouse, hamster or rat, more preferably, human, mouse or rat.

The genome of the first cell population used in this invention may be the naturally occurring genome, for example, or the genome may be genetically altered to comprise a transgenic sequence. Preferably, the first cell population used in this invention has a naturally occurring genome, especially, for cell transplantation therapy.

Preparation of Second Somatic Cell Population

It is necessary in the present invention that the type of the second somatic cell population is different from that of the first cell population.

The second somatic cell population may be obtained by various methods known in the art. For example, cells may be obtained by disassociation of tissue by mechanical (e.g., chopping and mincing) or enzymatic means (e.g., trypsinization) to obtain a cell suspension followed by culturing the cells until a confluent monolayer is obtained. The cells may then be harvested and prepared for cryopreservation. The isolation of somatic cells, for example, fibroblasts, is described in Examples.

The cells may be any type of somatic cells that contains a genome or genetic material (e.g., nucleic acid). The term "somatic cell" as used herein refers to a differentiated cell. The cell may be a somatic cell or a cell that is committed to a somatic cell lineage. Preferably, the cell useful in this invention is a differentiated somatic cell. The somatic cell may be originated from a mammalian animal or from a cell and/or tissue culture system. If taken from a mammalian animal, the animal may be at any stage of development, for example, an embryo, a fetus or an adult. Additionally, the present invention may utilize embryonic somatic cells.

Suitable somatic cells include fibroblasts (e.g., primary fibroblasts), epithelial cells, muscle cells, cumulous cells, neural cells, and mammary cells. Other suitable cells include hepatocytes and pancreatic islets. Preferably, the second cell population includes fibroblasts and epithelial cells, most preferably fibroblasts.

According to a preferred embodiment, the cell used in this invention is originated from human, bovine, sheep, ovine, pig, horse, rabbit, goat, mouse, hamster or rat, more preferably, human, mouse or rat.

The genome of the somatic cell used in this invention may be the naturally occurring genome, for example, or the genome may be genetically altered to comprise a transgenic sequence. Preferably, the somatic cell used in this invention has a naturally occurring genome, especially, for cell transplantation therapy. It is preferable that the cell used in this invention is a somatic cell having a diploid karyotype.

According to a preferred embodiment, mitotically inactive cells are used as a cell source for the second cell population. Mitotically inactive cells may be readily prepared for arresting cell cycle by various methods known to one of skill in the art. For example, mitotically inactive cells may be produced by exposure to gamma radiation (e.g., 4000 Rads of gamma radiation) or treatment with mitomycin C.

According to a preferred embodiment, the second somatic cell population has adherent characteristics to culture plates. Such adherent potential permits the second somatic cell population to support the growth of the first cell population. According to a preferred embodiment, the second somatic cell population is a homogenous population substantially comprising one somatic cell type.

The second somatic cell population is dedifferentiated to ESC-like cells with help of the first cell population.

In contrast, under suitable conditions and environment, the second somatic cell population provides environments for the dedifferentiation of the first cell population, rather than dedifferentiating itself to ESC-like cells. In such case, the second somatic cell population may serve as feeder cells.

Coculturing for Forming Colonies Comprising Esc-Like Cells

Two types of cells prepared above, especially, the first and second cell populations, are then cocultured in a medium for a period of time sufficient to form colonies comprising ESC-Like cells having pluripotency.

Preferably, the medium comprises a factor for inhibiting the cell differentiation. The differentiation inhibitory factor includes leukemia inhibitory factor and nm23-H2/nucleoside diphosphate kinase (NDPK)-B. Most preferably, the medium for coculturing comprises leukemia inhibitory factor.

Without wishing to be bound by theory, it is believed that the first cell population or the second somatic cell population and leukemia inhibitory factor, especially, a high dose of leukemia inhibitory factor provide the cells with microenvironment (or niche) suitable in the transformation (dedifferentiation) of cells into pluripotent ESC-like cells. Without wishing to be bound by theory, it is believed that the microenvironment (or niche) may trigger cell-to cell interaction and secrete the factors for acquiring pluripotency.

According to a preferred embodiment, the coculturing step is carried out in the presence of higher concentrations of leukemia inhibitory factor (LIF). The term "higher concentration" used herein with reference to LIF means at least 3,000 units/ml, preferably at least 4,000 units/ml, more preferably at least 5,000 units/ml, still more preferably, 4,000-6000 units/ml of LIF, most preferably, about 5000 units/ml of LIF. According to a more preferred embodiment, the culturing in step (c) is carried out in the presence of at least 3,000 units/ml of LIF, still more preferably at least 4,000 units/ml, still yet more preferably at least 4,000-6,000 units/ml, and most preferably about 5,000 units/ml of LIF. The relatively high concentration of LIF is very advantageous for the production of pluripotent stem cells with higher yield.

A medium useful in this step includes any conventional medium for obtaining mammalian ES cells known in the art. For example, the medium includes Dulbecco's modified Eagle's medium (DMEM), knock DMEM, DMEM containing fetal bovine serum (FBS), DMEM containing serum replacement, Chatot, Ziomek and Bavister (CZB) medium, Ham's F-10 containing fetal calf serum (FCS), Tyrodes-albumin-lactate-pyruvate (TALP), Dulbecco's phosphate buffered saline (PBS), and Eagle's and Whitten's media. Preferably, the culture medium is DMEM containing LIF (leukemia inhibitory factor) supplemented with β-mercaptoethanol, nonessential amino acids, L-glutamine, antibiotics (preferably, penicillin and streptomycin) and/or FBS (fetal bovine serum). The detailed description of media is found in R. Ian Freshney, *Culture of Animal Cells, A Manual of Basic Technique*, Alan R. Liss, Inc., New York, WO 97/47734 and WO 98/30679, the teachings of which are incorporated herein by reference in their entities.

The period of time for forming colonies is not particularly restricted, preferably in the range of 4-9 days, more preferably 6-8 days, most preferably about 7 days.

The colony can be derived from either the first cell population or the second somatic cell population. Without wishing to be bound by theory, the determination is based on the genetic background, environmental susceptibility and/or type of cells.

As exemplified in Examples, cells to be dedifferentiated are determined depending on genetic background of cells. Specifically, where ovarian cells as the first cell population are obtained from B6CBAF1 mice (produced by mating C57BL/6 mice with CBA/Ca mice) and fibroblasts as the second somatic cell population are obtained from B6D2F1 mice (produced by mating C57BL/6 mice with DBA2 mice), the second somatic cell population is dedifferentiated to ESC-like cells. Unlikely, where ovarian cells as the first cell population are obtained from B6D2F1 mice and fibroblasts as the second somatic cell population are obtained from ICR mice, the first cell population is dedifferentiated to ESC-like cells. These findings demonstrate that the genetic background of cells used in coculturing with two cell types determines cells to be dedifferentiated to ESC-like cells. In Examples, cells originated from B6D2F1 mice are dedifferentiated to ESC-like cells.

The present inventors also examined characteristics of cells from B6D2F1 mice and found that stress-defense genes (e.g., Hspa9a, Bmi1, Hspa1b, Pdha2 and Txrnd3) are expressed in a relatively low level and reactive oxygen species are generated in a relatively high level (data not shown). That is, cells originated B6D2F1 mice exhibit high environmental susceptibility. On the basis of these analysis results, it could be recognized that the environmental susceptibility of cells used in coculturing with two cell types determines cells to be dedifferentiated into ESC-like cells. Among two type cells in the coculturing system, cells having higher environmental susceptibility are very likely to be dedifferentiated into ESC-like cells.

Subculturing Cells Forming Colonies to Prepare ESC-Like Cells

For preparing ESC-like cells, colony-forming cells are subcultured in a medium for a period of time sufficient to prepare the ESC-like cell.

According to a preferred embodiment, the subculturing step is carried out in the presence of relatively low concentrations of leukemia inhibitory factor (LIF). More preferably, the subculture is carried out in the presence of no more than 2,000 units/ml of LIF, still more preferably 800-1,200 units/ml, most preferably 1,000 units/ml of LIF.

Detailed descriptions of medium and feeder cell layers for the subculturing step follow those for the culturing in step (c) discussed hereinabove.

ESC-like cells prepared by this invention may be maintained for more than 3 months with 25 passages. Therefore, where the subculturing is performed without substantially undergoing changes (e.g., genetically or biologically) for a longer period of time, the present invention is also expressed as a method for preparing an ESC-like cell line having pluripotency.

According to a preferred embodiment, where the ESC-like cell is prepared from the colony derived from the second cell population, the ESC-like cell has a tetraploid karyotype. When the ESC-like cell having tetraploid karyotype is induced to differentiate, the ESC-like cell becomes to have a diploid karyotype. In accordance with this invention, diploid-to-tetraploid and tetraploid-to-diploid shifts occur during the acquisition of sternness by reprogramming and dedifferentiation and during differentiation into somatic cells, respectively. These novel findings form mechanism and theory underlying this invention.

In contrast to this, where the ESC-like cell is prepared from the colony derived from the first cell population, the ESC-like cell has a diploid karyotype.

The preparation of pluripotent ESC-like cells may be evaluated by maker assays using alkaline phosphatase (AP), anti-stage-specific embryonic antigen (SSEA) antibodies such as anti-SSEA-1, anti-SSEA-3 and anti-SSEA-4 antibodies, anti-integrin α6 antibody, and anti-integrin β1 antibody. In addition, the pluripotent stem cells finally prepared by the invention may be confirmed by analyzing their potentials to form embryonic body in the absence of LIF and teratoma. Meanwhile, the karyotyping and DNA microsatellite analysis of ESC-like cells finally produced may reveal that they are originated from tissue cells (e.g., ovarian cells or fibroblasts) targeted to be dedifferentiated.

According to a preferred embodiment, ESC-like cells originated from either the first cell population or the second somatic cell population show a positive reactivity to alkaline phosphatase, and to an antibody against each of alkaline phosphatase, stage specific embryonic antigen (SSEA)-1, integrin α6, integrin β1 and Oct-4, and a negative reactivity to an antibody against each SSEA-3 and SSEA-4.

According to a preferred embodiment, pluripotent ESC-like cells produced by the present method express at least one stem-cell specific gene selected from the group consisting of Oct-4, Nanog, Rex-1, Cripto, Dnmt3b, Tert, Lif Rc, Stat3, Bmp4, Fgf4, Foxd3, Sox2, CD9, and Gdf3. According to a preferred embodiment, ESC-like cells produced by the present method show a negative reactivity to an antibody against tissue-specific stem cell markers (Sca-1 and CD44 for mesenchymal stem cells, CD34 for epithelial stem cells, CD45 for hematopoietic stem cell, and Fragilis and Vasa for germline stem cells). Preferably, ESC-like cells established by the present method show no reactivity to an antibody against follicle cell-specific markers [e.g., AMH (anti-mullerian hormone)].

As discussed hereinabove, the present method provides two approaches for preparing ESC-like cells by use of mammalian tissue cells.

The first approach uses a niche derived from mammalian tissues or body fluids. Specifically, the first approach comprises the steps of: (a) obtaining an ovarian niche from a mammalian ovary wherein the ovarian niche comprises adult stem cells; (b) obtaining a somatic cell population from a mammalian tissue to be dedifferentiated, wherein the mammalian tissue is different from the ovarian niche in step (a) and the somatic cell population is different from the ovarian niche; (c) coculturing the ovarian niche and the somatic cell population in a medium for a period of time sufficient to form a colony from the somatic cell population; and (d) subculturing a cell from the colony in a medium for a period time sufficient to prepare the ESC-like cell.

In particular, the second approach comprises the steps of: (a) obtaining a first cell population from a mammalian tissue or body fluid, wherein the first cell population comprises adult stem cells; (b) obtaining a second somatic cell population from a mammalian tissue, wherein the mammalian tissue is different from the mammalian tissue in step (a) and the second cell population is different from the first cell population; (c) coculturing the first cell population and the second cell population in a medium containing leukemia inhibitory factor for a period of time sufficient to form a colony from the first cell population; and (d) subculturing a cell from the colony in a medium containing leukemia inhibitory factor for a period time sufficient to prepare the ESC-like cell.

The detailed descriptions of the first and second approaches follow those of the present method for preparing ESC-like cells discussed hereinabove.

In another aspect of this invention, there is provided a mammalian tissue-derived embryonic stem cell-like cell, wherein the embryonic stem cell-like cell has pluripotency and is prepared by culturing cells from a post-puberty mammalian tissue; and the embryonic stem cell-like cell is not prepared by a somatic cell nuclear transfer.

In still another aspect of this invention, there is provided a mammalian tissue or body fluid-derived embryonic stem cell (ESC)-like cell, wherein the ESC-like cell has pluripotency; the ESC-like cell is prepared by coculturing (i) an adult stem cell-containing first cell population from a mammalian tissue or body fluid and (ii) a second somatic cell population from a mammalian tissue different from the mammalian tissue of (i); and the ESC-like cell is not prepared by a somatic cell nuclear transfer.

In further aspect of this invention, there is provided a mammalian tissue or body fluid-derived embryonic stem cell (ESC)-like cell line, wherein the ESC-like cell has pluripotency; the ESC-like cell is prepared by coculturing (i) an adult stem cell-containing first cell population from a mammalian tissue or body fluid and (ii) a second somatic cell population from a mammalian tissue different from the mammalian tissue of (i); and the ESC-like cell is not prepared by a somatic cell nuclear transfer.

The mammalian tissue-derived pluripotent ESC-like cell of this invention is firstly presented without undertaking human cloning and SCNT. Where the somatic cell is derived from patient oneself, the pluripotent ESC-like cell enables to provide an immune reaction-free, patient-specific cell therapy without undertaking human cloning and SCNT.

The ESC-like cell of this invention is pluripotent. The term "pluripotent" means that cells have the ability to develop into any cell derived from the three main germ cell layers. When transferred into SCID mice, a successful somatic cell-derived pluripotent stem cell will differentiate into cells derived from all three embryonic germ layers. In addition, when cultured in the absence of LIF, the somatic cell-derived pluripotent stem cell of this invention forms an embryonic body being positive for markers specific for any of the three germ layers: neural cadherin adhesion molecule and S-100 for the ectodermal layer; muscle actin and desmin for the mesodermal layer; and α-fetoprotein and Troma-1 for endodermal cells.

The term "ESC-like cell line" used herein means a culture of cells obtained by long-term culture of the pluripotent ESC-like cells. The ESC-like stem cell line is stabile in the senses that it can be cultured for a period of time without substantially undergoing changes (e.g., genetically or biologically).

According to a preferred embodiment, the mammalian tissue or body fluid for the adult stem cell-containing first cell population is derived from ovary, bone marrow, peripheral blood, umbilical cord blood, amniotic fluid, brain, blood vessel, skeletal muscle, epithelia of skin or gastrointestinal tract, cornea, dental pulp of tooth, retina, liver, spleen or pancreas. Most preferably, the mammalian tissue is derived from ovary.

According to a preferred embodiment, the first cell population is a heterogeneous population comprising at least two cell types. Preferably, the second somatic cell population is a homogenous population substantially comprising one somatic cell type. The somatic cell, preferably, is fibroblast or epithelia cell. It is preferred that the second somatic cell population is a mitotically inactive cell. In addition, it is preferred that the second somatic cell population has adherent characteristics to culture plates.

According to a preferred embodiment, the first cell population is obtained from a post-puberty mammalian tissue or body fluid.

It is preferable that the first cell population comprising stem cells is an ovarian cell, more preferably, substantially freed from ovarian stromal cells. It is more preferable that the ovarian cell is substantially freed from oocytes and preantral and antral follicles.

The ESC-like cells of this invention may be originated from various animals, preferably, human, bovine, sheep, ovine, pig, horse, rabbit, goat, mouse, hamster or rat.

According to a preferred embodiment, when the ESC-like cell is originated from the second cell population, the ESC-like cell has a tetraploid karyotype. Where the ESC-like cell with tetraploid karyotype is induced to differentiate, the ESC-like cell has a diploid karyotype.

Unlikely, when the ESC-like cell is originated from the first cell population, the ESC-like cell has a diploid karyotype.

The mammalian tissue cell-derived ESC-like cell has the same genotype as its progenitor cell. In addition, ESC-like cell of this invention exhibits some characteristics common to embryonic stem cells, for example, being stainable with alkaline phosphatase (AP) and capable of forming an embryonic body and teratoma.

The term "stainable" used herein with reference to embryonic stem cells means that cells are positively stained with or reactive to cell surface binding ligands such as AP, anti-SSEA antibody, anti-integrin α6 antibody and anti-integrin β1 antibody.

According to a preferred embodiment, when the ESC-like cell is originated from the first cell population, the ESC-like cell shows a positive reactivity to alkaline phosphatase, and to an antibody against each of stage specific embryonic antigen (SSEA)-1, integrin α6, integrin β1 and Oct-4, and a negative reactivity to an antibody against each SSEA-3 and SSEA-4. Preferably, the ESC-like cell expresses at least one stem-cell specific gene selected from the group consisting of Oct-4, Nanog, Rex-1, Cripto, Dnmt3b, Tert, Lif Rc, Stat3, Bmp4, Fgf4, Foxd3, Sox2, CD9, and Gdf3. More preferably, the ESC-like cell shows a negative reactivity to an antibody against Sca-1, CD44, CD34, CD45, Fragilis, Vasa and/or AMH (anti-mullerian hormone).

Exemplarily, the ESC-like cell originated from the first cell population is OSC-B6D2-SNU-1 under accession No. KCLRF-BP-00148.

According to a preferred embodiment, when the ESC-like cell is originated from the second cell population, the ESC-like cell shows a positive reactivity to alkaline phosphatase, and to an antibody against each of stage specific embryonic antigen (SSEA)-1, integrin α6, integrin β1 and Oct-4, and a negative reactivity to an antibody against each SSEA-3 and SSEA-4.

The exemplified ESC-like cell originated from the second cell population is tScB6CD-SNU-1 under accession No. KCLRF-BP-00135.

It is well known that ES cells or ESC-like cells are capable of differentiating into any type of cells. Therefore, the ESC-like of this invention may be a good source providing various types of cells. For example, the ESC-like cell may be induced to differentiate into hematopoietic cells, nerve cells, beta cells, muscle cells, liver cells, cartilage cells, epithelial cell, urinary tract cell and the like, by culturing it a medium under conditions for cell differentiation. Medium and methods which result in the differentiation of ES cells are known in the art as are suitable culturing conditions (Palacios, et al., *PNAS. USA,* 92:7530-7537 (1995); Pedersen, *J. Reprod. Fertil. Dev.,* 6:543-552 (1994); and Bain et al., *Dev. Biol,* 168:342-357 (1995)).

The ESC-like cell of this invention has numerous therapeutic applications through transplantation therapies. The ESC-like cell of this invention has application in the treatment of numerous diseases or disorders such as diabetes, Parkinson's disease, Alzheimer's disease, cancer, spinal cord injuries, multiple sclerosis, amyotrophic lateral sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

In still further aspect of this invention, there is provided a culture medium for a culture medium for dedifferentiating a mammalian cell having no pluripotency into an embryonic stem cell (ESC)-like cell having pluripotency, which comprises a cell population from a mammalian tissue or body fluid, wherein the cell population comprises adult stem cells.

The culture medium of this invention is also described using the term "culture system" and these two terms will be used interchangeably.

Since the culture medium or culture system of this invention is used in the method of this invention for producing ESC-like cells described hereinabove, the common descriptions between them will be omitted in order to avoid undue redundancy leading to the complexity of this specification.

According to a preferred embodiment, the mammalian tissue or body fluid is derived from ovary, bone marrow, peripheral blood, umbilical cord blood, amniotic fluid, brain, blood vessel, skeletal muscle, epithelia of skin or gastrointestinal tract, cornea, dental pulp of tooth, retina, liver, spleen or pancreas. More preferably, the cell population comprises ovarian cells. It is preferable that the cell population is a heterogeneous population comprising at least two cell types.

According to a preferred embodiment, the medium further comprises at least 3,000 units/ml of leukemia inhibitory factor, more preferably, at least 4,000 units/ml of leukemia inhibitory factor, and most preferably, 4,000-6,000 units/ml of leukemia inhibitory factor.

According to a preferred embodiment, the mammalian cell is a somatic cell, more preferably, mitotically inactive somatic cell.

In another aspect of this invention, there is provided a culture medium for producing an embryonic stem cell (ESC)-like cell from a mammalian tissue cell, which comprises at least 3,000 units/ml of leukemia inhibitory factor.

According to a preferred embodiment, the medium comprises at least 4,000 units/ml of leukemia inhibitory factor, more preferably, 4,000-6,000 units/ml of leukemia inhibitory factor, most preferably, about 5,000 units/ml of leukemia inhibitory factor.

According to a preferred embodiment, the mammalian tissue cell is a cell obtained from a post-puberty mammalian.

It is preferable that the mammalian tissue cell is derived from ovary, bone marrow, peripheral blood, umbilical cord blood, amniotic fluid, brain, blood vessel, skeletal muscle, epithelia of skin or gastrointestinal tract, cornea, dental pulp of tooth, retina, liver, spleen or pancreas, most preferably, ovary.

According to a preferred embodiment, the mammalian tissue cell is a somatic cell.

According to a preferred embodiment, the medium further comprises a mitotically inactive cell layer such as mitotically inactive feeder layer.

The culture medium or system of this invention may further comprise any ingredient contained in conventional media for obtaining mammalian ES cells known in the art. For example, the medium may further comprise inorganic salts (e.g., $CaCl_2$, $Fe(NO_3)_3$, $MgSO_4$, NaCl, $NaHCO_3$ and $NaH_2PO_4$), energy source (e.g., glucose), buffers, amino acids and/or vitamins (e.g., D-Ca pantothenate, choline chloride, folic acid, nicotinamide), preferably supplemented with β-mercaptoethanol, nonessential amino acids, L-glutamine, antibiotics (preferably, penicillin and streptomycin) and/or FBS (fetal bovine serum). The composition of the culture medium of this invention may prepared in accordance with that of conventional media such as Dulbecco's modified Eagle's medium (DMEM), knock DMEM, DMEM containing fetal bovine serum (FBS), DMEM containing serum replacement, Chatot, Ziomek and Bavister (CZB) medium, Ham's F-10 containing fetal calf serum (FCS), Tyrodes-albumin-lactate-pyruvate (TALP), Dulbecco's phosphate buffered saline (PBS), and Eagle's and Whitten's media.

The present invention clearly demonstrates that ESC-like cells having pluripotency can be derived from any cell type, particularly, adult somatic cell, under microenvironment (niche). In other words, the microenvironment (niche) allows providing a novel approach to produce ESC-like cells. To our knowledge, this is the first invention on establishing autologous ESC-like cells without using somatic-cell nuclear transfer and gamete manipulation. This approach avoids the sacrifice both of ovulated oocytes having developmental competence and of viable embryos.

The present invention can suggests a new strategy for establishing pluripotent cells from human tissues without undertaking SCNT. This would bypass the ethical issues related to cell/tissue therapy, as immune-specific pluripotent cells can be derived from any somatic cell of individuals.

The present invention will now be described in further detail by examples. It would be obvious to those skilled in the art that these examples are intended to be more concretely illustrative and the scope of the present invention as set forth in the appended claims is not limited to or by the examples.

EXAMPLES

For ESC-Like Cells Derived from Fibroblast

Materials and Methods

Animals

Animals provided for this study were bred at the Laboratory of Embryology and Stem Cell Biology, Seoul National University, Korea. They were maintained under controlled conditions of lighting (14 L:10 D), temperature (20-22° C.), and humidity (40-60%). Female F1 hybrid (B6CBAF1) mice were produced by mating female C57BL/6 mice with male CBA/Ca mice and 8-week-old female mice were used as the donors of the ovaries. Pregnant C57BL/6 females mated with DBA2 male or outbred (ICR) 13.5 days post-coitus (dpc) were euthanized for the derivation of MEFs for primary culture and subculture. All of the procedures for animal management, breeding, and surgery followed the standard operation protocols of Seoul National University, and the review board of Experimental Animal Resources, Seoul National University, approved the usage of animals and the relevant experimental procedures (approval no. SNU-050331-2). Experimental samples were appropriately managed, and quality control of the laboratory facility and equipment was conducted.

In Situ Hybridization

An in situ hybridization detection system kit (DF132-60K; BioGenex, San Ramon, Calif.) and probe (Biognostik, Gottingen, Germany) were used according to the supplied protocol, which was optimized to minimize background signals. The collected ovarian tissues were frozen in optimal cutting temperature compound (Tissue-Tek OCT compound; Sakura, Torrance, Calif.) in liquid $N_2$. The cryo-samples were cut at 10-μm thickness and fixed at room temperature for 5 min in PBS that contained 4% (v/v) formaldehyde (Sigma-Aldrich). The slides were dehydrated in an ethanol series (70%, 80%, 90%, 95%, and 100%). The air-dried samples were prehybridized in HybriBuffer-ISH at 30° C. for 3 h. Hybridization was conducted in HybriBuffer-ISH that contained the Oct-4 or Nanog HybriProbe at 40° C. overnight. The slides were washed in 1× sodium chloride/sodium citrate solution (SSC) at room temperature for 5 min, in 0.1×SSC at 45° C. for 15 min, and in 1×PBS supplemented with 0.1% (v/v) Tween-20 (USB, Cleveland, Ohio) at room temperature for 3 min. The slides were incubated in Power Block Reagent at room temperature for 10 min and with the biotinylated anti-fluorescein antibody at room temperature for 40 min. After washing with 1×PBS supplemented with 0.1% (v/v) Tween-20, the slides were incubated in streptavidin-alkaline phosphatase conjugate at room temperature for 20 min, and washed with 1×PBS supplemented with 0.1% (v/v) Tween-20. Alkaline phosphatase was activated by incubating with Activation Buffer at room temperature for 1 min. The slides were developed with NBT/BCIP at room temperature for 15 min, mounted with Supermount, and observed under a phase-contrast microscope (BX51TF; Olympus).

Preparation of MEFs

Embryonic fibroblasts were collected from the 13.5-dpc fetuses (B6D2F1 for primary culture and ICR for subculture) of pregnant females. The visceral organs, head, and extremities of the fetuses were removed and the remaining tissue was cut into small pieces. The tissue pieces were incubated in 0.04% (v/v) trypsin-EDTA (Gibco Invitrogen) for 6 min with agitation, and subsequently centrifuged at 50×g for 2 min. The supernatants were diluted in 10% (v/v) FBS-containing DMEM medium (Gibco Invitrogen) and centrifuged at 100×g for 4 min. The pellets of the collected fibroblasts were suspended and replaced in DMEM medium for monolayer formation. When the fibroblasts formed a confluent monolayer, they were frozen in 10% dimethylsulfoxide (Gibco Invitrogen).

Ovarian Cell Preparation

The ovaries were collected and, after the removal of adherent tissue, the retrieved tissue was chopped using a surgical blade. The specimens were incubated initially for 30 min in a dissociation medium that consisted of a 50:50 (v:v) mixture of 0.25% (v/w) trypsin-EDTA (Gibco Invitrogen) and DMEM (Gibco Invitrogen) that was supplemented with 750 U/ml collagenase type I (Sigma-Aldrich, St. Louis, Mo.) and 0.03% (v/v) fetal bovine serum (FBS; HyClone), at 37° C. The dissociated cells were filtered through a 40-μm cell strainer (BD Falcon, Franklin Lakes, N.J.) and centrifuged at 390×g for 4 min. They were initially seeded into 60 mm×10 mm culture dishes. The stromal cells mixed in with the dissociated cells were removed 30 min after initial seeding and the buoyant cells present above the bottomed stromal cells were re-seeded onto MEF monolayers in the dishes. In some replications, the filtered cells were directly seeded onto MEF monolayer without stromal cell removal. The culture medium was DMEM medium that was supplemented with 0.1 mM β-mercaptoethanol (Gibco Invitrogen), 1% (v/v) nonessential amino acids (Gibco Invitrogen), 2 mM L-glutamine (Sigma-Aldrich), 1% (v/v) lyophilized mixture of penicillin and streptomycin (Gibco Invitrogen), 5,000 U/ml mouse LIF (Chemicon, Temecula, Calif.), and 15% (v/v) FBS (HyClone).

Coculture of MEFs and Ovarian Cells for Establishing ESCs

F1 hybrid (B6D2F1; C57BL/6×DBA2) MEF monolayers were treated with 10 μg/ml mitomycin C (Chemicon, Temecula, Calif.) for 3 hrs in gelatin-coated 35-mm tissue culture dishes and subsequently used for establishing colony-forming cells. The ovarian cells prepared were additionally seeded into the dishes that contained MEF monolayers and cultured at 37° C. under 5% $CO_2$ in a humidified air atmosphere. On day 4 of culture, the mixed population of the embryonic fibroblasts and ovarian cells reached confluency and subsequently replated on a new monolayer in 60-mm tissue culture dishes containing culture medium. The LIF concentration added to the culture medium ranged from 1,000 to 5,000 U/ml in primary culture and was fixed at 2,000 U/ml for the subcultures. At the end of the primary culture (on day 7 of culture), colony-forming cells were mechanically removed with a capillary pipette, dissociated with 0.25% (v/w) trypsin-EDTA (Gibco Invitrogen) and subcultured with the ICR MEF monolayer. Subpassaging was conducted in the presence of 2,000 U/ml LIF at intervals of 3 days, whereas the medium was changed daily.

Marker Staining of ESC-Like Cells

For characterization using stem cell-specific markers, colony-forming cells collected at the $20^{th}$ subpassage were fixed in 4% (v/v) formaldehyde (Sigma-Aldrich) at room temperature for 10 min. The reactivity of the colony-forming cells to alkaline phosphatase was assessed with Fast Red TR/naphthol AS-MX phosphate (Sigma-Aldrich). Monoclonal antibodies against stage-specific embryonic antigens (SSEA)-1 (MC-480), SSEA-3 (MC-631), SSEA-4 (MC-813-70), integrin α6 (P2C62C4), and integrin β1 (MH-25) were supplied by the Developmental Studies Hybridoma Bank (Iowa City, Iowa). The Oct-4 antibody was purchased from BD Biosciences (San Jose, Calif.). Localization of SSEA-1, SSEA-3, SSEA-4, Oct-4, integrin α6, and integrin β1 was performed using the Alexa Fluor 488-conjugated anti-mouse antibody (Molecular Probes, Eugene, Oreg.), the Alexa Fluor 568-conjugated anti-mouse antibody (Molecular Probes), and the DakoCytomation kit (DakoCytomation, Carpinteria, Calif.).

In Vitro and In Vivo Differentiation

To confirm spontaneous differentiation in vitro, the colony-forming cells were treated with 0.04% (v/v) trypsin-EDTA (Gibco Invitrogen), and the dissociated cells were subsequently transferred to 100-mm plastic Petri dishes that contained LIF-free DMEM (Gibco Invitrogen) that was supplemented with 15% (v/v) FBS (HyClone). The cells were grown until the EBs formed. The EBs were seeded separately into 96-well culture plates and cultured for 7 days. The EBs were stained with the following specific markers for the three germ layers: nestin (Santa Cruz Biotechnology, Santa Cruz, Calif.) and S-100 (Biodesign International, Saco, Me.) for ectodermal cells; muscle actin (Biodesign International) and desmin (Santa Cruz Biotechnology) for mesodermal cells; and α-fetoprotein (Biodesign International) and troma-1 (Hybridoma Bank) for endodermal cells. Antibody localization was performed with the DakoCytomation kit (DakoCytomation).

To confirm in vivo differentiation, $1\times10^7$ colony-forming cells retrieved at the $20^{th}$ subpassage were injected subcutaneously into adult NOD-SCID mice. Teratomas that formed in the subcutaneous region were collected 8 weeks post-transplantation and fixed with 4% (v/v) paraformaldehyde (Sigma-Aldrich). After embedding in paraffin blocks, the tissues were stained with hematoxylin and eosin for examination under a phase-contrast microscope (BX51TF; Olympus, Kogaku, Japan).

Induction of Differentiation into Neuronal Cells

For in vitro differentiation into neuronal lineage cells, the colony-forming cells were dissociated and plated onto a 0.1% gelatin-coated plastic culture dish at a density of $0.5\text{-}1.5\times10^4/cm^2$ in modified N2B27 medium that consisted of DMEM/F12 (Gibco Invitrogen) supplemented with N2 (Gibco Invitrogen) and B27 (Gibco Invitrogen). Morphological evaluation was conducted throughout the culture period and the culture medium was changed at intervals of 2 days. Differentiated cells were maintained by replating into fibronectin-coated tissue culture dishes. Immunohistochemical analysis was conducted subsequently. Differentiated cells were fixed with 4% (v/w) paraformaldehyde (Sigma-Aldrich) for 5 min, incubated in blocking solution (PBS supplemented with 5% FBS), and the fixed cells were reacted with primary antibodies directed against nestin (Santa Cruz Biotechnology), β-tubulin type III (Chemicon), O4 (Chemicon), and glial fibrillary acidic protein (GFAP; Chemicon). The antigen-antibody complexes were visualized by reacting with the following fluorescent secondary antibodies: Alexa Fluor 488-conjugated anti-goat (Molecular Probes); Alexa Fluor 568-conjugated anti-mouse (Molecular Probes); and Alexa Fluor 488-conjugated anti-mouse (Molecular Probes). The stained cells were observed under a laser scanning confocal microscope with a krypton-argon mixed gas laser excitation at 488 nm or 568 nm and using the fluorescein filter (Bio-Rad, Hemel Hempstead, UK).

Primer Design

The Primary3 software (Whitehead Institute/MIT Center for Genome Research) was used to design all the specific primers used in these experiments. All the PCR primers were designed based on mouse cDNA and genomic DNA sequences obtained from GenBank. The specificities of the designed primers were tested by conducting 40 PCR cycles of 95° C. for 30 sec, the annealing temperature (shown in table S6) for 45 sec, and 72° C. for 30 sec. The primer sequences are listed in Table 1.

TABLE 1

Oligonucleotide primers and PCR cycling conditions

| Genes | GenBank number | Primer sequence Sense (5' > 3') | Anti-sense (5' > 3') | Size (bp) | Temp |
|---|---|---|---|---|---|
| β-actin (RT) | X03672 | ACCGTGAAAAGATGACCCAG | TCTCAGCTGTGGTGGTGAAG | 254 | 60 |
| β-actin (R-T) | X03672 | TACCACAGGCATTGTGATGG | TCTTTGATGTCACGCACGATT | 200 | 60 |
| Oct-4 (RT, R-T) | M34381 | GAAGCCCTCCCTACAGCAGA | CAGAGCAGTGACGGGAACAG | 297 | 60 |
| Nanog (RT, R-T) | AY455282 | CCCCACAAGCCTTGGAATTA | CTCAAATCCCAGCAACCACA | 255 | 60 |
| Rex-1 (RT) | M28382 | ACATCCTAACCCACGCAAAG | TGATTTTCTGCCGTATGCAA | 294 | 60 |
| Rex-1 (R-T) | M28382 | TCCCCGTGTAACATACACCA | CTTCGTCCCCTTTGTCATGT | 247 | 60 |
| Cripto (RT) | M87321 | CTTTAAGCAGGGAGGTGGTG | TAAAGCCATCTGCCACAATG | 195 | 60 |
| Cripto (R-T) | M87321 | CGGAGATCTTGGCTGCTAAC | CTTCGACGGCTCGTAAAAAC | 200 | 60 |
| Dnmt3b (RT) | BC105922 | AGTCCATCGCTGTGGGAACT | GGGCGGGTATAATTCAGCAA | 226 | 60 |
| Dnmt3b (R-T) | BC105922 | GTCCGGAAAATCACCAAGAA | CCAGAAGAATGGACGGTTGT | 201 | 60 |
| Tert (RT) | AF051911 | GGATCCTGGCTACGTTCCTG | TGCCTGACCTCCTCTTGTGA | 208 | 60 |
| Tert (R-T) | AF051911 | GCAGTGGTCCGGAGAGATAG | ACACTGTGACGCAGGAAGTG | 224 | 60 |
| Lif Rc (RT, R-T) | BC031929 | GCTGAGTGGTAAAGATACCG | TTCGTTGGACTCATACAACA | 261 | 60 |
| Stat3 (RT) | AY299489 | TTTGGAATGAAGGGTACATC | CAAATGACATGTTGTTCAGC | 228 | 60 |
| Bmp4 (RT) | BC013459 | TGAGAGACCCCAGCCTAAGA | AAACTTGCTGGAAAGGCTCA | 259 | 60 |
| Fgf4 (RT) | BC104312 | CAGTCTTCTGGAGCTCTCTC | AGGAAGTGGGTTACCTTCAT | 282 | 60 |
| Foxd3 (RT) | AF067421 | CAAGAACAGCCTGGTGAAG | GTCCAGGGTCCAGTAGTTG | 262 | 60 |
| Sox2 (RT) | AB108673 | ACGCTCATGAAGAAGGATAA | GTAGGACATGCTGTAGGTGG | 345 | 60 |
| CD9 (RT) | U60473 | ATGCTACCACTGTTTCCAAC | ACAAGTTAAACTGGCAGCAT | 212 | 60 |
| Gdf3 (RT) | BC101963 | CGAGTTTCAAGACTCTGACC | TAGAGGACCTTCTGGAGACA | 276 | 60 |
| Ncam (R-T) | Y00051 | AGATGGTCAGTTGCTGCCAA | AGAAGACGGTGTGTCTGCTT | 187 | 60 |
| Nestin (R-T) | BC062893 | TAGAGGTGCAGCAGCTGCAG | AGCGATCTGACTCTGTAGAC | 170 | 60 |
| Smooth muscle actin (R-T) | NM_007392 | ACTGGGACGACATGGAAAAG | CATCTCCAGAGTCCAGCACA | 240 | 60 |
| Desmin (R-T) | NM_010043 | TGACAACCTGATAGACGACC | TTAAGGAACGCGATCTCCTC | 180 | 60 |
| α-fetoprotein (R-T) | BC066206 | TGCACGAAAATGAGTTTGGGA | TTGCAGCCAACACATCGCTA | 159 | 60 |
| Troma1 (R-T) | D90360 | ATCGAGATCACCACCTACCG | TCTTCACAACCACAGCCTTG | 241 | 60 |
| Zfy1 (gDNA) | AC163622 | GTTACTCATTTTCAGGTGTTCTGGG | GTGTCAGCTGTTATAGGATCAGTGA | 572 | 62 |
| Xist (gDNA) | AJ421479.1 | GAGATACATTTATTTGCTCA | GACTTAGTTTGGTTTCTTTA | 540 | 55 |

RT = Reverse Transcriptase Polymerase Chain Reaction, R-T = Real-Time Polymerase Chain Reaction, gDNA = genomic DNA Polymerase Chain Reaction.

Real-Time PCR Analysis

Total RNA of EBs collected at 7, 14, 21, 28, 35, and 42 days was extracted using the RNeasy Plus Mini Kit (Qiagen, Valencia, Calif.) according to the manufacturer's instructions. The cDNAs were synthesized from approximately 1 μg of total RNA using the Reverse Transcription System (Promega, Madison, Wis.). Subsequently, the expression levels of specific genes in EBs were quantified by real-time PCR using the DyNAmo HS SYBRGreen qPCR Kit (Finnzymes, Espoo, Finland). PCR amplification was performed in a final volume of 25 μl with the ABI PRISM 7700 sequence detection system (Applied Biosystems, Foster, Calif.) and using the cycling parameters of 2 min at 50° C., 15 min at 95° C., followed by 40 cycles of 15 sec at 95° C., 30 sec at 60° C., and 30 sec at 72° C. The dissociation curve was recorded to check the PCR specificity. The final optimized concentration of each primer was 300 nM, and the absence of inter- and/or intra-molecular duplex formation between primers was confirmed in a control real-time PCR reaction that lacked template. The mRNA level of each gene in each sample was normalized to that of β-actin. The relative mRNA level was presented as $2^{-\Delta\Delta Ct}$, where Ct=the threshold cycle for target amplification, $\Delta Ct = Ct_{target\ gene}$ (genes specific for the three embryonic germ layer cells)$-Ct_{internal\ reference}$ (β-actin), and $\Delta\Delta Ct = \Delta Ct_{sample}$ (EBs cultured for 0, 21, or 35 days)$-\Delta Ct_{calibrator}$ (EBs cultured for 7 days).

Sex Determination by Genomic DNA-PCR Analysis

Total genomic DNA from each established stem cell line was extracted using the G-spin Genomic DNA Extraction Kit (iNtRON Biotechnology, Seoul, Korea) according to the manufacturer's instruction. The extracted genomic DNA was subjected to PCR amplification with primers for the Zfy1 (Y chromosome-specific) and Xist (X chromosome-specific) genes. The PCR products were size-fractionated by 1.2% agarose gel electrophoresis and visualized by ethidium bromide staining.

Karyotyping and DNA Content Analysis by FACS

For karyotyping, the cells were incubated in medium that contained 0.1 μg/ml colcemid (Sigma-Aldrich) for 3 hrs at 37° C. in 5% $CO_2$ in a humidified air atmosphere. The treated cells were trypsinized and resuspended for 15 min in 0.075 M KCl (Sigma-Aldrich) at 37° C. The cells were then placed in a hypotonic solution and subsequently fixed in a 3:1 (v/v) mixture of methanol (Sigma-Aldrich) and acetic acid (Sigma-Aldrich). Chromosomes were spread onto heat-treated slides and stained with Giemsa solution (Gibco Invitrogen). Subsequently, the chromosomes were sorted using the Cytovision (Applied Imaging Co., Santa Clara, Calif.).

For FACS analysis to measure DNA content, the harvested cells were washed in $Ca^{2+}$- and $Mg^{2+}$-free Dulbecco's PBS (DPBS; Gibco Invitrogen) and suspended in 70% (v/v) ethanol (Sigma-Aldrich) for 1 hr at 4° C. The cells were centrifuged at 390×g for 4 min and resuspended in 0.5 ml of $Ca^{2+}$- and $Mg^{2+}$-free DPBS (Gibco Invitrogen) that contained 0.1 mg/ml ribonuclease (Sigma-Aldrich) and 0.1 mg/ml propidium iodide (Sigma-Aldrich). After 30 min at room temperature in the dark, the cell suspension was analyzed by a Becton Dickinson FACS-Vantage SE (Becton Dickinson, San Jose, Calif.) equipped with a two water-cooled laser. The data were analyzed using the CELL Quest™ ver. 3.3 software (Becton Dickinson).

Telomerase Activity Assay

Telomerase activity was determined using the $TRAP_{EZE}$ Telomerase Detection Kit (Chemicon) according to manufacturer's instructions. The six established lines were analyzed at the $20^{th}$ subpassage and PCR amplification was conducted for 27 cycles. The PCR product was separated by electrophoresis in non-denaturing polyacrylamide gels.

Chimera Formation

To confirm pluripotency on a larger scale, 10-15 colony-forming cells maintained for different numbers of subpassages (7-13 or 32-39) were aggregated with 8-cell embryos and, 20 h after aggregation, the blastocysts derived from the aggregated embryos were transferred to the uteri of 2.5-dpc pseudo-pregnant ICR females (S. A. Wood, N. D. Allen, J. Rossant, A. Auerbach, A. Nagy, *Nature* 365, 87 (1993)).

DNA Microsatellite Analysis

DNA microsatellite analysis was performed with genomic DNA samples from the E14 ES cells, B6D2F1 MEFs, B6CBAF1 tail, newly established ESC-like cells, and teratomas induced from established ESC-like cells. Three specific mouse microsatellite primers (D03Mit200, D11Mit4, and D15Mit159) were used (http://www.cidr.jhmi.edu/mouse/mmset.html). The genomic DNA from each sample was amplified by PCR for the three microsatellite loci. Forward primers were synthesized with a fluorescent tag (FAM, TET, or HEX) at the 5'-end, and fluorescent PCR amplification was performed with the PC808 program TEMP control system (ASTEC). The PCR products were subsequently analyzed in the ABI Prism 310 DNA automated sequencer (Applied Biosystems). Digital images were obtained using the Genescan Data Collection ver. 2.5 software (Applied Biosystems). Each fluorescent peak was quantified for base-pair size, peak height, and peak area.

Immunostaining of ESC-Like Cells, MEFs, and Mitotically Inactivated MEFs

The colony-forming ES cells and MEF with or without mitomycin treatment were fixed in 4% (v/v) formaldehyde (Sigma-Aldrich) at room temperature for 10 min. The fixed ESC-like cells were exposed to antibodies directed against Vasa (Abcam, Cambridge, UK), Fragilis (Abcam), and AMH (Abcam). The localization of Vasa, Fragilis, and AMH was detected using the Alexa Fluor 488-conjugated anti-rabbit antibody (Molecular Probes) and the DakoCytomation kit (DakoCytomation). Furthermore, the fixed MEFs and mitotically inactivated MEFs were exposed to antibodies directed against Oct-4 (BD Biosciences), Nanog (Abcam), Vasa (Abcam), Fragilis (Abcam), CD44 (Chemicon), CD45 (Chemicon) and AMH (Abcam). Antibody localization was performed with the DakoCytomation kit (DakoCytomation).

Immunofluorescence of Ovarian Tissue-Dissociated Cells and ESC-Like Cells

The dissociated ovarian cells were fixated in 70% ethanol for 1 hr at 4° C. The fixed cells were centrifuged at 390×g for 4 min and washed twice with 0.5 ml of $Ca^{2+}$- and $Mg^{2+}$-free DPBS (Gibco Invitrogen) that contained 2% (v/v) FBS (HyClone). The fixed ovarian tissue-dissociated cells were reacted for 1 hr at 4° C. with primary antibodies directed against Oct-4 (BD Biosciences), Nanog (Abcam), Vasa (Abcam), CD44 (Chemicon), and AMH (Abcam). Moreover, the ESC-like cells dissociated by 1 mM EDTA (BIONEER, Seoul, Korea) were reacted for 1 hr at room temperature with primary antibodies to PE-conjugated Sca-1 (BD Biosciences), FITC-conjugated CD44 (BD Biosciences), biotin-conjugated CD34 (BD Biosciences) and biotin-conjugated CD45 (BD Biosciences). Sca-1 and CD44 were specific markers for MSCs, while CD34 and CD45 were used for epithelial stem cell-specific and hematopoietic stem cell-specific markers, respectively. After washing twice, the antigen-antibody complexes were visualized with the following fluorescent secondary antibodies: Alexa Fluor 488-conjugated anti-mouse (Molecular Probes), Alexa Fluor 488-conjugated anti-rabbit (Molecular Probes), Alexa Fluor 568-conjugated anti-mouse (Molecular Probes), Alexa Fluor 568-conjugated anti-rat (Molecular Probes), and Streptavidin-phycoerythrin (SAv-PE, BD Biosciences). The stained ovarian tissue-dissociated cells were observed under a laser scanning confocal microscope (Bio-Rad), and the stained ESC-like cells were analyzed by flow cytometry (FACSCALIBUR, Becton Dickinson).

Analysis of Imprinted Genes

Bisulfite genomic sequencing of the differentially methylated region 2 (DMR2) of Igf2 was carried out as described previously (S. Sato, T. Yoshimizu, E. Sato, Y. Matsui, *Mol. Reprod. Dev.* 65, 41 (2003)). PCR amplification of each DMR2 region of the bisulfite-treated genomic DNAs was carried out using specific primers: Forward (1088-1107 bp) 5'-GTTGGGGATATGTGATATTTA-3', Reverse (1307-1330 bp) 5'-AAACCATAACCTTTAACCTCTCTA-3'. The nucleotide positions of primers referred to Igf2 DMR2 sequence (GenBank accession no. AY849922). Four regions (P1, P2, P3 and P4) in DMR2 are the position to analyze methylation. The cytosines of the CpGs are located at the following positions: 1227, 1229, 1234 and 1240 (GenBank accession no. AY849922).

Deposit of Somatic Cell-Derived ESC-Like Cell

Of the fibroblast-derived ESC-like cells showing all of the ES cell characteristics described above, one cell was named "tScB6CD-SNU-1" and deposited on May 16, 2006 in the International Depository Authority, the Korean Cell Line Research Foundation and was given accession No. KCLRF-BP-00135.

Results

We have continuously sought alternative techniques. During preparation of mouse embryonic fibroblasts (MEFs), we occasionally found colony-like, homogenous cell mass. Whereas, we detected embryonic stem cell (ESC)-specific Oct-4 and Nanog expression in medullar tissue near the blood vessels and the theca cell region of the ovarian follicles (FIG. 1). We further knew that cells dissociated from the ovaries contain ESC-, mesenchymal stem cell (MSC)-, germ cell- and/or follicular cell-specific marker-positive cells. First, we cultured the B6D2F1 embryonic fibroblasts alone or cultured dissociated ovarian cells of less than 40 μm in diameter (B6CBAF1) without fibroblasts in Dulbecco's minimal essential medium (DMEM) that contained 5,000 U/ml leukemia inhibitory factor (LIF). However, neither of these cultures yielded colonies (Table 2).

TABLE 2

Culturing of the mouse embryonic fibroblasts (MEF) used for primary culture with ovarian cells (B6D2F1; C57BL/6 × DBA2) or subpassage of colony-forming cells (ICR strain), and culturing of ovarian tissue cells with or without MEF feeder cells in medium[a] supplemented with leukemia inhibitory factor

| Trials | Culture of | Strain of MEF feeder | With (+)/without (−) mitomycin treatment | Colony formation |
|---|---|---|---|---|
| 1 | MEF only | ICR | + | No |
| 2 | MEF only | ICR | + | No |
| 3 | MEF only | ICR | + | No |
| 4 | MEF only | ICR | + | No |
| 5 | MEF only | ICR | + | No |
| 6 | MEF only | ICR | + | No |
| 1 | MEF only | ICR | − | No |
| 2 | MEF only | ICR | − | No |
| 3 | MEF only | ICR | − | No |
| 4 | MEF only | ICR | − | No |
| 5 | MEF only | ICR | − | No |
| 6 | MEF only | ICR | − | No |
| 1 | MEF only | B6D2F1 | + | No |
| 2 | MEF only | B6D2F1 | + | No |
| 3 | MEF only | B6D2F1 | + | No |
| 4 | MEF only | B6D2F1 | + | No |
| 5 | MEF only | B6D2F1 | + | No |
| 6 | MEF only | B6D2F1 | + | No |
| 1 | MEF only | B6D2F1 | − | No |
| 2 | MEF only | B6D2F1 | − | No |
| 3 | MEF only | B6D2F1 | − | No |
| 4 | MEF only | B6D2F1 | − | No |
| 5 | MEF only | B6D2F1 | − | No |
| 6 | MEF only | B6D2F1 | − | No |
| 1 | Ovarian cell only | N/A | N/A | No |
| 2 | Ovarian cell only | N/A | N/A | No |
| 3 | Ovarian cell only | N/A | N/A | No |
| 4 | Ovarian cell only | N/A | N/A | No |
| 5 | Ovarian cell only | N/A | N/A | No |
| 6 | Ovarian cell only | N/A | N/A | No |

N/A = Not Analysis

[a]DMEM supplemented with β-mercaptoethanol, non-essential amino acids, L-glutamine, lyophilized mixture of penicillin and streptomycin and fetal bovine serum was employed as a based medium.

Figure 2:
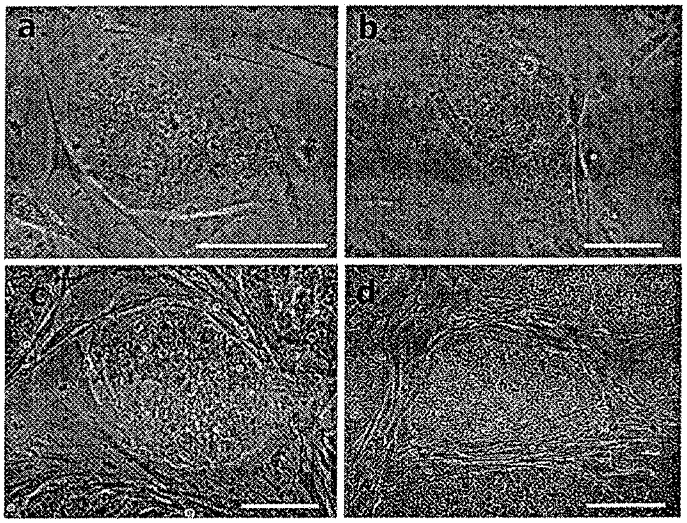
FIG. 2. Morphology of embryonic stem cell (ESC)-like cells derived by the coculturing of adult ovarian cells and embryonic fibroblasts. (a) Colony-forming ESCs of the E14 cell line. (b) Colony-forming ESC-like cells on day 7 of primary culture. (c) after ten subpassages (day 37 of culture) and (d) after 50 subpassages (day 157 of culture). Scale bar=50 μm.

We then cocultured the B6D2F1 fibroblasts with ovarian cells in DMEM, to which 1,000, 2,000 or 5,000 U/ml LIF was added. Colony-like cell aggregations were observed (Table 3), and, in total, 6/24 trials (25%) yielded colonies on day 7 of primary culture in 5,000 U/ml LIF-containing medium (FIG. 2). These colonies have been maintained for more than 6 months with 65 passages and have been stored in liquid nitrogen at −196° C.

TABLE 3

Outcome of culturing mouse embryonic fibroblasts[a,b] with ovarian tissue cells in media supplemented with different concentrations of leukemia inhibitory factor (LIF)

| Trials | LIF conc., in medium[c] (units/ml) | Colony formation[d] | Established cell line[d] |
|---|---|---|---|
| 1 | 1,000 | No | — |
| 2 | 2,000 | No | — |
| | 2,000 | No | — |
| 3 | 5,000 | Yes | Yes (tScB6CD-SNU-1) |
| 4 | 5,000 | No | — |
| 5 | 5,000 | No | — |
| | 5,000 | No | — |
| 6 | 5,000 | No | — |
| | 5,000 | No | — |
| | 5,000 | No | — |
| 7 | 5,000 | No | — |
| | 5,000 | No | — |
| | 5,000 | No | — |
| | 5,000 | No | — |
| | 5,000 | No | — |
| 8 | 5,000 | No | — |
| | 5,000 | Yes | Yes (tScB6CD-SNU-2) |
| 9 | 5,000 | Yes | Yes (tScB6CD-SNU-3) |
| | 5,000 | Yes | Yes (tScB6CD-SNU-4) |
| | 5,000 | No | — |
| | 5,000 | Yes | Yes (tScB6CD-SNU-5) |
| | 5,000 | No | — |

TABLE 3-continued

Outcome of culturing mouse embryonic fibroblasts[a,b] with ovarian tissue cells in media supplemented with different concentrations of leukemia inhibitory factor (LIF)

| Trials | LIF conc., in medium[c] (units/ml) | Colony formation[d] | Established cell line[d] |
|---|---|---|---|
| | 5,000 | Yes | Yes (tScB6CD-SNU-6) |
| | 5,000 | No | — |
| 10 | 5,000 | No | — |
| | 5,000 | No | — |
| | 5,000 | No | — |

[a]The embryonic fibroblast monolayer treated with mitomycin C was provided for cell culture.
[b]Retrieved from the 13.5-day-old fetuses in mated C57BL/6 females with DBA2 male
[c]Collected from 8-week-old, adult female F1 mice (B6CBAF1; C57BL/6 × CBA/Ca)
[d]DMEM supplemented with β-mercaptoethanol, non-essential amino acids, L-glutamine, lyophilized mixture of penicillin and streptomycin and fetal bovine serum was employed as a based medium.

Consequently, we attempted to clarify the progenitor cells of the established colony-forming cells. Short tandem repeat (STR) microsatellite analysis using three markers was undertaken to distinguish the genotypes of the ovarian cell donor, the fibroblasts and the control ESCs (129/Ola strain). The microsatellite loci of the established cells matched perfectly with those of the B6D2F1 fibroblast monolayer, and were completely different from those of the ovary donors and E14 ES cells (Tables 4a and 4b).

TABLE 4a

Short-tandom repeat microsatellite analysis of established embryonic stem cell-like cells, teratomas, and fibroblast donor stains

| D3Mit200[a] | | | D11Mit4[a] | | | |
|---|---|---|---|---|---|---|
| Sample | Size 1 | Size 2 | Sample | Size 1 | Size 2 | Size 3 |
| Ovary donor | 124.36 | — | Ovary donor | 248.72 | 295.13 | — |
| Feeder cell[b] | 101.09 | 124.29 | Feeder cell[b] | 248.75 | 285.14 | — |
| E14 | 124.36 | — | E14 | 248.92 | 293.22 | 295.33 |
| tScB6CD-SNU-1 | 101.16 | 124.31 | tScB6CD-SNU-1 | 248.98 | 285.09 | — |
| tScB6CD-SNU-2 | 101.09 | 124.31 | tScB6CD-SNU-2 | 248.93 | 285.14 | — |
| tScB6CD-SNU-3 | 101.09 | 124.34 | tScB6CD-SNU-3 | 248.88 | 285.30 | — |
| tScB6CD-SNU-4 | 101.03 | 124.20 | tScB6CD-SNU-4 | 248.66 | 285.08 | — |
| tScB6CD-SNU-5 | 101.24 | 124.41 | tScB6CD-SNU-5 | 248.87 | 285.08 | — |

TABLE 4a-continued

Short-tandom repeat microsatellite analysis of established embryonic stem cell-like cells, teratomas, and fibroblast donor stains

| D3Mit200[a] | | | D11Mit4[a] | | | |
|---|---|---|---|---|---|---|
| Sample | Size 1 | Size 2 | Sample | Size 1 | Size 2 | Size 3 |
| tScB6CD-SNU-6 | 101.17 | 124.31 | tScB6CD-SNU-6 | 248.71 | 285.10 | — |
| Teratoma | 101.04 | 124.17 | Teratoma | 248.91 | 285.34 | — |

TABLE 4b

Short-tandom repeat microsatellite analysis of established embryonic stem cell-like cells, teratomas, and fibroblast donor stains
D15Mit159[a]

| Sample | Size 1 | Size 2 |
|---|---|---|
| Ovary donor | 137.39 | 139.43 |
| Feeder cell[b] | 111.76 | 137.41 |
| EH | 139.45 | 141.62 |
| tScB6CD-SNU-1 | 111.97 | 137.54 |
| tScB6CD-SNU-2 | 110.79 | 137.41 |
| tScB6CD-SNU-3 | 110.76 | 139.45 |
| tScB6CD-SNU-4 | 111.85 | 137.45 |
| tScB6CD-SNU-5 | 111.76 | 137.42 |
| tScB6CD-SNU-6 | 111.79 | 137.41 |
| Teratoma | 110.83 | 138.50 |

Figure 3:
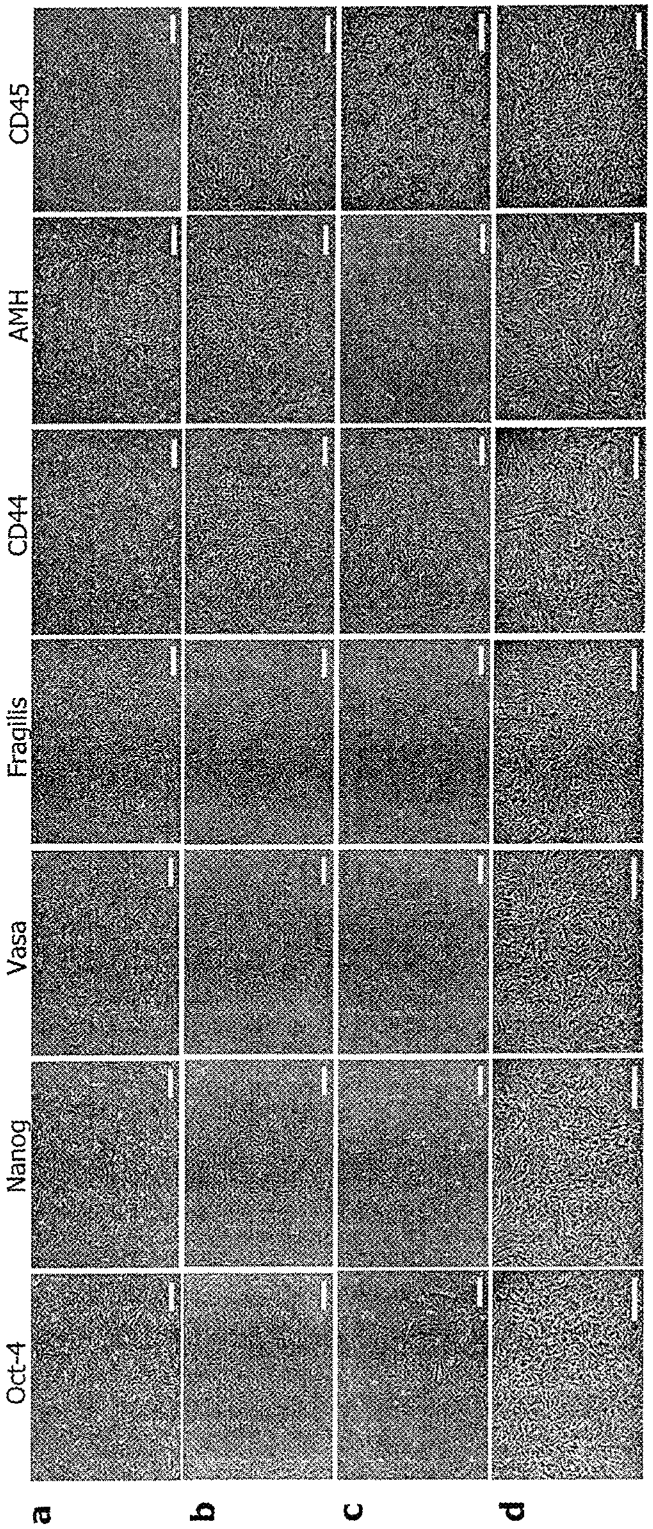
FIG. 3. Immunostaining with anti-Oct-4 (embryonic stem cell-specific), anti-Nanog (embryonic stem cell-specific), anti-Vasa (germ cell-specific), anti-Fragilis (germ cell-specific), anti-CD44 (mesenchymal stem cell-specific) or anti-AMH (follicular cell-specific) of B6D2F1 (C57BL/6×DBA2; a, c) and ICR (b, d) mouse embryonic fibroblasts (MEFs) with (c, d) or without (a, b) mitomycin C treatment. MEFs of each strain were collected from 13.5-day-old fetuses after removal of the internal organs, head, and extremities. Immunostaining of MEFs formed confluent monolayer was conducted. Confluent monolayer formation is detected, but none of the cells are positive for any of the markers tested. Scale bar=100 μm.

None of the cells in the fibroblast monolayer were not positive for specific markers of ESCs, germ cells, follicular cells, MSCs, and hematopoietic stem cells (FIG. 3). From these results, we conclude that MEFs are the origin of the established cells. The ovarian niche, which includes ovarian tissue-specific stem cells and germ cells, reprograms terminally-differentiated fibroblasts to acquire sternness. We continuously attempt to further establish the colony-forming cells from the fibroblasts of different strains and two more lines were derived from ICR mice.

Figure 4:
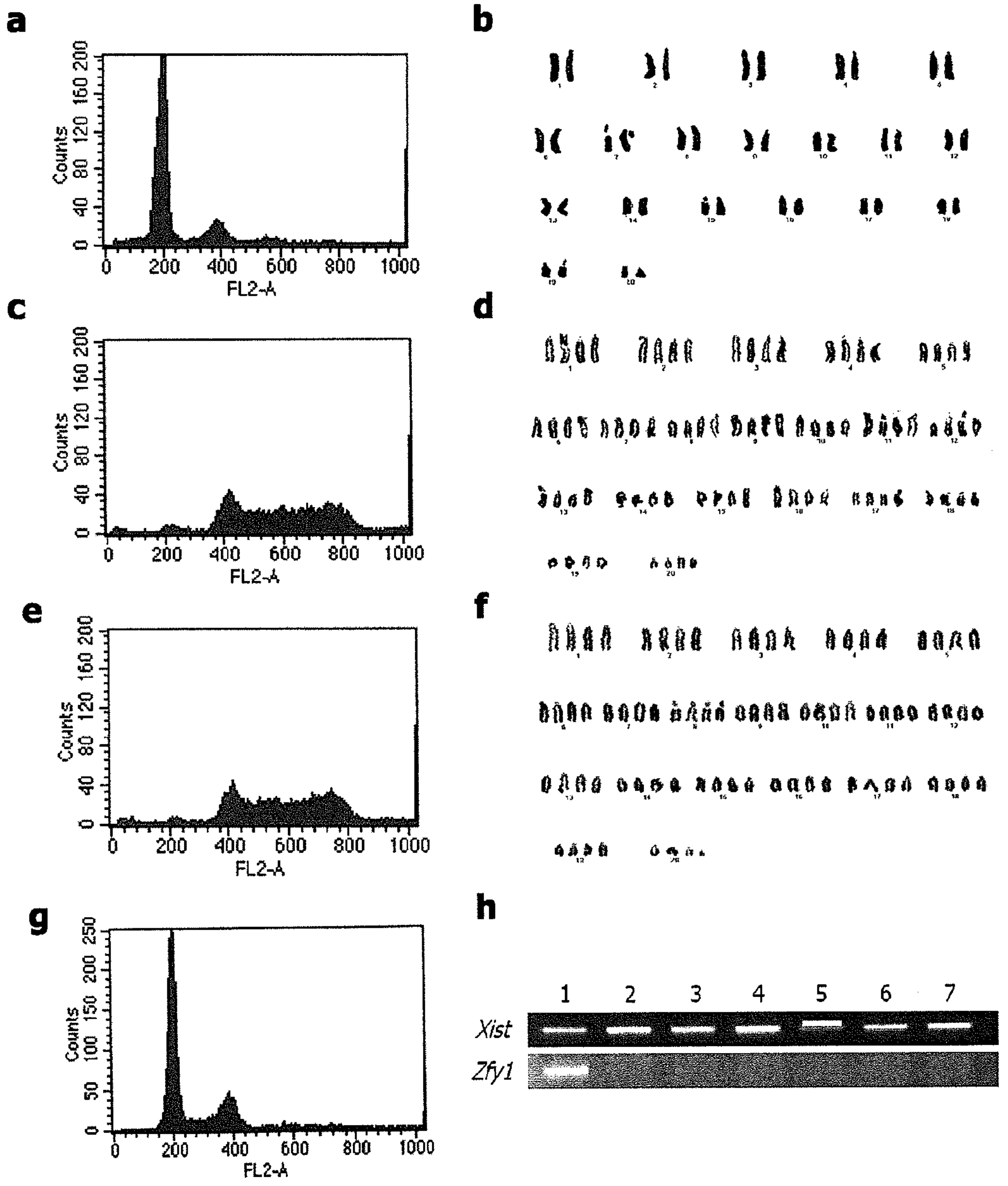
FIG. 4. Karyotyping of dissociated ovarian cells, established embryonic stem cell (ESC)-like cells and mouse embryonic fibroblast (MEF). Air-dried chromosome preparations were conducted using Cytovision and flow cytometry was used for effective karyotyping large population of cells. PCR analysis was further conducted using the X chromosome-specific Xist and Y chromosome-specific Zfy primers. The cells were immediately dissociated from the ovarian tissue (a, b) and MEF (g), and colony-forming cells (tScB6CD-SNU-1) were collected from early (6-9 passages; c, d) and late (30 passages; e, f) passages. The dissociated cells have diploid chromosomes, while the ESC-like cells collected from the early and late passages have tetraploid chromosomes. (h) PCR analysis of late-passage colony-forming cells. Lane 1, E14 cells with n lane 2, established ScB6CD-SNU-1; lane 3, ScB6CD-SNU-2 line; lane 4, established ScBCD-SNU-3 line; lane 5, established ScB6CD-SNU-4 line; lane 6, established ScB6CD-SNU-5 line; lane 7, established ScB6CD-SNU-6 line. The established ESC-like cells of all six lines express the X chromosome-specific Xist gene but not the Zfy gene.
Figure 5A:
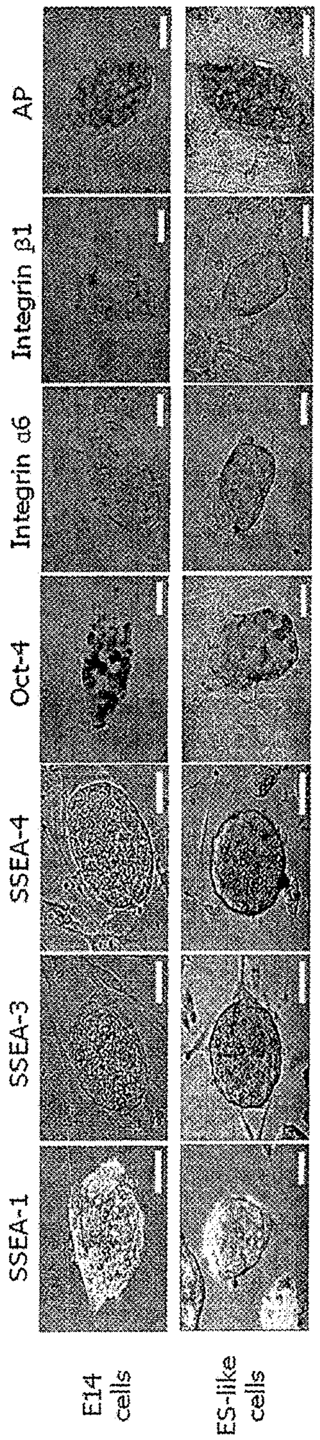
FIG. 5*a*. Similar to the E14 ES cell line, the ESC-like cells are positive for SSEA-1, Oct-4, integrin α6, integrin and AP. However, both the E14 ES cells and the established cells are negative for SSEA-3 and the SSEA-4. Scale bar=50 μm.
Figure 5B:
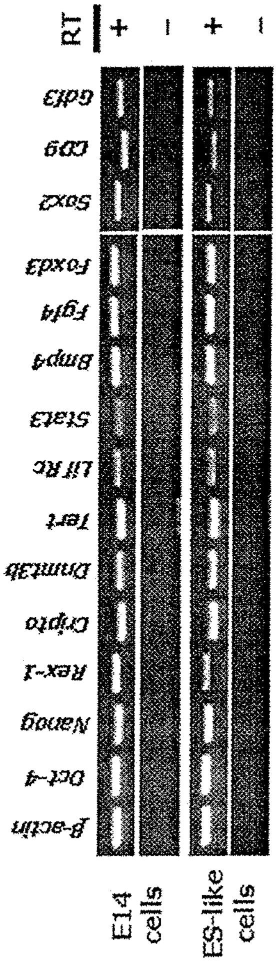
FIG. 5*b***. Both cell types express the pluripotent cell-specific Oct-4, Nanog, Rex-1, Cripto, Dnmt3b, Tert, Lif Rc, Stat3, Bmp4, Foxd3, Sox2, CD9, and Gdf3 genes. +, Reverse transcription using isolated total RNA, −, Non-reverse transcription using isolated total RNA.
Figure 6:
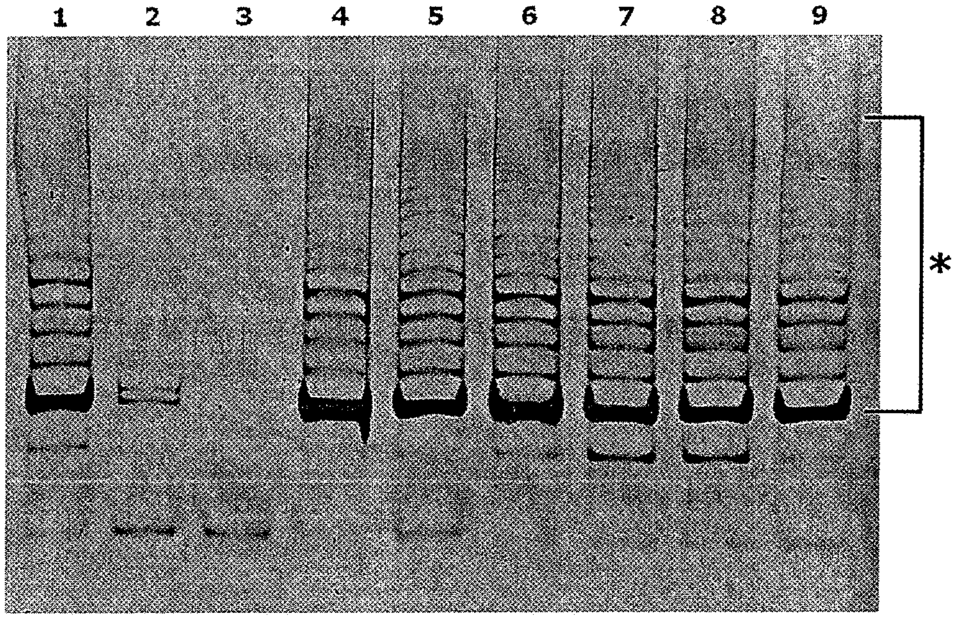
FIG. 6. Telomerase activities of the established embryonic stem cell (ESC)-like cells detected by the telomeric repeat amplication protocol assay. Six cell lines were evaluated. The ladder of telomerase products amplified by PCR was shown with six-base increments starting at 50 nucleotides at the portion indicated by the asterisk. All of the cell lines express high levels of telomerase activity. Lane 1, positive control (E14 embryonic stem cells); lane 2, MEFs; lane 3, PCR control without the addition of template; lanes 4-9, colony-forming cells of tScB6CD-SNU-1, tScB6CD-SNU-2, tScB6CD-SNU-3, tScB6CD-SNU-4, tScB6CD-SNU-5, and tScB6CD-SNU-6, respectively.

Next, we characterized the established colony-forming cells. All six lines had the XX sex chromosomes (FIG. 4). The karyotype of the colony-forming cells collected from early (6-7) or late (30) passages had the tetraploid karyotype, while no tetraploid cells were found in ovarian cells and MEFs. The colony-forming cells retrieved at the $20^{th}$ subpassage were positive for ESC-specific markers and expressed ESC-specific genes (FIGS. 5*a* and 5*b*). They had telomerase activity (FIG. 6) and 26-47% of the imprinted gene Igf2 in the established lines was methylated (Table 5).

TABLE 5

Bisulfite genomic sequencing analysis of the DMR2 of Igf2 in embryonic stem cell (ESC)-like cells of 6 lines and E14 cells of the control

| | Mean % (±SD) of methylation | | | |
|---|---|---|---|---|
| Cell lines | P1 | P2 | P3 | P4 |
| E14 | 52.19 ± 2.81 | 39.15 ± 2.71 | 39.04 ± 6.91 | 48.91 ± 4.79 |
| tScB6CD-SNU-1 | 48.64 ± 1.62 | 31.45 ± 1.57 | 34.24 ± 2.28 | 46.51 ± 2.36 |
| tScB6CD-SNU-2 | 33.25 ± 1.38 | 24.74 ± 0.81 | 21.98 ± 1.28 | 33.43 ± 2.72 |
| tScB6CD-SNU-3 | 39.08 ± 4.27 | 23.22 ± 1.83 | 24.94 ± 2.94 | 41.09 ± 2.77 |
| tScB6CD-SNU-4 | 47.51 ± 4.68 | 27.82 ± 1.57 | 27.87 ± 3.36 | 46.94 ± 2.87 |
| tScB6CD-SNU-5 | 36.94 ± 4.82 | 30.9 ± 3.72 | 31.25 ± 4.79 | 40.79 ± 4.79 |
| tScB6CD-SNU-6 | 40.36 ± 0.73 | 26.82 ± 2.69 | 28.57 ± 2.43 | 43.82 ± 3.33 |

Figure 7:
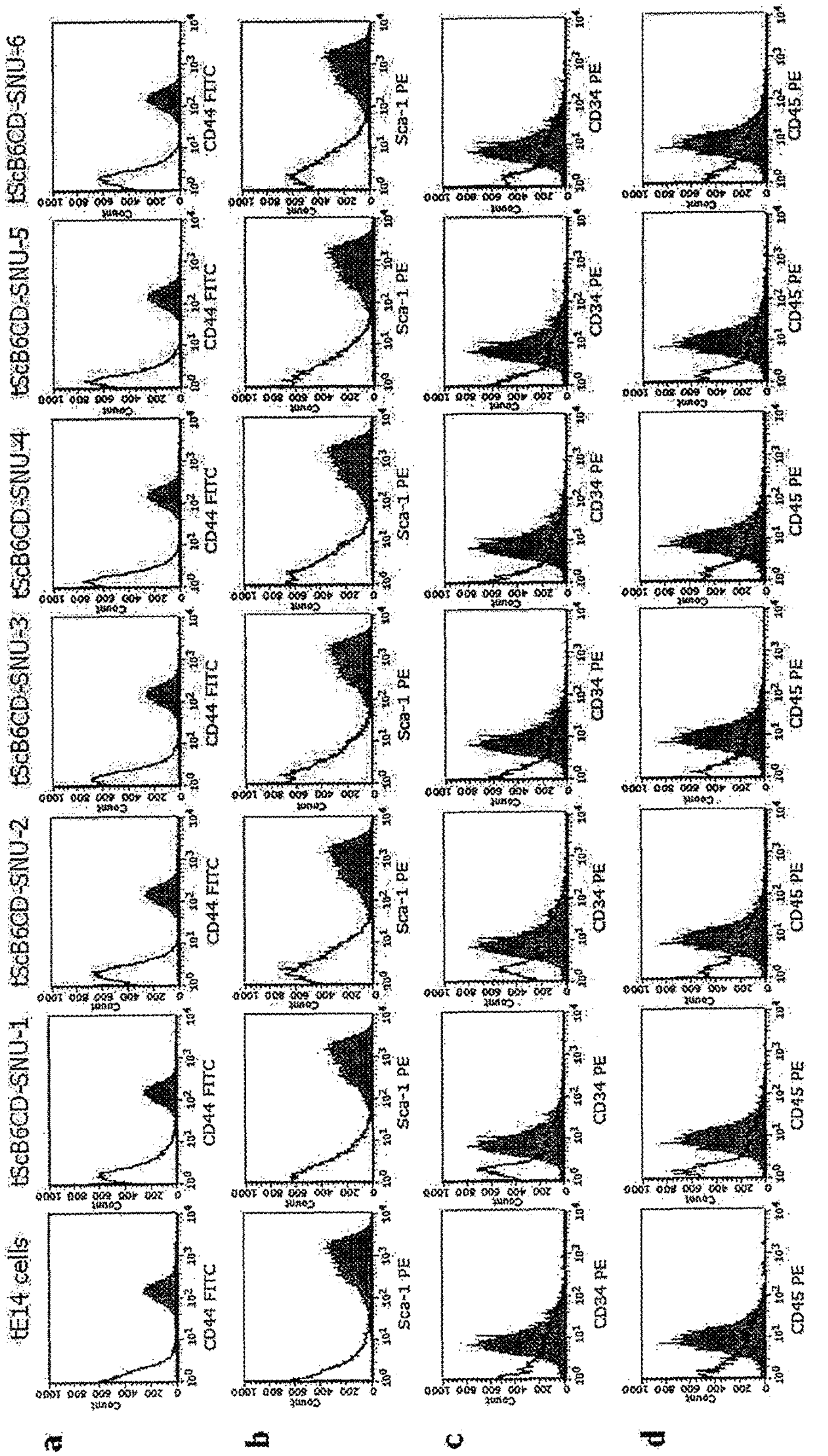
FIG. 7. Characterization of embryonic stem cell (ESC)-like cells by fluorescence activated cell sorting (FACS) analysis using mesenchymal stem cell (MSC)-specific marker CD44 (a) and Sca-1 (b), epithelial stem cell-specific marker CD34 (c) and hematopoietic stem cell-specific marker CD45 (d). The red color represents peaks of MSCs used as the control. The E14 ES and established ESC-like cells were all negative for anti-CD44, anti-Sca-1, anti-CD34 and anti-CD45 antibodies.
Figure 8:
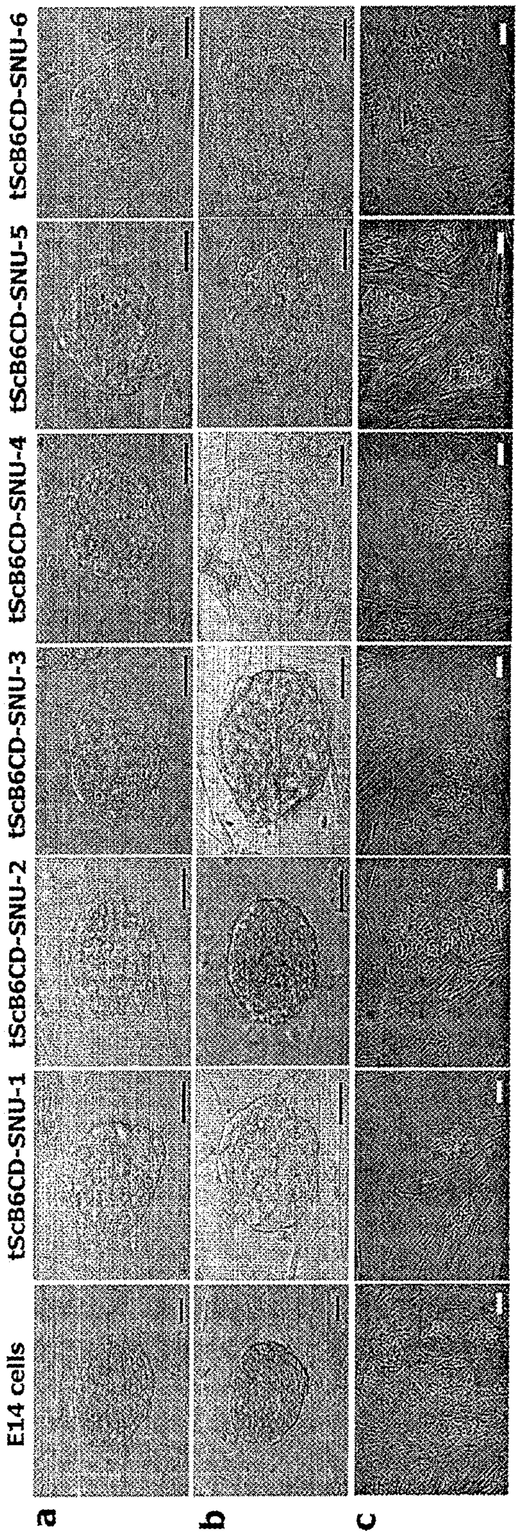
FIG. 8. Immunostaining of embryonic stem cell (ESC)-like cells with the Vasa and Fragilis germ cell-specific markers and with the follicular cell-specific marker AMH. All six lines of established ESC-like cells were analyzed. The colony-forming cells retrieved at the eighth subpassage are not positive for Vasa (a), Fragilis (b), and AMH (c). Scale bar=50 μm (a, b) and 100 μm (c).
Figure 9A:
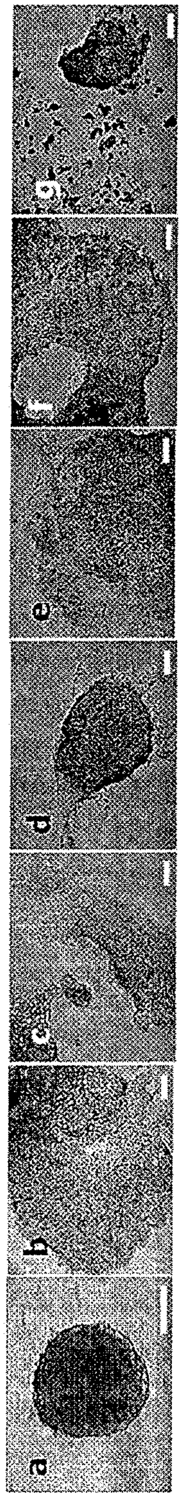
FIG. 9*a*-9*b*. In vitro differentiation of embryonic stem cell (ESC)-like cells derived from the coculturing of F1 (B6D2F1; C57BL/6×DBA2) embryonic fibroblasts and adult F1 (B6CBAF1; C57BL/6×CBA/Ca) ovarian cells. Colonies of the ESC-like cells were cultured in leukemia inhibitory factor (LIF)-free medium to allow differentiation into embryoid bodies (EBs).
Figure 9B:
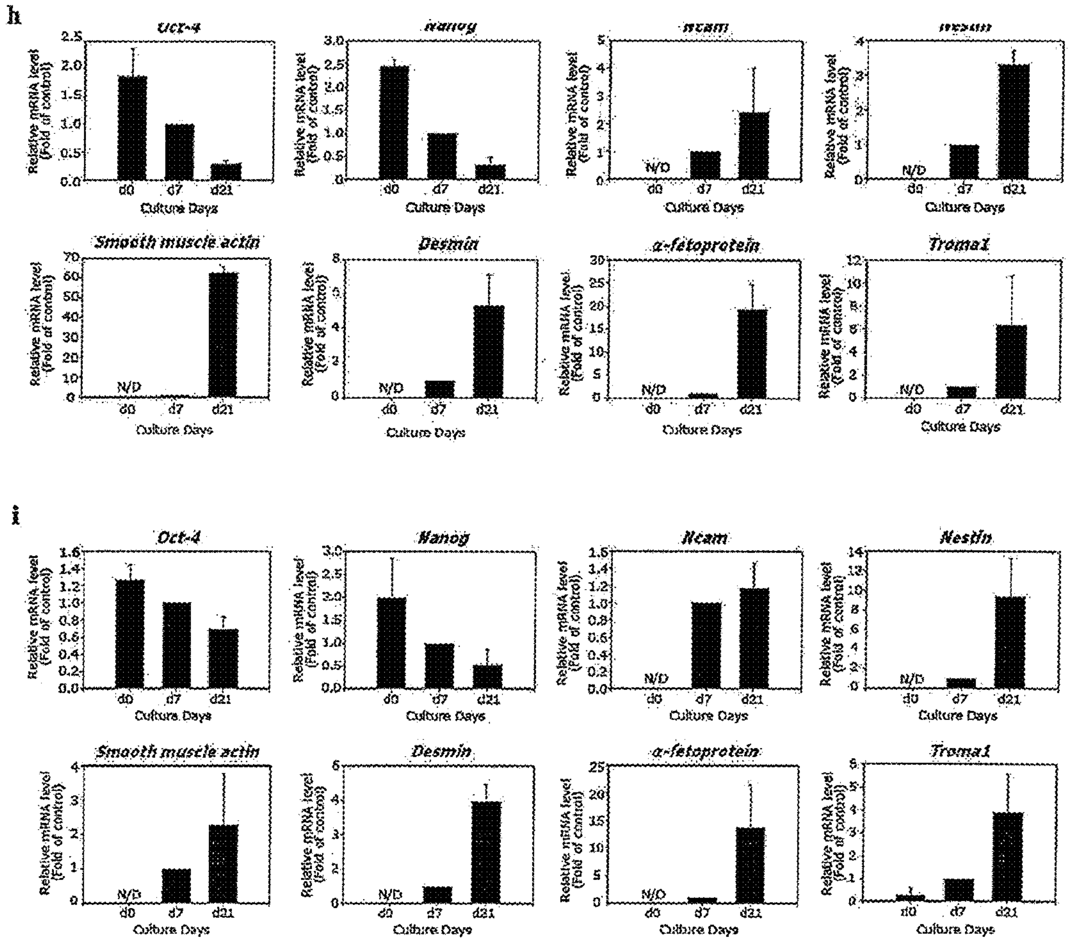
Figure 10:
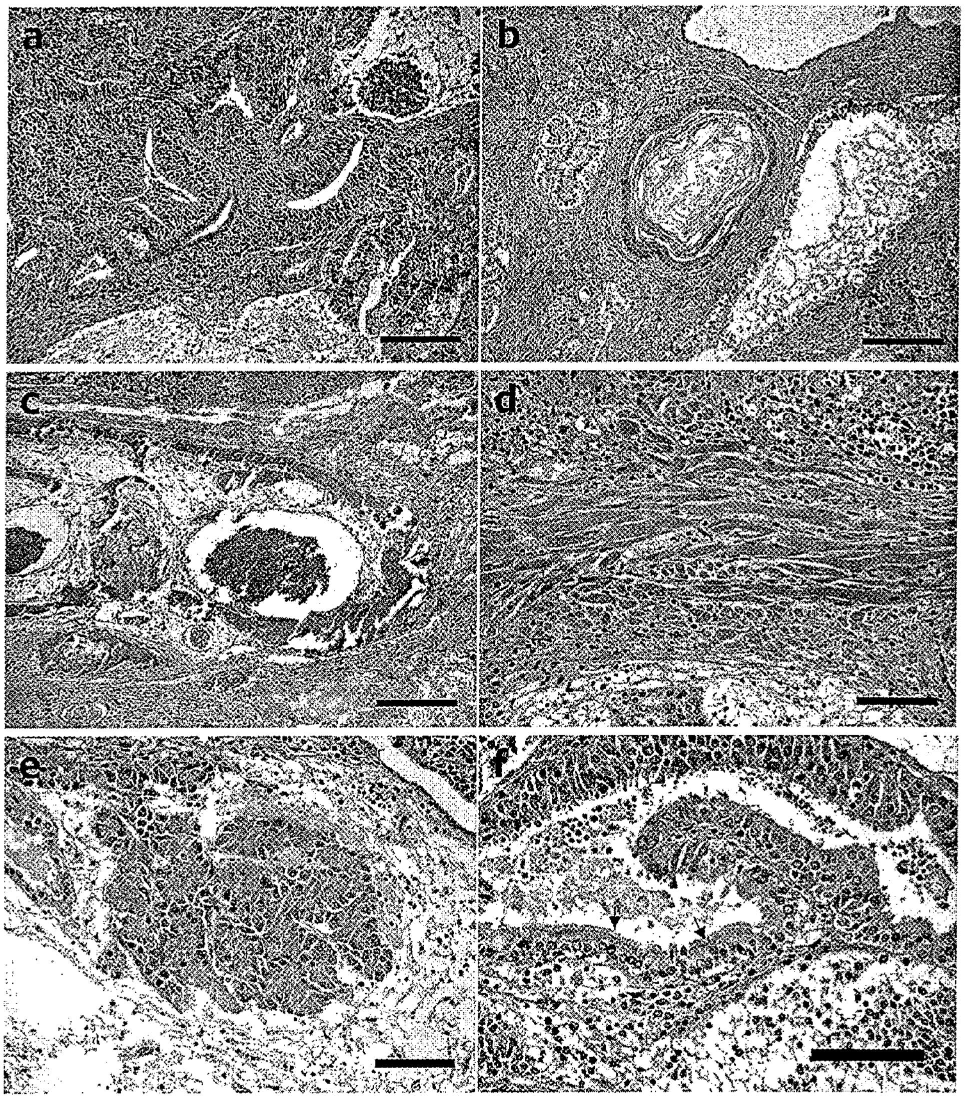
FIG. 10. In vivo differentiation of embryonic stem cell (ESC)-like cells after subcutaneous transplantation into NOD-SCID mice. The teratoma contained (a) ectodermal, neuroepithelial rosettes (scale bar=100 μm), (b) ectodermal, keratinized stratified squamous epithelial cells (scale bar=100 μm), (c) mesodermal, osteoid islands showing bony differentiation (scale bar=100 μm), (d) mesodermal muscle (scale bar=50 μm), (e) endodermal pancreatic tissue (scale bar=50 μm), and (f) endodermal, ciliated columnar epithelial cells (arrows) (scale bar=50 μm). This picture depicts the teratoma that resulted from the transplantation of ScB6CD-SNU-1.

Neither the established cells nor the E14 ES cells were positive for tissue-specific stem cell markers (Sca-1, CD44, AMH, Vasa and Fragilis; FIGS. 7-8). When the colony-forming cells were cultured in LIF-free medium, the cells formed embryoid bodies (EBs; FIG. 9) and subcutaneous transplantation of the colony-forming cells into NOD-SCID mice formed teratomas (FIG. 10). The colony-forming cells differentiated into neuronal cells in a spontaneous manner after being treated with N2B27 solution. To further verify pluripotency, the colony-forming cells collected at early (7-13 passages) and late (32-39 passages) subpassages were aggregated with 8-cell embryos, and the blastocysts derived from the aggregated embryos were transferred into the uteri of surrogate mothers. In all, 74 offspring were delivered, nine (12.2%) of which were somatic chimeras (Table 6).

TABLE 6

Production of somatic chimeras developed from transplanted blastocysts generated from embryos aggregated with established embryonic stem cell (ESC)-like cells

| Aggregated | No. of | | | No. (%)[b] of somatic chimeras | | | |
|---|---|---|---|---|---|---|---|
| stem cells subcultured | Embryos transferred | Recipient | Offsprings delivered[a] | Total | Live males | Live females | Dead |
| 7 to 13 times | 573 | 46 | 48 | 9 (19) | 1 | 3 | 5 |
| 32 to 39 times | 387 | 27 | 26 | 0 (0) | 0 | 0 | 0 |

The established cell line of ScB6CD-SNU-1 was used for aggregation with 8-cell embryos of ICR strain.
[a]In some cases, fetuses were delivered by cesarean section at 19.5 dpc, and transferred to nursing female mice.
[b]Percentage of the number of offsprings delivered.

Figure 11:
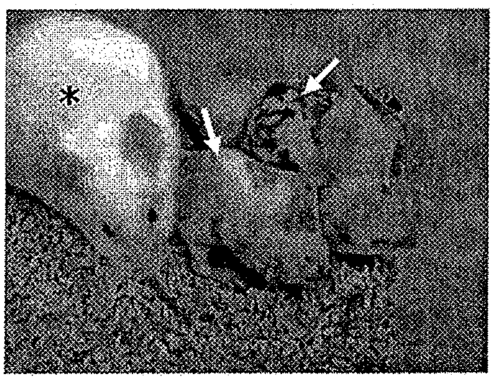
FIG. 11. Production of somatic chimeras by the aggregation of embryonic stem cell (ESC)-like cells derived from the coculturing of F1 (B6D2F1; C57BL/6×DBA2) embryonic fibroblasts and adult F1 (B6CBAF1; C57BL/6×CBA/Ca) ovarian cells with 8-cell embryos of the ICR strain. ESC-like cells (10-15 cells) were aggregated with 8-cell embryos and the blastocysts derived from the aggregated embryos were transplanted into the uterine horn of surrogate mothers. Live offspring with different coat and skin colors are determined to be somatic chimeras. Asterisks and arrows indicate the surrogate mothers and 10-day-old chimeric progenies, respectively.

Four of the chimeras lived (3 females and 1 male; FIG. 11). These results show that the established tetraploid cells are pluripotent stem cells, with almost similar properties as diploid ES cells (Tables 7a and 7b).

TABLE 7a

Summary of the characterization of the embryonic stem cell (ESC)-like cell lines derived from coculturing of adult ovarian cells and embryonic fibroblasts in mice

| | | Stem cell specific markers | | | | | | |
|---|---|---|---|---|---|---|---|---|
| Established ES cell line | Karyotype | AP | SSEA-1 | SSEA-3 | SSEA-4 | Oct-4 | Integrin α6 | Integrin β1 |
| tScB6CD-SNU-1 | Tetraploid, XX | + | + | − | − | + | + | + |
| tScB6CD-SNU-2 | Tetraploid, XX | + | + | − | − | + | + | + |
| tScB6CD-SNU-3 | Tetraploid, XX | + | + | − | − | + | + | + |
| tScB6CD-SNU-4 | Tetraploid, XX | + | + | − | − | + | + | + |
| tScB6CD-SNU-5 | Tetraploid, XX | + | + | − | − | + | + | + |
| tScB6CD-SNU-6 | Tetraploid, XX | + | + | − | − | + | + | + |

TABLE 7b

Summary of the characterization of the embryonic stem cell (ESC)-like cell lines derived from coculturing of adult ovarian cells and embryonic fibroblasts in mice

| Established ES cell line | Karyotype | Methylation % of IgF2 (Mean ± SD) | Telomerase activity | Neuronal cell differentiation | Formation of Teratoma | Formation of Embryoid body |
|---|---|---|---|---|---|---|
| tScB6CD-SNU-1 | Tetraploid, XX | 40.2 ± 1.5 | + | Yes | Yes | Yes |
| tScB6CD-SNU-2 | Tetraploid, XX | 28.4 ± 1.3 | + | Yes | Yes | Yes |
| tScB6CD-SNU-3 | Tetraploid, XX | 32.1 ± 1.8 | + | Yes | Burging | Yes |
| tScB6CD-SNU-4 | Tetraploid, XX | 37.5 ± 1.8 | + | Yes | Burging | Yes |
| tScB6CD-SNU-5 | Tetraploid, XX | 35.0 ± 1.7 | + | Yes | Burging | Yes |
| tScB6CD-SNU-6 | Tetraploid, XX | 34.9 ± 1.1 | + | Yes | Burging | Yes |

Figure 12:
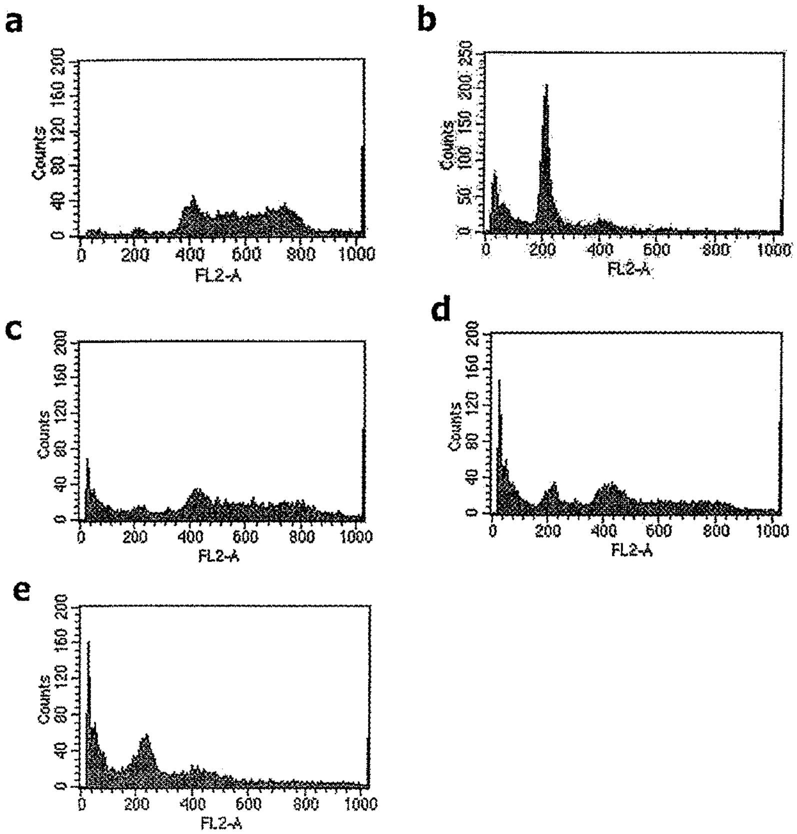
FIG. 12. Karyotyping of established embryonic stem cell (ESC)-like cells, in vivo-differentiated teratomas, and embryoid bodies (EBs) at 7, 14, and 21 days post-differentiation. FACS analysis was used to karyotype the established ESC-like cells of the ScB6CD-SNU-1 line. (a) ESC-like cells collected from late (30 passages) passages; (b) teratomas retrieved 8 weeks after transplantation into a SCID mouse; and EBs after 7 (c), 14 (d) and 21 (e) days of culture in leukemia inhibitory factor (LIF)-free medium. The ESC-like cells are tetraploidy, while there are no tetraploid cells in the teratomas. The number of diploid cells increases as spontaneous differentiation in vitro progresses up to 21 days.
Figure 13:
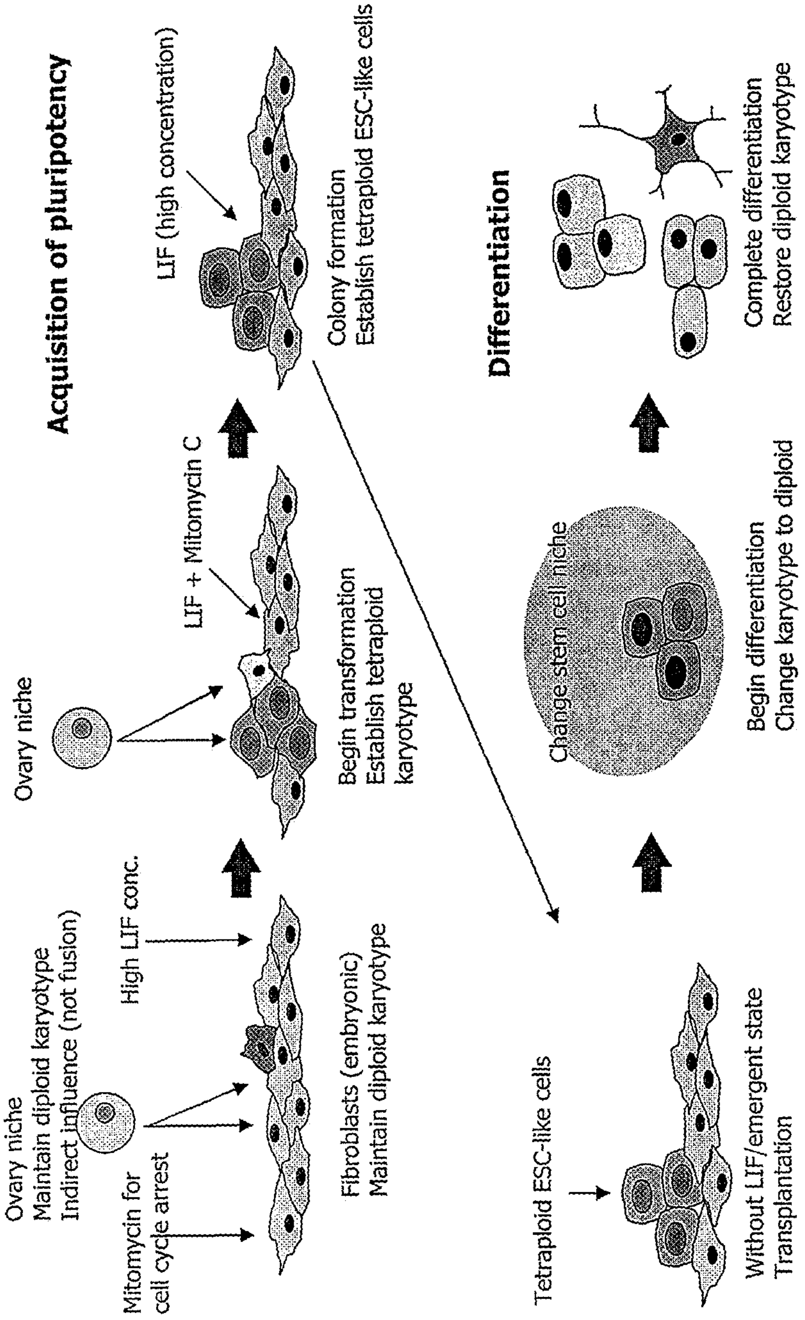
FIG. 13 schematically represents one specific example of the present process for preparing ESC-like cells the second somatic cell population containing adult stem cells with the help of ovarian niche.
Figure 14:
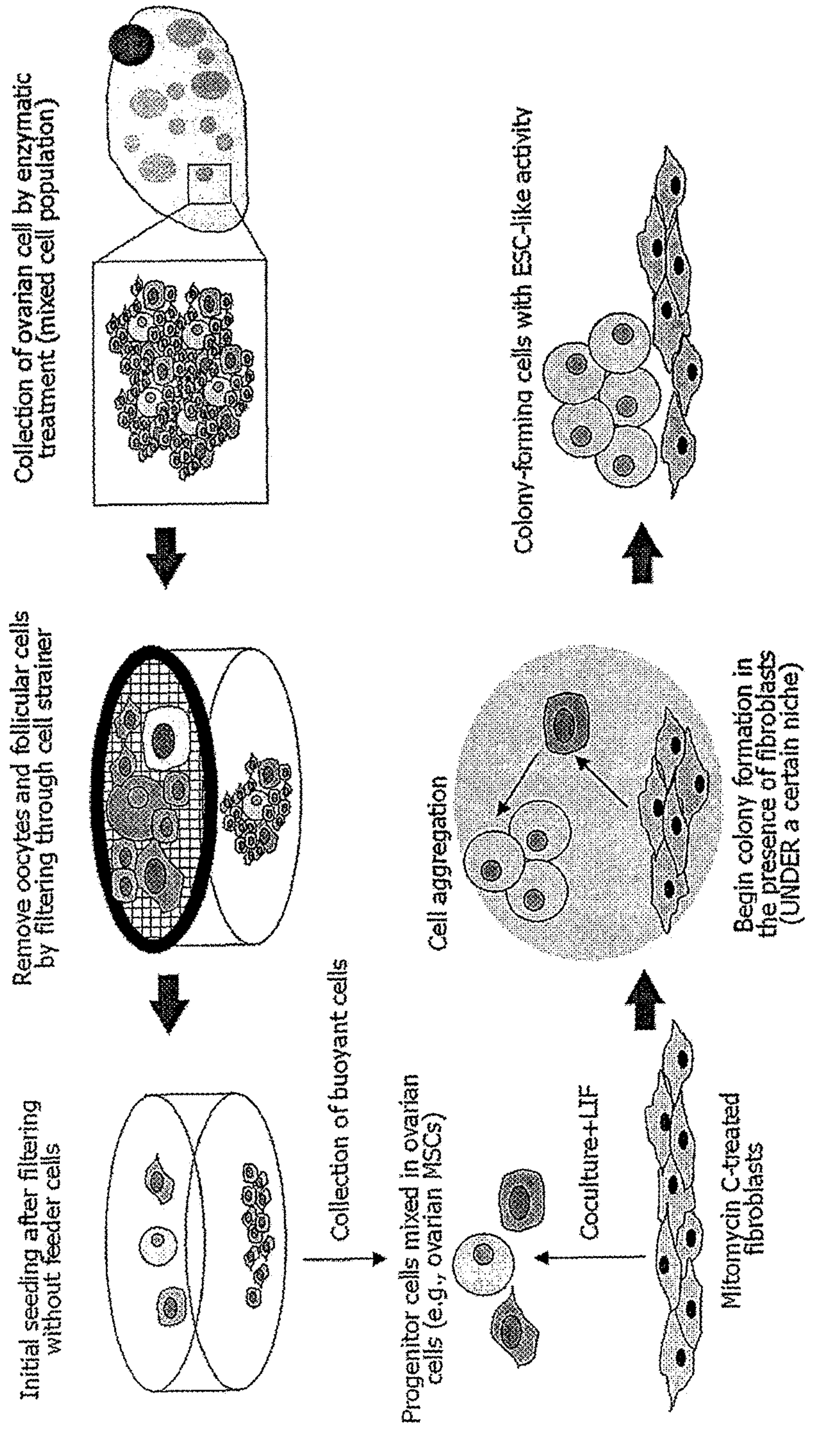
FIG. 14 schematically represents one specific example of the present process for preparing ESC-like cells the first cell population containing adult stem cells.

We evaluated whether the tetraploid ESC-like cells can restore the normal diploid karyotype after differentiation. No diploid cells were present among the established stem cells, while there were no tetraploid cells in the teratomas (FIG. 12). The population of diploid cells gradually increased as the EB was formed and the diploid cells finally predominated in the EBs collected from 21 days post-treatment. The results of the STR microsatellite analysis show that the genotype of the differentiated cells in the teratomas matched that of the feeder cell donor (Table 4). From these results, diploid-to-tetraploid and tetraploid-to-diploid shifts occur during the acquisition of sternness by reprogramming and dedifferentiation and during differentiation into somatic cells, respectively, which do not affect the genotype of the established cells.

EXAMPLES

For ESC-Like Cells Derived from Ovarian Cells

Materials and Methods

Animals

Animals provided for this study were bred at the Laboratory of Gamete and Stem Cell Biotechnology, Seoul National University, Korea. They were maintained under controlled conditions of lighting (14 L:10 D), temperature (20-22° C.), and humidity (40-60%). Female F1 hybrid (B6D2F1) mice were produced by mating female C57BL/6 mice with male DBA2 mice and 8-week-old female mice were used as the donors of the ovaries. All of the procedures for animal management, breeding, and surgery followed the standard operation protocols of Seoul National University, and the review board of Experimental Animal Resources, Seoul National University, approved the usage of animals and the relevant experimental procedures (approval no. SNU-050331-2). Experimental samples were properly managed, and quality control of the laboratory facility and equipment was conducted.

In Situ Hybridization

An in situ hybridization detection system kit (DF132-60K; BioGenex, San Ramon, Calif.) and probe (Biognostik, Gottingen, Germany) were used according to the supplied protocol, which was optimized to minimize background signals. The collected ovarian tissues of C57BL/6 or B6D2F1 (C57BL/6×DBA2) were frozen in optimal cutting temperature compound (Tissue-Tek OCT compound; Sakura, Torrance, Calif.) at −70° C. The cryo-samples were cut at 10-μm thickness and fixed at room temperature for 5 min in PBS that contained 4% (v/v) formaldehyde (Sigma-Aldrich). The slides were dehydrated in an ethanol series (70%, 80%, 90%, 95%, and 100%). The air-dried samples were prehybridized in HybriBuffer-ISH at 30° C. for 3 h. Hybridization was conducted in HybriBuffer-ISH that contained the Oct-4 or Nanog HybriProbe at 40° C. overnight. The slides were washed in 1× sodium chloride/sodium citrate solution (SSC) at room temperature for 5 min, in 0.1×SSC at 45° C. for 15 min, and in 1×PBS supplemented with 0.1% (v/v) Tween-20 (USB, Cleveland, Ohio) at room temperature for 3 min. The slides were incubated in Power Block Reagent at room temperature for 10 min and with the biotinylated anti-fluorescein antibody at room temperature for 40 min. After washing with 1×PBS supplemented with 0.1% (v/v) Tween-20 (USB), the slides were incubated in streptavidin-alkaline phosphatase conjugate at room temperature for 20 min, and washed with 1×PBS supplemented with 0.1% (v/v) Tween-20 (USB). Alkaline phosphatase was activated by incubating with Activation Buffer at room temperature for 1 min. The slides were developed with NBT/BCIP at room temperature for 15 min, mounted with Supermount, and observed under a phase-contrast microscope (BX51TF; Olympus).

Preparation of MEFs

Outbred (ICR) 13.5-day-old fetuses were euthanized for the derivation of MEFs for primary culture and subculture. Embryonic fibroblasts were collected from the fetuses, and the visceral organs, head, and extremities of the fetuses were removed. The remaining tissue was cut into small pieces and was subsequently incubated in 0.04% (v/v) trypsin-EDTA (Gibco Invitrogen, Grand Island, N.Y.) for 6 min with agitation at 37° C. After being centrifuged at 110×g for 2 min, the supernatants were diluted in 10% (v/v) fetal bovine serum (FBS; HyClone Laboratories, Logan, Utah)-containing DMEM medium (Gibco Invitrogen) and centrifuged at 390×g for 4 min. The pellets of the collected fibroblasts were suspended and replaced in DMEM medium for monolayer formation. When the fibroblasts formed a confluent monolayer, they were frozen in 10% dimethylsulfoxide (Gibco Invitrogen).

Ovarian Cell Preparation

The ovaries were collected and, after the removal of adherent tissue, the retrieved tissue was chopped using a surgical blade. The specimens were incubated initially for 30 min in a dissociation medium that consisted of a 50:50 (v:v) mixture of 0.25% (v/w) trypsin-EDTA (Gibco Invitrogen) and DMEM (Gibco Invitrogen) that was supplemented with 750 units/ml collagenase type I (Sigma-Aldrich, St. Louis, Mo.) and 0.03% (v/v) fetal bovine serum (FBS; HyClone), at 37° C. The dissociated cells were filtered through a 40-μm cell strainer (BD Falcon, Franklin Lakes, N.J.) and centrifuged at 390×g for 4 min. They were initially seeded into 60 mm×10 mm culture dishes. The stromal cells mixed in with the dissociated cells were removed 30 min after initial seeding and the buoyant cells present above the bottomed stromal cells were re-seeded onto MEF monolayers in the dishes. In some replications, the filtered cells were directly seeded onto MEF monolayer without stromal cell removal. The culture medium was DMEM medium that was supplemented with 0.1 mM β-mercaptoethanol (Gibco Invitrogen), 1% (v/v) nonessential amino acids (Gibco Invitrogen), 2 mM L-glutamine (Sigma-Aldrich), 1% (v/v) lyophilized mixture of penicillin and streptomycin (Gibco Invitrogen), 5,000 units/ml mouse LIF (Chemicon, Temecula, Calif.), and 15% (v/v) FBS (HyClone).

Coculture of MEFs and Ovarian Cells for Establishing Colony-Forming Cells

MEF monolayers were treated with 10 μg/ml mitomycin C (Sigma-Aldrich Corp.) for 3 h in gelatin-coated 60-mm tissue culture dishes and subsequently used for establishing colony-forming cells. The ovarian cells prepared were additionally seeded into the dishes that contained MEF monolayers and cultured at 37° C. under 5% $CO_2$ in a humidified air atmosphere. On day 4 of culture, the ovarian cells reached 60-70% of confluency were subsequently replated on a new monolayer in the same size culture dishes containing culture medium. The LIF concentration added to the culture medium ranged from 1,000 to 5,000 units/ml in primary culture and was fixed at 1,000 units/ml for the subcultures. At the end of the primary culture (on day 7 of culture), colony-forming cells were mechanically removed with a capillary pipette and subcultured with the MEF monolayer at intervals of 3 days, whereas the medium was changed daily.

Marker Staining of Colony-Forming Cells

For characterization using stem cell-specific markers, colony-forming cells collected at the 20$^{th}$ subpassage were fixed in 4% (v/v) formaldehyde (Sigma-Aldrich) at room temperature for 10 min. The reactivity of the colony-forming cells to alkaline phosphatase was assessed with Fast Red TR/naphthol AS-MX phosphate (Sigma-Aldrich). Antibodies against Oct-4 (BD Biosciences, San Jose, Calif.), stage-specific embryonic antigens (SSEA)-1 (Developmental Studies Hybridoma Bank, Iowa City, Iowa), SSEA-3 (Developmental Studies Hybridoma Bank), SSEA-4 (Developmental Studies Hybridoma Bank), integrin α6 (Santa Cruz Biotechnolgy, Santa Cruz, Calif.), integrin β1 (Santa Cruz Biotechnolgy), Vasa (Abcam, Cambridge, UK), Fragilis (Abcam) and AMH (Abcam) were provided for the marker staining. Localization of SSEA-1, SSEA-3, SSEA-4, Oct-4, integrin α6, integrin β1, Vasa, Fragilis and AMH was performed using the Alexa Fluor 488-conjugated anti-mouse antibody (Molecular Probes, Eugene, Oreg.), the Alexa Fluor 568-conjugated anti-mouse antibody (Molecular Probes), and the DakoCytomation kit (DakoCytomation, Carpinteria, Calif.).

In Vitro and In Vivo Differentiation

To confirm spontaneous differentiation in vitro, the colony-forming cells were treated with 0.04% (v/v) trypsin-EDTA (Gibco Invitrogen), and the dissociated cells were subsequently transferred to 100-mm plastic petri dishes that contained LIF-free DMEM (Gibco Invitrogen) that was supplemented with 10% (v/v) FBS (HyClone). The cells were grown until the embryoid bodies formed. The embryoid bodies were seeded separately into 4-well culture plates and cultured for 10 to 14 days. The embryoid bodies were stained with the following specific markers for the three germ layers: nestin (Santa Cruz Biotechnology) and S-100 (Abcam) for ectodermal cells; α-smooth muscle actin (Abcam) and desmin (Santa Cruz Biotechnology) for mesodermal cells; and α-fetoprotein (Biodesign International) and troma-1 (Hybridoma Bank) for endodermal cells. Antibody localization was performed with the DakoCytomation kit (DakoCytomation).

To confirm in vivo differentiation, $1\times10^7$ colony-forming cells retrieved at the 20$^{th}$ subpassage were injected subcutaneously into adult NOD-SCID mice. Teratomas that formed in the subcutaneous region were collected 6 weeks post-transplantation and fixed with 4% (v/v) paraformaldehyde (Sigma-Aldrich). After embedding in paraffin blocks, the tissues were stained with hematoxylin and eosin for examination under a phase-contrast microscope (BX51TF; Olympus, Kogaku, Japan).

Induction of Differentiation into Neuronal Cells

For in vitro differentiation into neuronal lineage cells, the colony-forming cells were dissociated and plated onto a 0.1% gelatin-coated plastic culture dish at a density of $0.5\text{-}1.5\times10^4$/cm$^2$ in modified N2B27 medium that consisted of DMEM/F12 (Gibco Invitrogen) supplemented with N2 (Gibco Invitrogen) and B27 (Gibco Invitrogen). Morphological evaluation was conducted throughout the culture period and the culture medium was changed at intervals of 2 days. Differentiated cells were maintained by replating into fibronectin-coated tissue culture dishes. Immunocytochemical analysis was conducted subsequently. Differentiated cells were fixed with 4% (v/w) paraformaldehyde (Sigma-Aldrich) for 5 min, incubated in blocking solution (PBS supplemented with 5% FBS), and the fixed cells were reacted with primary antibodies directed against nestin (Santa Cruz Biotechnology), β-tubulin type III (Chemicon), O4 (Chemicon), and glial fibrillary acidic protein (GFAP; Chemicon). The antigen-antibody complexes were visualized by reacting with the following fluorescent secondary antibodies: Alexa Fluor 488-conjugated anti-goat (Molecular Probes); Alexa Fluor 568-conjugated anti-mouse (Molecular Probes); and Alexa Fluor 488-conjugated anti-mouse (Molecular Probes). The stained cells were observed under a laser scanning confocal microscope with a krypton-argon mixed gas laser excitation at 488 nm or 568 nm and using the fluorescein filter (Bio-Rad, Hemel Hempstead, UK).

Primer Design

The Primary3 software (Whitehead Institute/MIT Center for Genome Research) was used to design all the specific primers used in these experiments. All the PCR primers were designed based on mouse cDNA and genomic DNA sequences obtained from GenBank. The specificities of the designed primers were tested by conducting 40 PCR cycles of 95° C. for 30 sec, the annealing temperature (shown in table S6) for 45 sec, and 72° C. for 30 sec. The primer sequences are listed in SI Table 1.

Reverse Transcriptase-PCR Analysis

Total RNA of the ovaries, brain, heart, lung, liver, stomach, spleen, small intestine, bladder, kidney and skin of C57BL/6 or B6D2F1, and colony-forming cells was extracted using the RNeasy Plus Mini Kit (Qiagen, Valencia, Calif.) according to the manufacturer's instructions. The cDNAs were synthesized from approximately 1 μg of total RNA using the Reverse Transcription System (Promega, Madison, Wis.) and subjected to PCR amplification with the specific primers. The PCR products were size-fractionated by 1.2% agarose gel electrophoresis and were visualized by ethidium bromide staining.

Real-Time PCR Analysis

Total RNA was extracted from the ovaries using the RNeasy Plus Mini Kit (Qiagen, Valencia, Calif.) according to the manufacturer's instructions. The cDNAs were synthesized by the same method used for RT-PCR. Subsequently, the expression levels of specific genes in the ovaries were quantified using the DyNAmo HS SYBRGreen qPCR Kit (Finnzymes, Espoo, Finland). PCR amplification was performed in a final volume of 25 μl with the ABI PRISM 7700 sequence detection system (Applied Biosystems, Foster, Calif.) and using the cycling parameters of 2 min at 50° C., 15 min at 95° C., followed by 40 cycles of 15 sec at 95° C., 30 sec at 60° C., and 30 sec at 72° C. The dissociation curve was recorded to check the PCR specificity. The final optimized concentration of each primer was 300 nM, and the absence of inter- and/or intra-molecular duplex formation between primers was confirmed in a control real-time PCR reaction that lacked template. The mRNA level of each gene in each sample was normalized to that of β-actin. The relative mRNA level was presented as $2^{-\Delta\Delta Ct}$, where Ct=the threshold cycle for target amplification, $\Delta Ct = Ct_{target\ gene} - Ct_{internal\ reference}$, and $\Delta\Delta Ct = \Delta Ct_{sample} - \Delta Ct_{calibrator}$.

Karyotyping and DNA Content Analysis by FACS

Karyotype of the cell lines was analyzed after they were maintained in culture for 7-8 weeks, which correspond to 16-18 passages. The cells were treated in culture medium supplemented with 0.05 μg/ml colcemid (Wako) for 1-2 h and were subsequently harvested for trypsinization. The cells were treated with 0.56% KCl solution for 15 min and fixed in a cold methano-acetic acid (3:1) mixture for 30 min on ice. The fixative solution was changed twice by centrifuging the cells at a 30 min interval. Chromosomes were spread onto heat-treated slides. A modified method of Seabright[14] was used for G-banding of air-dried chromosomes. The chromosome spread on glass slides was aged for about a week at room temperature, dipped in a 0.025% trypsin solution for 10 sec, rinsed in distilled water and stained with Giemsa's solution in phosphate buffer (pH 6.8) for 10 min. After being washed in distilled water and air-dried, at least 50 spreads were counted for chromosome number and 10 banding patterns were analyzed at 300-500 bands resolution.

For FACS analysis to measure DNA content, the harvested cells were washed in $Ca^{2+}$- and $Mg^{2+}$-free Dulbecco's PBS (DPBS; Gibco Invitrogen) and suspended in 70% (v/v) ethanol (Sigma-Aldrich) for 1 h at 4° C. The cells were centrifuged at 390×g for 4 min and resuspended in 0.5 ml of $Ca^{2+}$- and $Mg^{2+}$-free DPBS (Gibco Invitrogen) that contained 0.1 mg/ml ribonuclease (Sigma-Aldrich) and 0.1 mg/ml propidium iodide (Sigma-Aldrich). After 30 min at room temperature in the dark, the cell suspension was analyzed by a Becton Dickinson FACS-Vantage SE (Becton Dickinson, San Jose, Calif.) equipped with a two water-cooled laser. The data were analyzed using the CELL Quest™ ver. 3.3 software (Becton Dickinson).

Sex Determination by Genomic DNA-PCR Analysis

Total genomic DNA from each established stem cell line was extracted using the G-spin Genomic DNA Extraction Kit (iNtRON Biotechnology, Seoul, Korea) according to the manufacturer's instruction. The extracted genomic DNA was subjected to PCR amplification with primers for the Zfy1 (Y chromosome-specific) and Xist (X chromosome-specific) genes. The PCR products were size-fractionated by 1.2% agarose gel electrophoresis and visualized by ethidium bromide staining.

Telomerase Activity Assay

Telomerase activity was determined using the $TRAP_{EZE}$ Telomerase Detection Kit (Chemicon) according to manufacturer's instructions. The two established lines were analyzed at the $20^{th}$ subpassage and PCR amplification was conducted for 27 cycles. The PCR product was separated by electrophoresis in non-denaturing polyacrylamide gels.

DNA Microsatellite Analysis

DNA microsatellite analysis was performed with genomic DNA samples from B6D2F1 tail, ICR MEFs and two lines of newly established colony-forming cells. Two specific mouse microsatellite primers (D03Mit200 and D11Mit4) that were collected from public database (http://www.cidr.jhmi.edu/mouse/mmset.html) were used. The genomic DNA from each sample was amplified by PCR for the two microsatellite loci. Forward primers were synthesized with a fluorescent tag (TET or HEX) at the 5'-end, and fluorescent PCR amplification was performed with the PC808 program TEMP control system (ASTEC). The PCR products were subsequently analyzed in the ABI Prism 310 DNA automated sequencer (Applied Biosystems). Digital images were obtained using the Genescan Data Collection ver. 2.5 software (Applied Biosystems). Each fluorescent peak was quantified for base-pair size, peak height, and peak area.

Immunostaining of Ovarian Tissue-Dissociated Cells and Colony-Forming Cells

The dissociated ovarian, splenal or small intestinal cells were fixated in 70% ethanol for 1 h at 4° C. The fixed cells were centrifuged at 390×g for 4 min and washed twice with 0.5 ml of $Ca^{2+}$- and $Mg^{2+}$-free DPBS (Gibco Invitrogen) that contained 2% (v/v) FBS (HyClone). The fixed ovarian tissue-dissociated cells were reacted for 1 h at 4° C. with primary antibodies directed against Nanog (Abcam), Vasa, CD44 (Chemicon) or AMH and secondary reacted with Oct-4. Moreover, the colony-forming cells dissociated by 1 mM EDTA (BIONEER, Seoul, Korea) were reacted for 1 h at room temperature with primary antibodies to PE-conjugated Sca-1 (BD Biosciences), FITC-conjugated CD44 (BD Biosciences), biotin-conjugated CD34 (BD Biosciences) and biotin-conjugated CD45 (BD Biosciences). Sca-1 and CD44 were specific markers for mesenchymal stem cells, while CD34 and CD45 were used for epithelial stem cell-specific and hematopoietic stem cell-specific markers, respectively. After washing twice, the antigen-antibody complexes were visualized with the following fluorescent secondary antibodies: Alexa Fluor 488-conjugated anti-mouse (Molecular Probes), Alexa Fluor 488-conjugated anti-rabbit (Molecular Probes), Alexa Fluor 568-conjugated anti-mouse (Molecular Probes), Alexa Fluor 568-conjugated anti-rat (Molecular Probes), and Streptavidin-phycoerythrin (SAv-PE, BD Biosciences). The stained ovarian tissue-dissociated cells were observed under a laser scanning confocal microscope (Bio-Rad), and the stained colony-forming cells were analyzed by flow cytometry (FACSCALIBUR, Becton Dickinson).

Deposit of ESC-Like Cell

Of the ovarian cell-derived ESC-like cells showing all of the ES cell characteristics described above, one cell was named "OSC-B6D2-SNU-1" and deposited on Nov. 17, 2006 in the International Depository Authority, the Korean Cell Line Research Foundation and was given accession No. KCLRF-BP-00148.

Results

Figure 15A:
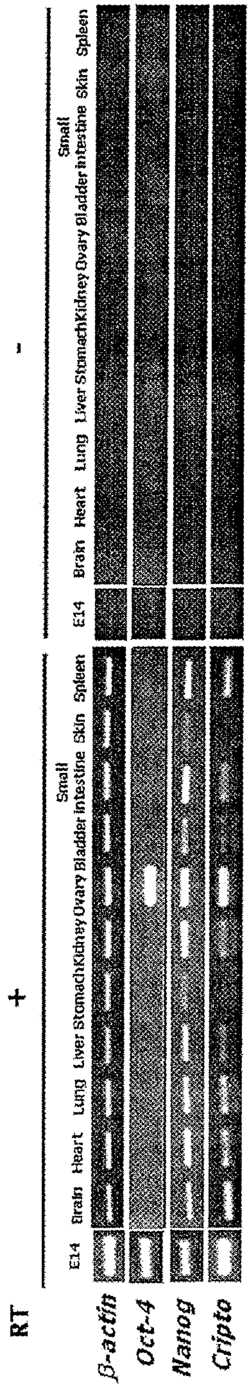
FIGS. 15*a*-15*b* show the expression of genes related to pluripotency in various tissues of adult mice.
Figure 15B:
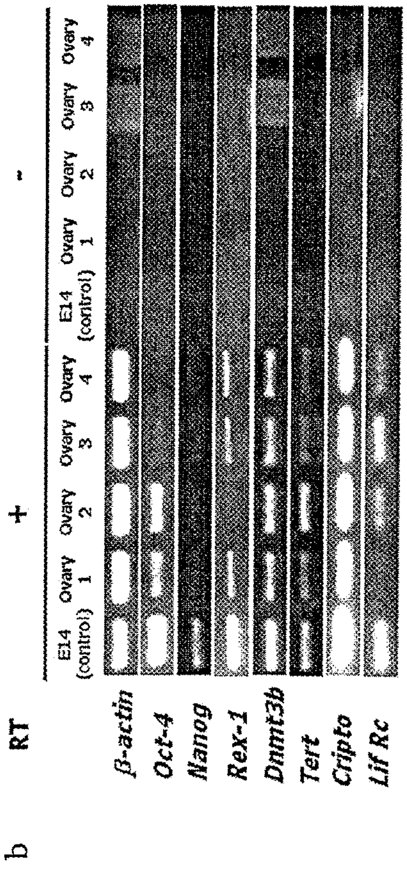

To find another source of the pluripotent cells in adult tissue, we monitored stem cell-specific gene expression (Oct-4, Nanog and Cripto) in the brain, heart, lung, liver, stomach, kidney, ovary, small intestine, skin, and spleen of 8-week-old, adult female mice. All organs expressed Nanog mRNA, which was confirmed by RT-PCR (primer sequences listed in Table 8), and most organs except for the stomach and skin expressed Cripto (FIG. 15).

TABLE 8

Oligonucleotide primers and PCR cycling conditions

| Genes | GenBank number | Primer sequence Sense (5' > 3') | Anti-sense (5' > 3') | Size (bp) | Temp (° C.) |
|---|---|---|---|---|---|
| β-actin (RT) | X03672 | ACCGTGAAAAGATGAC CCAG (SEQ ID NO: 1) | TCTCAGCTGTGGTGGTG AAG (SEQ ID NO: 2) | 254 | 60 |
| β-actin (R-T) | X03672 | TACCACAGGCATTGTGA TGG (SEQ ID NO: 3) | TCTTTGATGTCACGCACG ATT (SEQ ID NO: 4) | 200 | 60 |
| Oct-4 (RT, R-T) | M34381 | GAAGCCCTCCCTACAGC AGA (SEQ ID NO: 5) | CAGAGCAGTGACGGGAA CAG (SEQ ID NO: 6) | 297 | 60 |
| Nanog (RT, R-T) | AY455282 | CCCCACAAGCCTTGGAA TTA (SEQ ID NO: 7) | CTCAAATCCCAGCAACC ACA (SEQ ID NO: 8) | 255 | 60 |
| Rex-1 (RT) | M28382 | ACATCCTAACCCACGCA AAG (SEQ ID NO: 9) | TGATTTTCTGCCGTATGC AA (SEQ ID NO: 10) | 294 | 60 |
| Rex-1 (R-T) | M28382 | TCCCCGTGTAACATACA CCA (SEQ ID NO: 11) | CTTCGTCCCCTTTGTCAT GT (SEQ ID NO: 12) | 247 | 60 |
| Cripto (RT) | M87321 | CTTTAAGCAGGGAGGTG GTG (SEQ ID NO: 13) | TAAAGCCATCTGCCACA ATG (SEQ ID NO: 14) | 195 | 60 |
| Cripto (R-T) | M87321 | CGGAGATCTTGGCTGCT AAC (SEQ ID NO: 15) | CTTCGACGGCTCGTAAA AAC (SEQ ID NO: 16) | 200 | 60 |
| Dnmt3b (RT) | BC105922 | AGTCCATCGCTGTGGGA ACT (SEQ ID NO: 17) | GGGCGGGTATAATTCAGC AA (SEQ ID NO: 18) | 226 | 60 |
| Dnmt3b (R-T) | BC105922 | GTCCGGAAAATCACCAA GAA (SEQ ID NO: 19) | CCAGAAGAATGGACGGT TGT (SEQ ID NO: 20) | 201 | 60 |
| Tert (RT) | AF051911 | GGATCCTGGCTACGTTC CTG (SEQ ID NO: 21) | TGCCTGACCTCCTCTTGT GA (SEQ ID NO: 22) | 208 | 60 |
| Tert (R-T) | AF051911 | GCAGTGGTCCGGAGAGA TAG (SEQ ID NO: 23) | ACACTGTGACGCAGGAA GTG (SEQ ID NO: 24) | 224 | 60 |
| Lif Rc (RT, R-T) | BC031929 | GCTGAGTGGTAAAGATA CCG (SEQ ID NO: 25) | TTCGTTGGACTCATACAA CA (SEQ ID NO: 26) | 261 | 60 |
| Stat3 (RT) | AY299489 | TTTGGAATGAAGGGTAC ATC (SEQ ID NO: 27) | CAAATGACATGTTGTTCA GC (SEQ ID NO: 28) | 228 | 60 |
| Bmp4 (RT) | BC013459 | TGAGAGACCCCAGCCTA AGA (SEQ ID NO: 29) | AAACTTGCTGGAAAGGC TCA (SEQ ID NO: 30) | 259 | 60 |
| Fgf4 (RT) | BC104312 | CAGTCTTCTGGAGCTCT CTC (SEQ ID NO: 31) | AGGAAGTGGGTTACCTT CAT (SEQ ID NO: 32) | 282 | 60 |
| Foxd3 (RT) | AF067421 | CAAGAACAGCCTGGTG AAG (SEQ ID NO: 33) | GTCCAGGGTCCAGTAGT TG (SEQ ID NO: 34) | 262 | 60 |
| Sox2 (RT) | AB108673 | ACGCTCATGAAGAAGGA TAA (SEQ ID NO: 35) | GTAGGACATGCTGTAGG TGG (SEQ ID NO: 36) | 345 | 60 |
| CD9 (RT) | U60473 | ATGCTACCACTGTTTCC AAC (SEQ ID NO: 37) | ACAAGTTAAACTGGCAG CAT (SEQ ID NO: 38) | 212 | 60 |
| Gdf3 (RT) | BC101963 | CGAGTTTCAAGACTCTG ACC (SEQ ID NO: 39) | TAGAGGACCTTCTGGAG ACA (SEQ ID NO: 40) | 276 | 60 |
| Zfy1 (gDNA) | AC163622 | GTTACTCATTTTCAGGT GTTCTGGG (SEQ ID NO: 41) | GTGTCAGCTGTTATAGGATC AGTGA (SEQ ID NO: 42) | 572 | 62 |
| Xist (gDNA) | AJ421479.1 | GAGATACATTTATTTGCT CA (SEQ ID NO: 43) | GACTTAGTTTGGTTTCTT TA (SEQ ID NO: 44) | 540 | 55 |

RT = Reverse Transcriptase Polymerase Chain Reaction, R-T = Real-Time Polymerase Chain Reaction, gDNA = genomic DNA Polymerase Chain Reaction.

Figure 16:
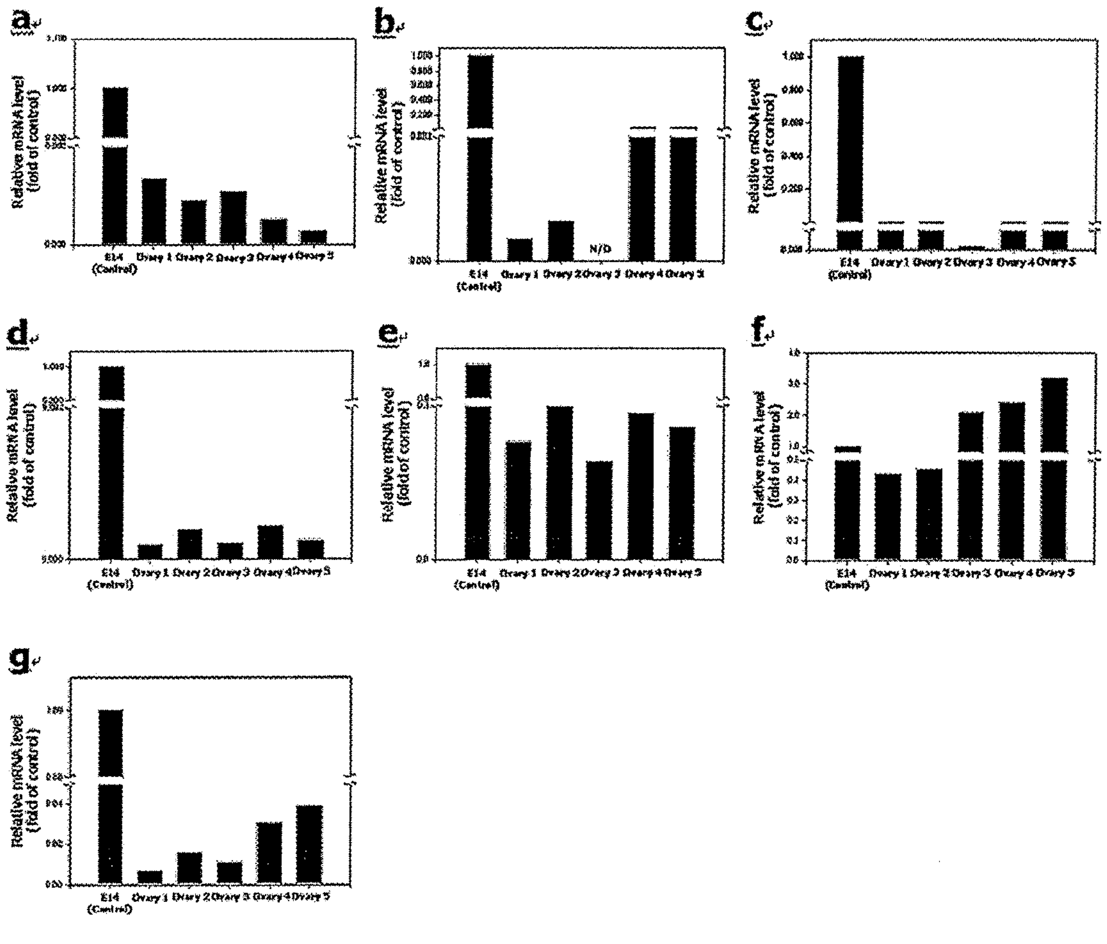
FIG. 16 represents quantification of pluripotency-specific gene expression in mouse ovaries retrieved from different animals. The expression levels of the Oct-4 (a), Nanog (b), Rex-1 (c), Cripto (d), Tert (e), Lif Rc (f), and Dnmt3b (g) genes in the ovaries retrieved from different mice were measured by real-time PCR. E14 embryonic stem cells were used as the positive control cells. Different levels of gene expression are detected among the ovaries examined. N/D, not detected.

However, the expression of Oct-4 was detected only in the ovary, small intestine and spleen. In addition to Oct-4, Nanog and Cripto, ovarian tissue further expressed the Rex-1, Dnmt3b, Tert, and Lif Rc genes. Their expression levels, however, were different among the ovaries examined and Nanog expression was even negligible in one ovary (FIG. 16).

Figure 17:
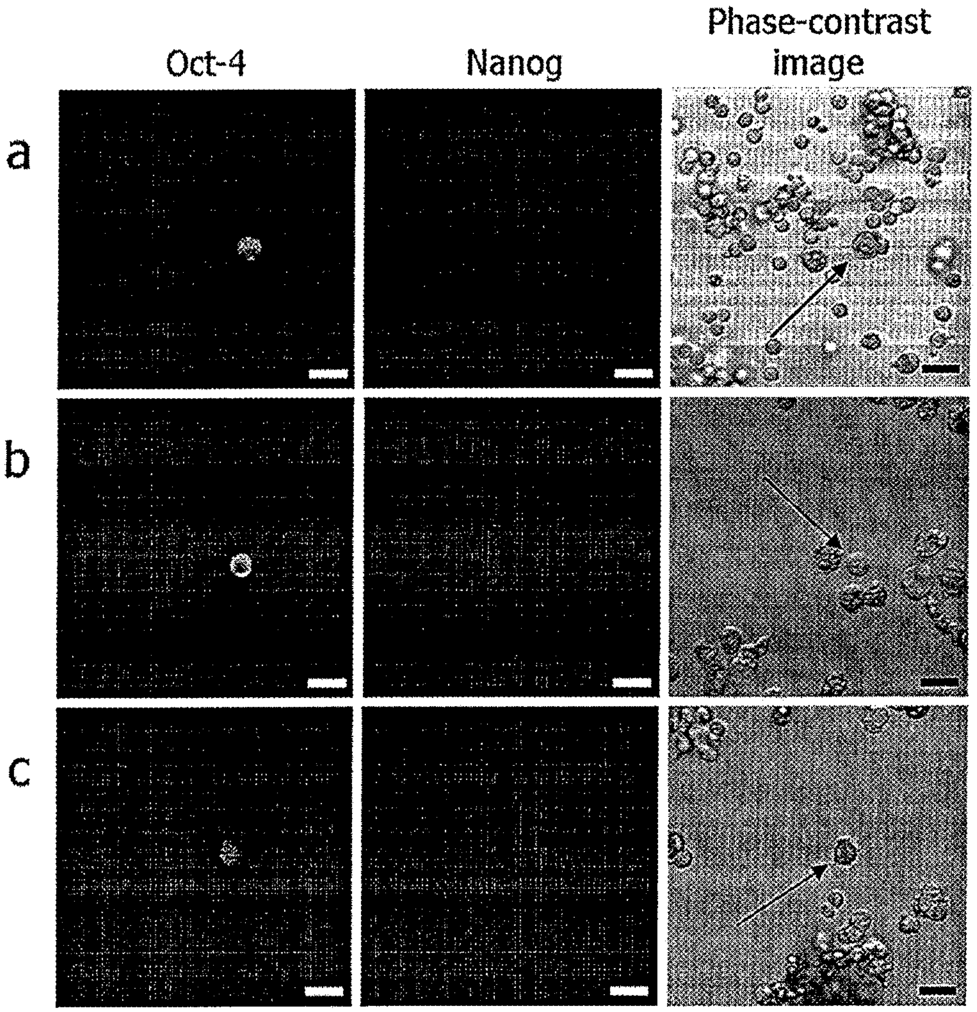
FIG. 17 shows immunostaining results of the cells dissociated from the spleen (a), small intestine (b) and ovary (c) with stem cell-specific, Oct-4 and Nanog. Cells of each organ were dissociated with enzyme treatment and the 1×103 dissociated cells were subsequently stained with anti-Oct-4 (green fluorescence) or anti-Nanog (red fluorescence) antibody. Confocal microscope image show that there are Oct-4-positive cells in splenic and small intestinal cells, while no Nanog-positive cells are found. There are the ovarian cells positively concomitantly stained with Oct-4 and Nanog. Phase-contrast image show that the Oct-4- and Nanog-positive cells (arrows) are mixed with several types of cells. Scale bar=20 μm.

A very few of Oct-4-positive cells were dissociated from the spleen and small intestine, but they were negative for Nanog (FIG. 17). These results demonstrated that Nanog mRNA was not translated in these tissues. In contrast, the cells dissociated from the ovary were positive for both Oct-4 and Nanog. Subsequently, we dissociated small intestinal, splenal and ovarian cells by collagenase I and trypsin treatments and cultured them on mouse embryonic fibroblast (MEF) monolayer with or without mitomycin-C treatment in Dulbecco's minimal essential medium (DMEM)-based medium containing β-mercaptoethanol, non-essential amino acids, L-glutamine, fetal bovine serum and antibiotics, to which 1,000, 2,000 or 5,000 units/ml leukemia inhibitory factor (LIF) was added. Splenal and small intestinal cells dominantly consisted of fibroblasts and only formed homogenous monolayer without colony-formation, regardless of LIF concentrations. As the control, culture of MEFs alone in the same medium did not yield colonies.

Figure 18:
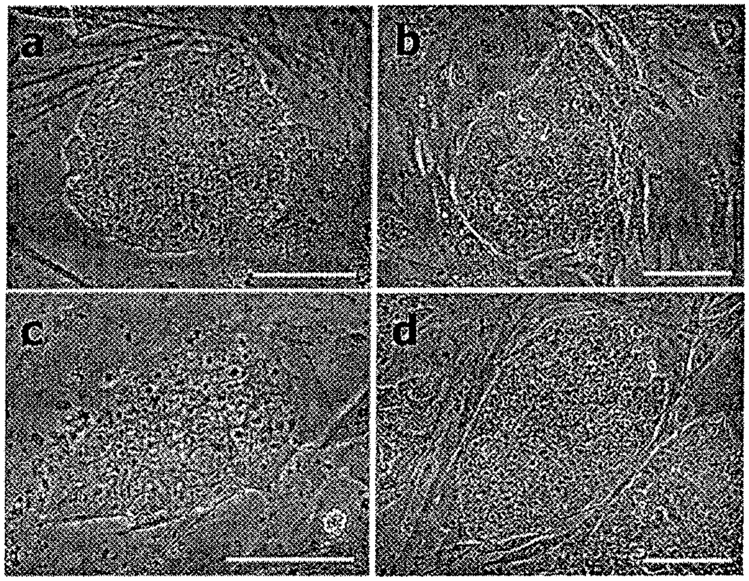
FIG. 18 shows morphology of colony-forming cells derived from the coculturing of adult ovarian cells and embryonic fibroblasts in mice. a, E14 embryonic stem cells. b, Colony-forming cells on day 7 of primary culture. Colony-forming cells after ten subpassages (day 37 of culture; c) and after 20 subpassages (day 76 of culture; d). Scale bar=50 μm.

In the case of the ovarian cell culture, dissociated cells were further filtered through a cell strainer before culture for removing immature, maturing and mature oocytes, and most preantral and antral follicles of more than 40-μm in diameter. To further remove stromal cells mixed in the dissociated cells, the buoyant cells above the bottomed cells were collected 30 min after seeding and reseeded on the MEF monolayer. Colony-like cell aggregation was observed during primary culture, while MEF-free culture did not yield the colony-formation. The same technique was applied for culturing splenal and small intestinal cells, but failed to yield colonies. Two of 14 trials gave colonies until day 7 of primary culture and all cases of the establishment were observed only after culture in high dose (5,000 units/ml) LIF-containing medium. The colony-forming cells were morphologically typical of embryonic stem (ES) cells or cultured epiblast cells (FIG. 18), which have stably been maintained for more than 3 months with 25 passages.

To trace the origin of colony-forming cells, short-tandem repeat (STR) microsatellite analysis using two markers was undertaken. The genotypes of two lines established (OSC-B6D2-SNU-1 and OSC-B6D2-SNU-2), the ovarian cell donor (B6D2F1; C57BL/6×DBA2) and the feeder fibroblasts (ICR) were compared. The microsatellite loci of the established cells were exactly matched with those of the ovary donor, while completely different from those of the fibroblast donors (Table 9).

TABLE 9

Short-tandom repeat microsatellite analysis of established colony-forming cells derived from the coculturing ovarian cells and embryonic fibroblast feeder, and the strains of the ovary (B6D2F1) and feeder cell (ICR) donor

| Sample | Size 1 | Size 2 |
|---|---|---|
| D3Mit200[a] | | |
| Ovary donor | 101.09 | 124.22 |
| Feeder cell | 124.24 | 126.21 |
| OSC-B6D2-SNU-1 | 100.96 | 124.11 |
| OSC-B6D2-SNU-2 | 100.95 | 124.19 |
| D11Mit4[a] | | |
| Ovary donor | 248.92 | 285.39 |
| Feeder cell | 242.8 | 248.98 |
| OSC-B6D2-SNU-1 | 248.97 | 285.44 |
| OSC-B6D2-SNU-2 | 249.07 | 285.53 |

[a]Microsatellite markers used were selected from MIT database for discerning mouse strains employed as ovary donor (B6D2F1) and feeder cells (ICR).

Figure 19:
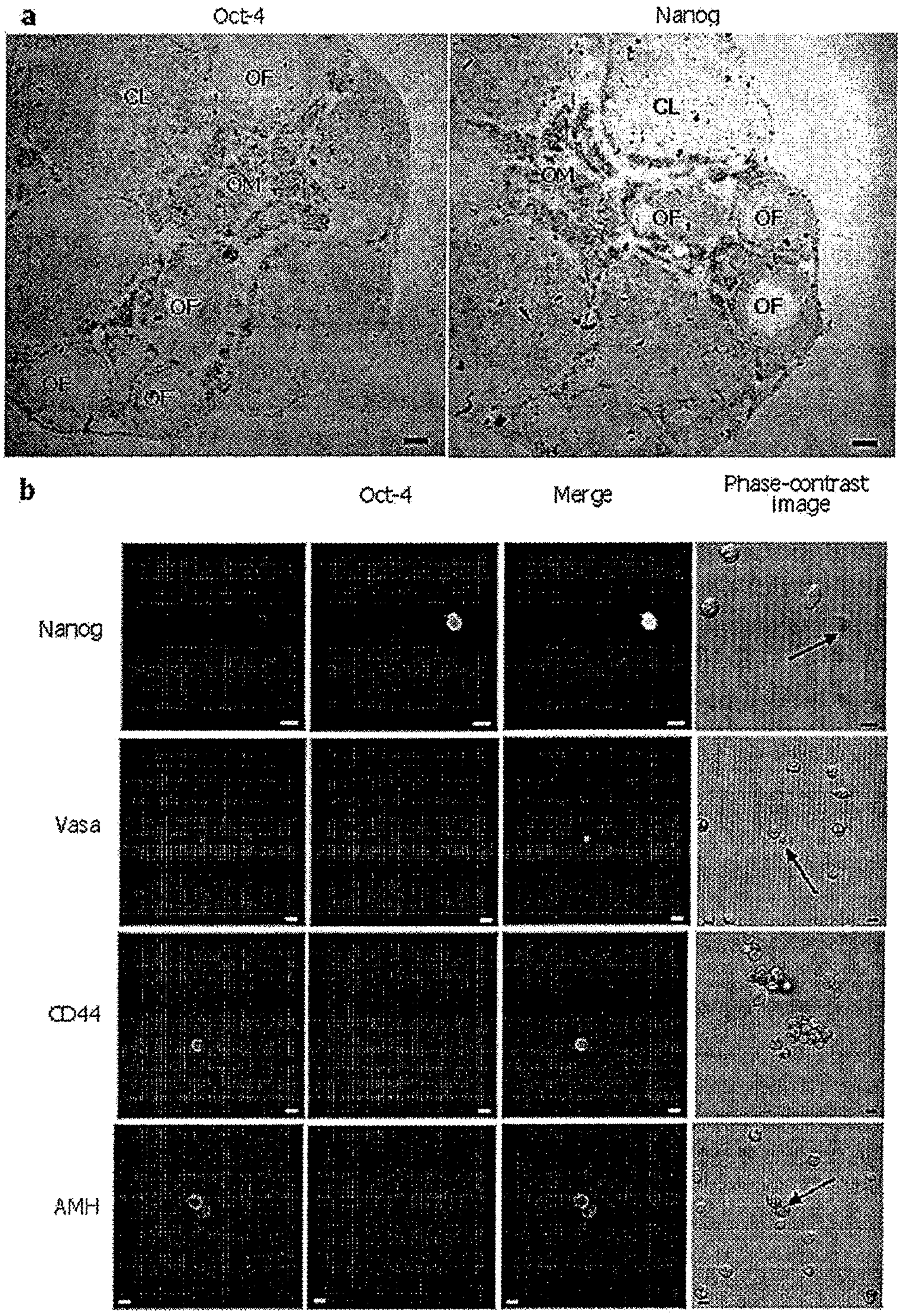
FIG. 19 represents in situ hybridization of adult ovarian tissue for the detection of Oct-4 and Nanog mRNA expression, and double immunostaining of stem cell-specific Nanog, germ cell-specific Vasa, follicle cell-specific AMH (anti-mullerian hormone) or mesenchymal cell-specific CD44 positive ovarian tissue-dissociated cells with Oct-4. (a) Image of ovarian tissue after in situ hybridization. The ovaries retrieved from 8-week-old, F1 hybrid mice were provided for the hybridization using Oct-4- and Nanog-specific mRNA probes. Oct-4 and Nanog mRNA expression is evident in the ovarian medullae (OM), while the peripheral (theca cell) region of ovarian follicles (OF) with various sizes also shows the mRNA expression. (CL) corpus luteum. Scale bar=100 μm. (b) Ovarian cells were double-immunostained immediately after dissociation. Nanog-, Vasa- or CD44-positive cells are concomitantly immunustained with anti-Oct-4 antibody, while AMH-positive cells are not positive for Oct-4. Phase-contrast image of Nanog-, Vasa-, CD44- or AMH-positive cells (arrows) shows that the vasa-positive cells are smaller than other cells. Scale bar=10 μm.

Next, in situ-hybridization of ovarian tissue was conducted and strong expression of stem cell-specific, Oct-4 and Nanog mRNA expression was detected predominantly in ovarian medulla and at the thin layer of the peripheral region in preantral and antral follicles. Subsequently, dissociated ovarian cells after stromal cell removal were double stained with Nanog, Vasa (germ cell-specific), AMH (follicle cell-specific) or CD44 (mesenchymal cell-specific) and Oct-4. Nanog-, Vasa- or CD44-positive cells were concomitantly positive for Oct-4, while AMH-positive cells did not react with Oct-4. The positive cells were round-type with either fine or coarse marginal line. However, the Vasa-positive cells were prominently smaller than others and colony-forming cells (FIG. 19).

Figure 20A:
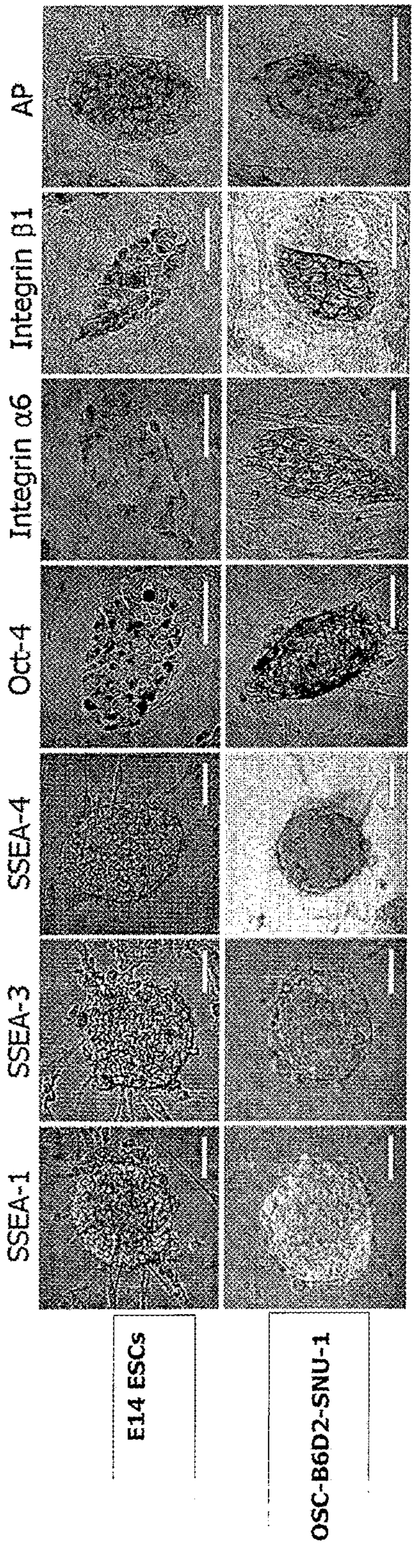
FIG. 20 represents the characterization of colony-forming cells derived from the coculturing of adult ovarian cells and embryonic fibroblasts in mice. a, Characterization using embryonic stem cell (ESC)-specific markers. Antibodies against stage-specific embryonic antigen (SSEA)-1, SSEA-3, and SSEA-4, and Oct-4, integrin α6, and integrin β1, as well as alkaline phosphatase (AP) were used for the characterization, and the E14 ESC line was employed as the positive control. Similar to the E14 ESCs, the colony-forming cells are positive for SSEA-1, Oct-4, integrin α6, integrin β1, and AP. However, both the E14 ESCs and the established cells are negative for SSEA-3 and the SSEA-4. Scale bar=50 μm. b, Pluripotent cell-specific gene expression of the E14 ESCs and the colony-forming cells was monitored by RT-PCR and similar gene expression was detected. Both lines established were characterized, but the image from OSC-B6D2-SNU-1 is depicted on behalf of the established cells.
Figure 20B:
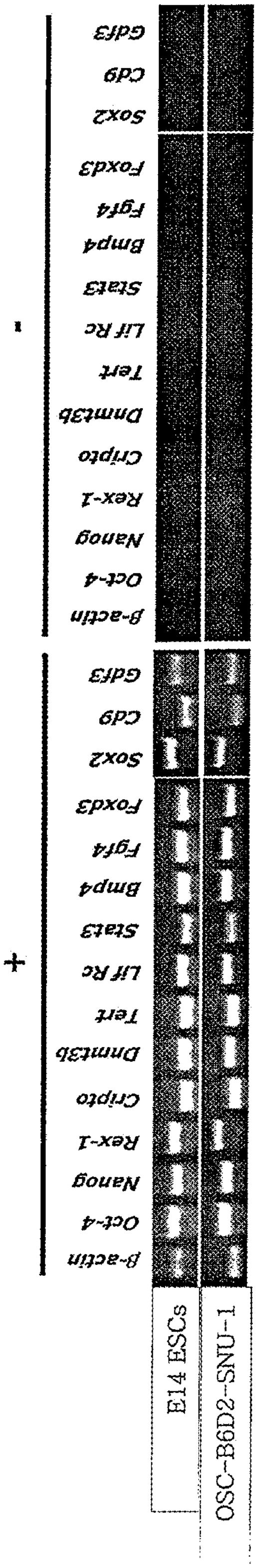
Figure 21:
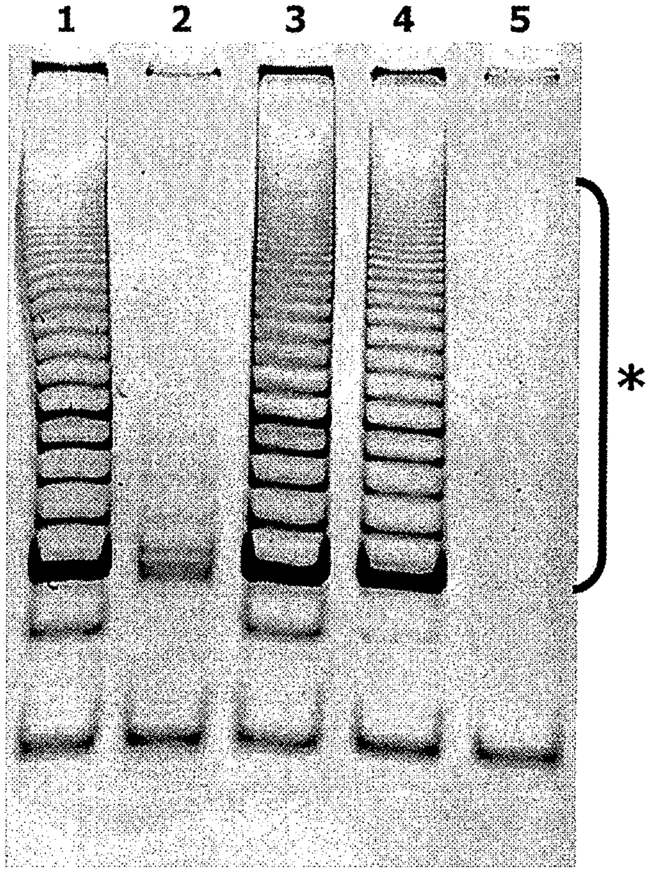
FIG. 21 represents telomerase activities of colony-forming cells detected by the telomeric repeat amplification protocol assay. Two cell lines were evaluated. The ladder of telomerase products amplified by PCR was shown with six-base increments starting at 50 nucleotides at the portion indicated by the asterisk. All of the cell lines express high levels of telomerase activity. Lane 1, positive control (E14 embryonic stem cells); lane 2, MEFs; lanes 3-4, colony-forming cells of OSC-B6D2-SNU-1 and OSC-B6D2-SNU-2, respectively; lane 5, PCR control without the addition of template, respectively.
Figure 22:
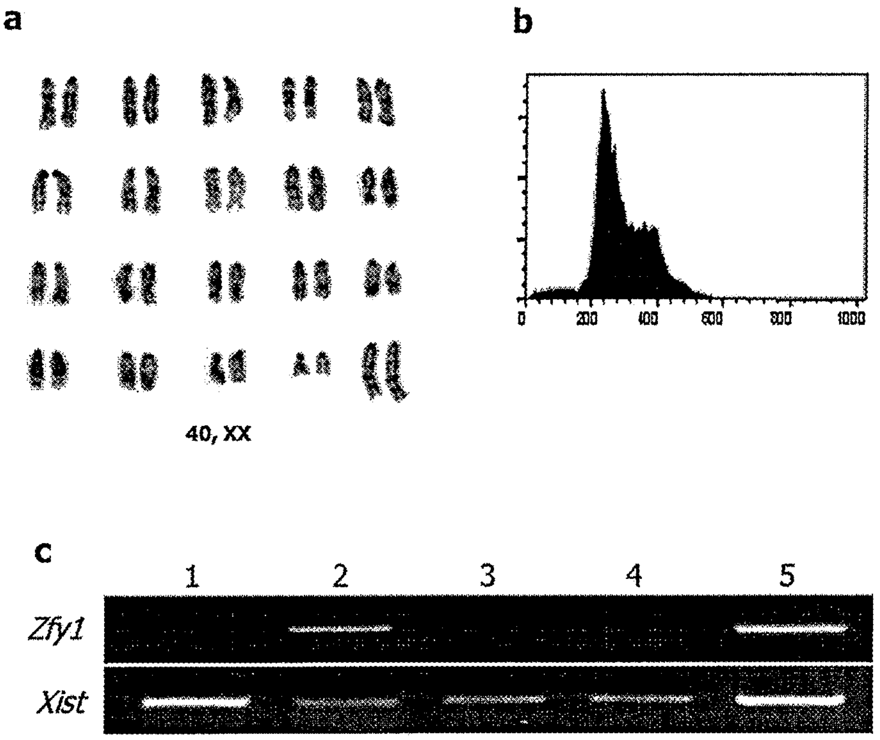
FIG. 22 represents karyotyping and sexing of the established colony-forming cells. G-banding of air-dried chromosomes in the established colony-forming cells were undertaken for exact karyotyping (a) and the population of diploid cells were estimated with a flow cytometry (b). In a and b, the image from OSC-B6D2-SNU-1 is depicted on behalf of the established lines. PCR analysis was further conducted using the X chromosome-specific Xist and Y chromosome-specific Zfy primers (c; Lane 1, tail cells with XX; lane 2, neonatal skin fibroblast with XY; lane 3, established OSC-B6D2-SNU-1; lane 4, OSC-B6D2-SNU-2; lane 5, testis cells). Diploidy is detected in both established lines and both two lines express the X chromosome-specific Xist gene but not the Zfy gene.
Figure 23:
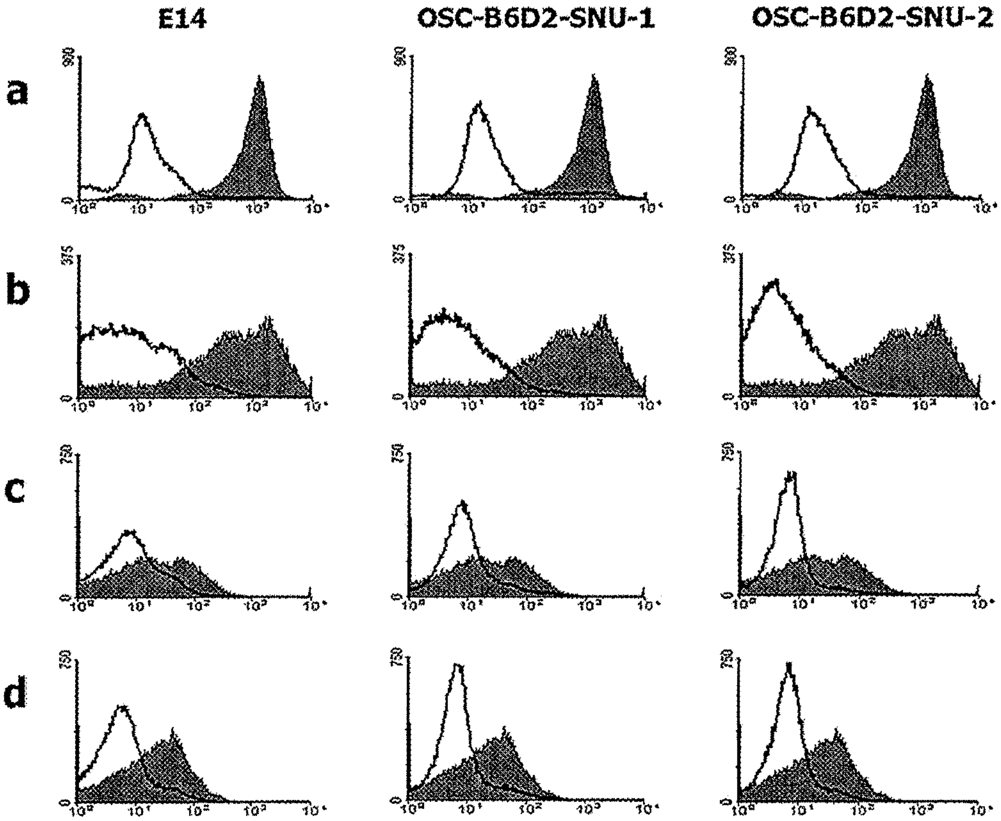
FIG. 23 shows characterization of colony-forming cells by fluorescence activated cell sorting (FACS) using mesenchymal stem cell (MSC)-specific marker CD44 (a) and Sca-1 (b), epithelial stem cell-specific marker CD34 (c) and hematopoietic stem cell-specific marker CD45 (d). The green color represented peaks of MSCs used as the control. E14 embryonic stem cells and established colony-forming cells are all negative for anti-CD44, anti-Sca-1, anti-CD34 and anti-CD45 antibodies.
Figure 24:
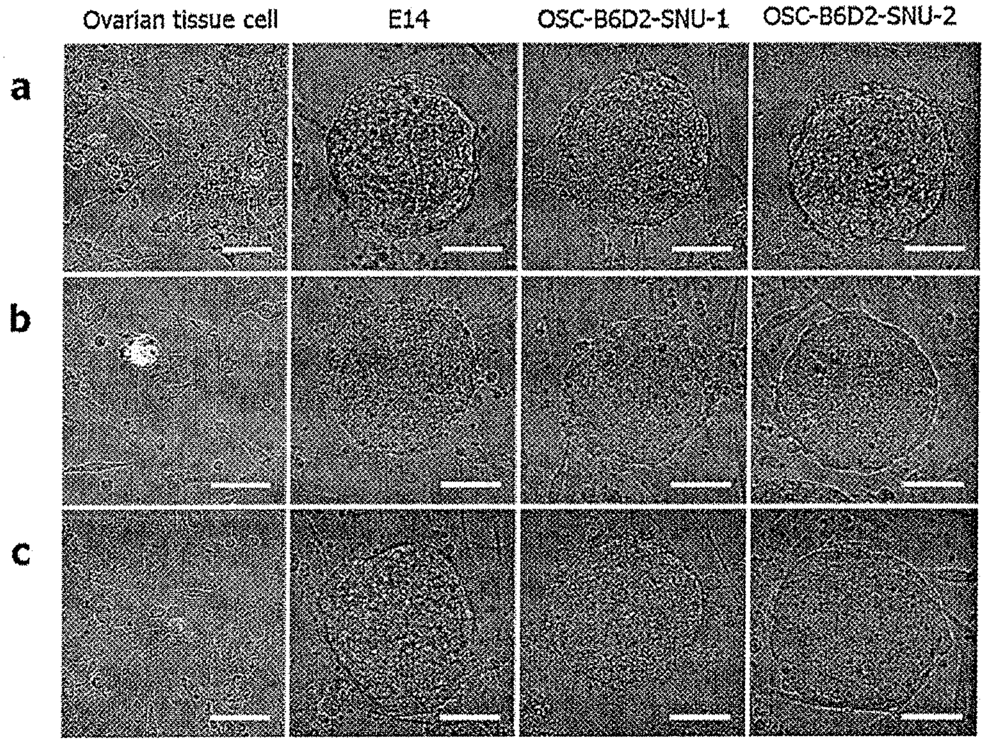
FIG. 24 shows immunostaining results of colony-forming cells with the germ cell-specific markers Vasa and Fragilis, and with the follicular cell-specific marker AMH. Two lines of colony-forming cells were provided for the staining and the ovarian cells before seeding and E14 embryonic stem cells (ESCs) were provided as the control cells. There are the cells positive for Vasa (a), Fragilis (b) or AMH (c) staining in the ovarian cells, while the colony-forming cells retrieved at the twentieth subpassage and E14 ESCs are not positive for those markers. Scale bar=50 μm.

The colony-forming cells subpassaged twenty times were positive for alkaline phosphatase, anti-stage specific embryonic antigen (SSEA)-1, anti-integrin α6, anti-integrin β1 and Oct-4 antibodies staining, whereas no reactivity to anti-SSEA-3 or anti-SSEA-4 antibodies was detected (FIG. 20). The stem cell-specific Oct-4, Nanog, Rex-1, Cripto, Dnmt3b, Tert, LifRc, Stat3, Bmp4, Fgf4, Foxd3, Sox2, CD9, and Gdf3 genes were also expressed and telomerase activity was detected in both lines established (FIG. 21). They had diploid karyotype with XX sex chromosome, which was determined by G-banding of air-dried chromosome, fluorescent-activated cell sorting (FACS) using a flow cytometry and PCR analysis using X chromosome-specific Xist and Y chromosome-specific Zfy1 gene primers (FIG. 22). Neither the established cells nor the referenced E14 ES cells were positive for tissue-specific stem cell markers (Sca-1 and CD44 for mesenchymal stem cell, CD34 for epithelial stem cell and CD45 for hematopoietic stem cell, Fragilis and Vasa for germline stem cell) and AMH (FIGS. 23-24).

Figure 25:
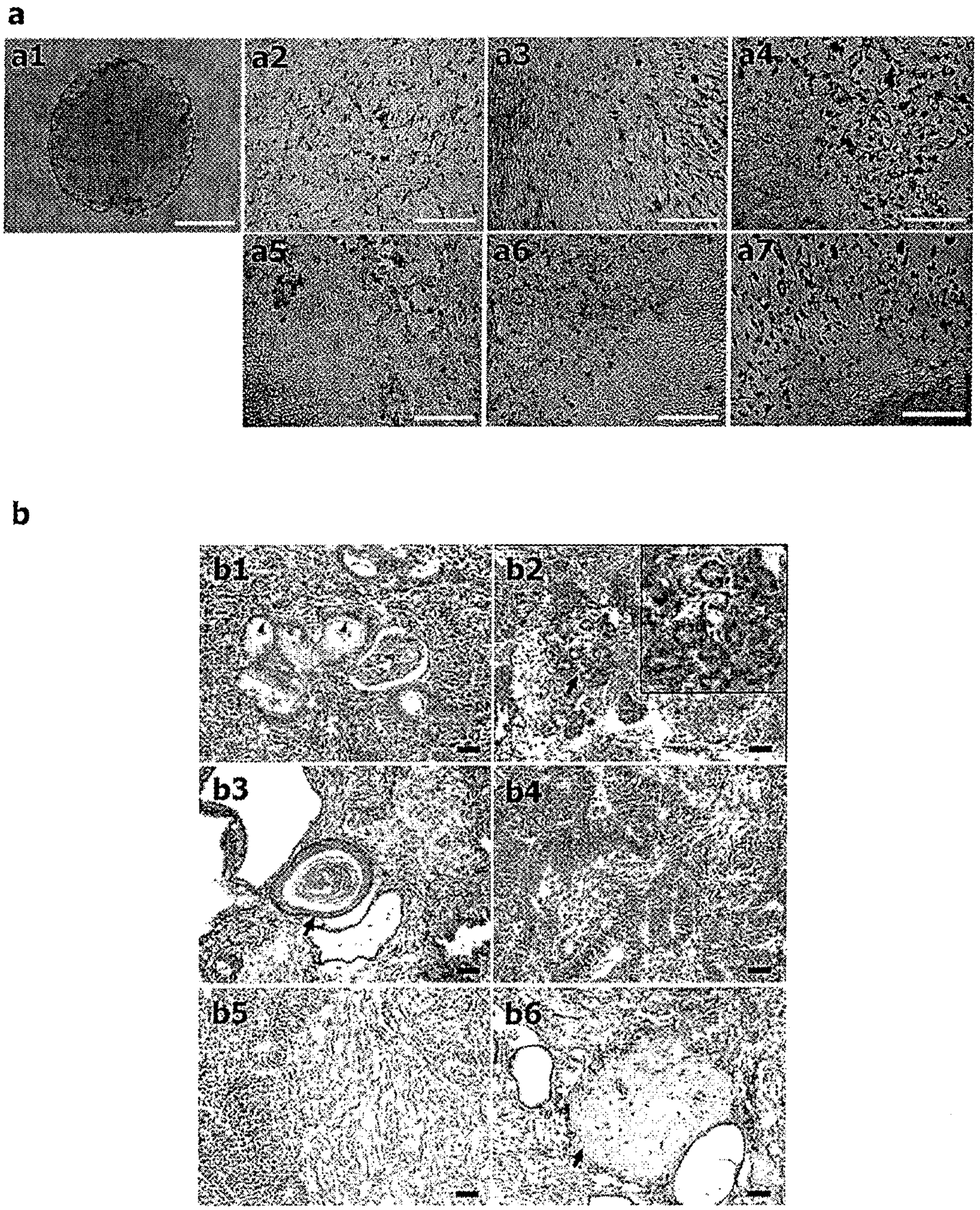
FIG. 25 represents spontaneous differentiation of colony-forming cells in vitro and in vivo. a, In vitro-differentiation of colony-forming cells into embryoid bodies (EBs) by culturing in leukemia inhibitory factor free-culture medium. (a1) EBs observed on day 4 of culture. Immunocytochemistry of EBs was undertaken to detect three germ layer-specific differentiation using the specific markers of S-100 (a2; ectodermal), nestin (a3; ectodermal), smooth muscle actin (a4; mesodermal), Desmin (a5; mesodermal), α-fetoprotein (a6; endodermal), and Troma-1 (a7; endodermal-specific). Scale bar=100 μm. b, In vivo differentiation of colony-forming cells by subcutaneous transplantation into NOD-SCID mice. The teratoma contained (b1) endodermal, glandular epithelium-Goblet cell like (arrow head), (b2) endodermal, exocrine pancreas, (b3) ectodermal, stratified squamous epithelium (arrow), (b4) ectodermal, neuroepithelial rossettes, (b5) mesodermal, skeletal muscle bundles, and (b6) mesodermal, bone tissue (arrow). Scale bar=50 μm. Both lines established were characterized, but the image from OSC-B6D2-SNU-1 is depicted on behalf of the established cells.
Figure 26:
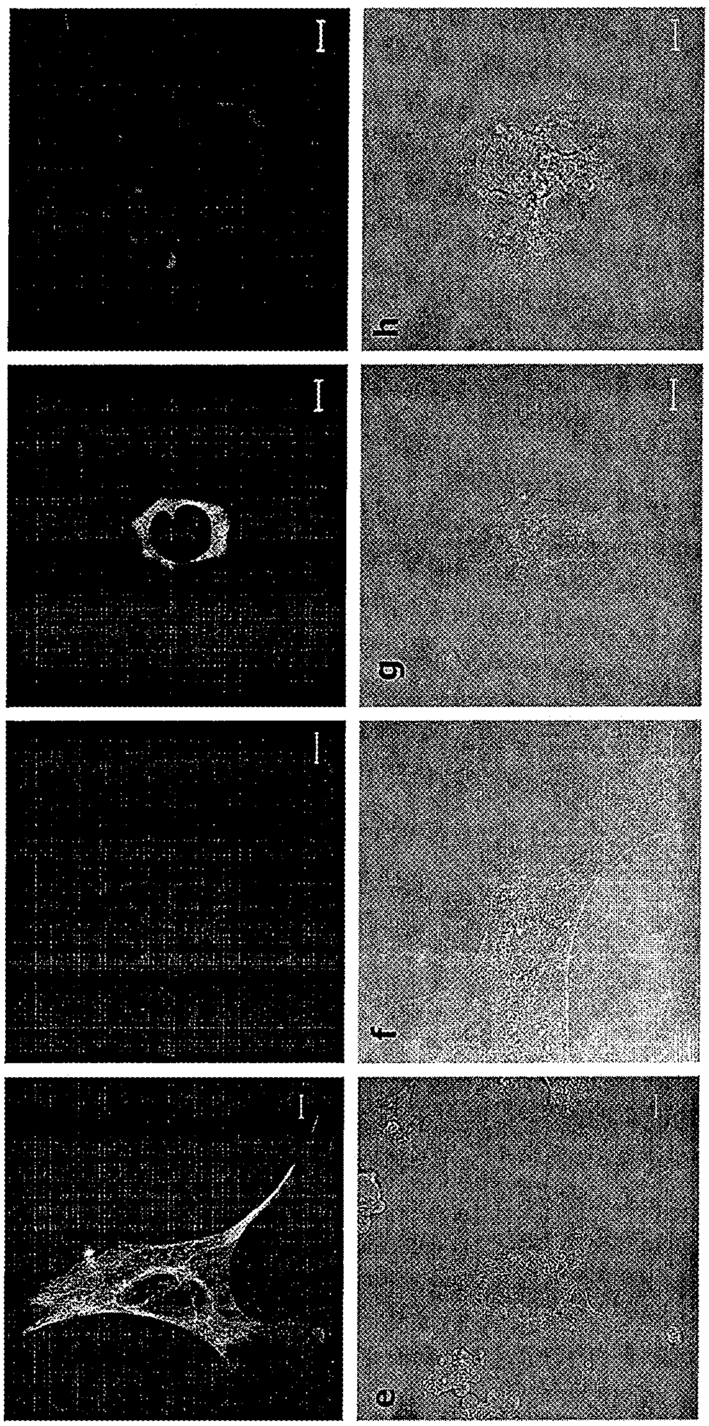
FIG. 26 represents neuronal cell differentiation of colony-forming cells derived from the coculturing of adult ovarian cells and embryonic fibroblasts in mice. a, Nestin-positive and b, Tuj1-positive neurons generated 14 days after replating on fibronectin. c, O4-positive oligodendrocyte generated 8 days and (d) GFAP-positive astrocytes generated 15 days after the replating. e-h, Phase contrast images of differentiated colony-forming cells into nestin-positive neurons, O4-positive oligodendrocyte and GFAP-positive astrocyte in modified N2B27 medium, respectively. Both lines established were provided for neuronal cell differentiation, but the image from OSC-B6D2-SNU-1 is depicted on behalf of the established cells (Scale bar=10 μm).

After culture in LIF-free medium, the cells formed embryoid bodies (FIG. 25) consisted of the cells being positive for markers of three germ layers (S-100, Nestin, α-smooth muscle actin, desmin, α-fetoprotein and troma-1). After being subcutaneously transplanted into NOD-SCID mice, the colony-forming cells formed teratomas consisting of cells derived from three germ layers (neuroepithelial rosettes, keratinized stratified squamous epithelial cells, osteoid island showing bony differentiation, muscle, pancreatic tissue, and ciliated columnar epithelial cells for OSC-B6D2-SNU-1 represented in FIG. 25). The colony-forming cells further differentiated into neuronal cells (neuron, oligodendrocyte and astrocyte) in an inducible manner after being treated with N2B27 solution (FIG. 26). These results show the established have ES cell (ESC)-like activity.

We are now undertaking a final set of experiment to confirm the pluripotency of the established cells by producing germline chimeras, which will be further expanded into a full-scale experiment with using EGFP-transfected cells (unpublished data). To date, we have had one delivery after transfer of embryos being aggregated with the colony-forming cells (OSC-B6D2-SNU-1) retrieved at the 11th subpassage and among 4 live offsprings, one was somatic chimera.

From these series of results, the colony-forming, ESC-like cells established are derived from ovarian cells not derived from feeder fibroblasts. Immunohistochemical analysis raised the possibility that germline cells (germ cells and parthenogenetic oocytes), follicular cells or mesenchymal cells will be the progenitor cells of the established cells. We however exclude germline cells and follicular cells as the progenitor cell and carefully consider the mesenchymal (stem) cells as the progenitor cells. Dissociation procedure consisting of cell strainer filtration can completely eliminate maturing oocytes that are able to be parthenogenetically activated and growing follicles of more than 40 μm in diameter. Removing stromal cells and other 'sticky' cells before seeding minimizes the chance that epithelial or hematopoietic stem cells involve in the establishment. This assumption is further supported by morphological difference between germline cell-marker positive cells (apparently smaller) and colony-forming cells and insensitivity of AMH-positive cells to stem cell-specific marker. The established cells were negative for germline stem cell-specific markers as early as they began colony formation and had strong telomerase expression. Probably, the 'dormant' mesenchymal (stem) cells in the ovary acquire cell plasticity or self-renewal activity, when they expose to certain extraordinal environment.

It is apparent that fibroblasts play an important role in establishing ovarian ESC-like cells. They may create appropriate niche (e.g. triggering cell-to-cell interaction or secreting critical molecule for acquiring pluripotency) for mobilizing the 'dormant' stem cells. From different viewpoints, we employed extremely high dose (5,000 units/ml) LIF for the establishment, which would appeal the importance of culture medium to create/regulate micro-environment for establishing tissue-derived ESC-like cells. In other set of experiment using different ESC-like cell lines, we found that an increase in Wnt signaling can be triggered by exposure to glutathione, which stimulated stem cell establishment and maintenance (data not shown).

It is possible that multipotent adult progenitor cells (MAPCs) in circulatory blood are the progenitors of ovarian ESC-like cells. We have not developed an experimental strategy to determine the progenitor cell of the ESC-like cells between two mesenchymal cells (pluripotent stem cells or MAPCs). However, we hardly consider MAPCs as the progenitor cells, because of tissue specific derivation of the colony-forming cells only from the ovaries, and of strong Oct-4 and Nanog expression in ovarian medulla (FIG. 19). In fact, most circulatory blood in the ovaries is removed during ovarian cell preparation. If MAPCs is the progenitor of the colony-forming cells, we will have another chance to derive tissue-specific ESC-like cells from various organs. We may derive tissue-specific pluripotent cells by changing culture environment or medium supplements, while the pluripotent cells can be established by activating mRNA translation of stem cell-specific genes in certain somatic cells (FIG. 17).

Our findings present the possibility of establishing autologous pluripotent cells from adult human organs without undertaking SCNT and without using embryos and even gametes, which contribute to overcoming the current limitations of ES cell research. Apparently, this newly-suggested alternative for deriving immune-specific pluripotent cells can avoid ethical dispute on undertaking cell/tissue therapy. Cellular and genetic evaluation of the established cells, and comparison between adult tissue-derived ES cells with embryo-derived pluripotent cells can provide numerous cues for further developing novel cell and tissue therapy.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Jiang, Y. et al. Pluripotency of mesenchymal stem cells derived from adult marrow. *Nature* 418, 41-49 (2002).
2. Szilvassy, S. J. The biology of hematopoietic stem cells. *Arch. Med. Res.* 34, 446-460 (2003).
3. Kanatsu-Shinohara, M. et al. Generation of pluripotent stem cells from neonatal mouse testis. *Cell* 119, 1001-1012 (2004).
4. Guan, K. et al. Pluripotency of spermatogonial stem cells from adult mouse testis. *Nature* 440, 1199-1203 (2006).
5. Takahashi K & Yamanaka S. Induction of pluripotent stem cells from mouse embryonic and adult fibroblast culture by defined factor. *Cell* 126, 663-676 (2006).
6. Pearson, H. & Abbot, A. Stem cells derived from 'dead' human embryo. *Nature* 443, 376-377 (2006).
7. Lee, O. K. et al. Isolation of multipotent mesenchymal stem cells from umbilical cord blood. *Blood* 103, 1669 (2004).
8. Toma, J. G. et al. Isolation of multipotent adult stem cells from the dermis of mammalian skin. *Nat. Cell Biol.* 3, 778 (2001).
9. Vrana, K. E. et al. Nonhuman primate parthenogenetic stem cells. *Proc. Natl. Acad. Sci. USA* 100, 11911-11916 (2003).
10. Cibelli, J. B. et al. Parthenogenetic stem cells in nonhuman primates. Science 295, 819 (2002).
11. Johnson, 1, Canning, J., Kaneko T., Pru, J. K. & Tilly, J. L. Germline stem cells and follicular renewal in the postnatal mammalian ovary. *Nature* 428, 145-150 (2004).
12. Johnson, J. et al. Oocyte generation in adult mammalian ovaries by putative germ cells in bone marrow and peripheral blood. *Cell* 122, 303-315 (2005).
13. Wood, S. A., Allen, N. D., Rossant, J., Auerbach, A. & Nagy. A. Non-injection methods for the production of embryonic stem cell-embryo chimeras. *Nature* 365, 87-89 (1993).
14. Seabright, M. A rapid banding technique for human chromosomes. *Lancet* 2, 971-972 (1971).

What is claimed is:

1. A method for preparing an embryonic stem cell (ESC)-like cell, which comprises the steps of:

(a) providing a first cell population obtained from F1 hybrid B6D2F1 mouse ovarian tissue, wherein the first cell population comprises adult stem cells;

(b) providing a second cell population which is embryonic fibroblast layer originated from an outbred ICR mouse fetus, wherein the second cell population is treated with mitomycin;

(c) culturing the first cell population on the second cell population in a medium for a period of time sufficient to form a colony from the first cell population, wherein the culturing is carried out in the presence of at least 5,000 units/ml of leukemia inhibitory factor; and (d) subculturing a cell from the colony in a medium for a period of time sufficient to prepare the ESC-like cell, wherein the subculturing is carried out in the presence of 800-1,200 units/ml of leukemia inhibitory factor to obtain said ESC-like cells.

2. The method according to claim 1, wherein the first cell population is a heterogeneous population comprising at least two kinds of cells.

3. The method according to claim 1, wherein the second cell population has adherent characteristics to culture plates.

4. The method according to claim 1, wherein the ESC-like cell has a diploid karyotype.

* * * * *

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: b-actin(RT) sense primer

<400> SEQUENCE: 1

accgtgaaaa gatgacccag                                                   20


<210> SEQ ID NO 2
<211> LENGTH: 20
<212> TYPE: DNA
```

-continued

```
<213> ORGANISM: Artificial Sequence
<220> FEATURE:
<223> OTHER INFORMATION: b-actin(RT) anti-sense primer

<400> SEQUENCE: 2

tctcagctgt ggtggtgaag                                                  20


<210> SEQ ID NO 3
<211> LENGTH: 20
<212> TYPE: DNA
<213> ORGANISM: Artificial Sequence
<220> FEATURE:
<223> OTHER INFORMATION: b-actin(R-T) sense primer

<400> SEQUENCE: 3

taccacaggc attgtgatgg                                                  20


<210> SEQ ID NO 4
<211> LENGTH: 21
<212> TYPE: DNA
<213> ORGANISM: Artificial Sequence
<220> FEATURE:
<223> OTHER INFORMATION: b-actin(R-T) anti-sense primer

<400> SEQUENCE: 4

tctttgatgt cacgcacgat t                                                21


<210> SEQ ID NO 5
<211> LENGTH: 20
<212> TYPE: DNA
<213> ORGANISM: Artificial Sequence
<220> FEATURE:
<223> OTHER INFORMATION: Oct-4(RT, R-T) sense primer

<400> SEQUENCE: 5

gaagccctcc ctacagcaga                                                  20


<210> SEQ ID NO 6
<211> LENGTH: 20
<212> TYPE: DNA
<213> ORGANISM: Artificial Sequence
<220> FEATURE:
<223> OTHER INFORMATION: Oct-4(RT, R-T) anti-sense primer

<400> SEQUENCE: 6

cagagcagtg acgggaacag                                                  20


<210> SEQ ID NO 7
<211> LENGTH: 20
<212> TYPE: DNA
<213> ORGANISM: Artificial Sequence
<220> FEATURE:
<223> OTHER INFORMATION: Nanog(RT, R-T) sense primer

<400> SEQUENCE: 7

ccccacaagc cttggaatta                                                  20


<210> SEQ ID NO 8
<211> LENGTH: 20
<212> TYPE: DNA
<213> ORGANISM: Artificial Sequence
<220> FEATURE:
<223> OTHER INFORMATION: Nanog(RT, R-T) anti-sense primer

<400> SEQUENCE: 8

ctcaaatccc agcaaccaca                                                  20
```

-continued

<210> SEQ ID NO 9
<211> LENGTH: 20
<212> TYPE: DNA
<213> ORGANISM: Artificial Sequence
<220> FEATURE:
<223> OTHER INFORMATION: Rex-1(RT) sense primer

<400> SEQUENCE: 9
acatcctaac ccacgcaaag 20

<210> SEQ ID NO 10
<211> LENGTH: 20
<212> TYPE: DNA
<213> ORGANISM: Artificial Sequence
<220> FEATURE:
<223> OTHER INFORMATION: Rex-1(RT) anti-sense primer

<400> SEQUENCE: 10
tgattttctg ccgtatgcaa 20

<210> SEQ ID NO 11
<211> LENGTH: 20
<212> TYPE: DNA
<213> ORGANISM: Artificial Sequence
<220> FEATURE:
<223> OTHER INFORMATION: Rex-1(R-T) sense primer

<400> SEQUENCE: 11
tccccgtgta acatacacca 20

<210> SEQ ID NO 12
<211> LENGTH: 20
<212> TYPE: DNA
<213> ORGANISM: Artificial Sequence
<220> FEATURE:
<223> OTHER INFORMATION: Rex-1(R-T) anti-sense primer

<400> SEQUENCE: 12
cttcgtcccc tttgtcatgt 20

<210> SEQ ID NO 13
<211> LENGTH: 20
<212> TYPE: DNA
<213> ORGANISM: Artificial Sequence
<220> FEATURE:
<223> OTHER INFORMATION: Cripto(RT) sense primer

<400> SEQUENCE: 13
ctttaagcag ggaggtggtg 20

<210> SEQ ID NO 14
<211> LENGTH: 20
<212> TYPE: DNA
<213> ORGANISM: Artificial Sequence
<220> FEATURE:
<223> OTHER INFORMATION: Cripto(RT) anti-sense primer

<400> SEQUENCE: 14
taaagccatc tgccacaatg 20

<210> SEQ ID NO 15
<211> LENGTH: 20
<212> TYPE: DNA
<213> ORGANISM: Artificial Sequence
<220> FEATURE:

-continued

<223> OTHER INFORMATION: Cripto(R-T) sense primer

<400> SEQUENCE: 15
cggagatctt ggctgctaac 20

<210> SEQ ID NO 16
<211> LENGTH: 20
<212> TYPE: DNA
<213> ORGANISM: Artificial Sequence
<220> FEATURE:
<223> OTHER INFORMATION: Cripto(R-T) anti-sense primer

<400> SEQUENCE: 16
cttcgacggc tcgtaaaaac 20

<210> SEQ ID NO 17
<211> LENGTH: 20
<212> TYPE: DNA
<213> ORGANISM: Artificial Sequence
<220> FEATURE:
<223> OTHER INFORMATION: Dnmt3b(RT) sense primer

<400> SEQUENCE: 17
agtccatcgc tgtgggaact 20

<210> SEQ ID NO 18
<211> LENGTH: 20
<212> TYPE: DNA
<213> ORGANISM: Artificial Sequence
<220> FEATURE:
<223> OTHER INFORMATION: Dnmt3b(RT) anti-sense primer

<400> SEQUENCE: 18
gggcgggtat aattcagcaa 20

<210> SEQ ID NO 19
<211> LENGTH: 20
<212> TYPE: DNA
<213> ORGANISM: Artificial Sequence
<220> FEATURE:
<223> OTHER INFORMATION: Dnmt3b(R-T) sense primer

<400> SEQUENCE: 19
gtccggaaaa tcaccaagaa 20

<210> SEQ ID NO 20
<211> LENGTH: 20
<212> TYPE: DNA
<213> ORGANISM: Artificial Sequence
<220> FEATURE:
<223> OTHER INFORMATION: Dnmt3b(R-T) anti-sense primer

<400> SEQUENCE: 20
ccagaagaat ggacggttgt 20

<210> SEQ ID NO 21
<211> LENGTH: 20
<212> TYPE: DNA
<213> ORGANISM: Artificial Sequence
<220> FEATURE:
<223> OTHER INFORMATION: Tert(RT) sense primer

<400> SEQUENCE: 21
ggatcctggc tacgttcctg 20

<210> SEQ ID NO 22
<211> LENGTH: 20
<212> TYPE: DNA
<213> ORGANISM: Artificial Sequence
<220> FEATURE:
<223> OTHER INFORMATION: Tert(RT) anti-sense primer

<400> SEQUENCE: 22
tgcctgacct cctcttgtga 20

<210> SEQ ID NO 23
<211> LENGTH: 20
<212> TYPE: DNA
<213> ORGANISM: Artificial Sequence
<220> FEATURE:
<223> OTHER INFORMATION: Tert(R-T) sense primer

<400> SEQUENCE: 23
gcagtggtcc ggagagatag 20

<210> SEQ ID NO 24
<211> LENGTH: 20
<212> TYPE: DNA
<213> ORGANISM: Artificial Sequence
<220> FEATURE:
<223> OTHER INFORMATION: Tert(R-T) anti-sense primer

<400> SEQUENCE: 24
acactgtgac gcaggaagtg 20

<210> SEQ ID NO 25
<211> LENGTH: 20
<212> TYPE: DNA
<213> ORGANISM: Artificial Sequence
<220> FEATURE:
<223> OTHER INFORMATION: Lif Rc(RT, R-T) sense primer

<400> SEQUENCE: 25
gctgagtggt aaagataccg 20

<210> SEQ ID NO 26
<211> LENGTH: 20
<212> TYPE: DNA
<213> ORGANISM: Artificial Sequence
<220> FEATURE:
<223> OTHER INFORMATION: Lif Rc(RT, R-T) anti-sense primer

<400> SEQUENCE: 26
ttcgttggac tcatacaaca 20

<210> SEQ ID NO 27
<211> LENGTH: 20
<212> TYPE: DNA
<213> ORGANISM: Artificial Sequence
<220> FEATURE:
<223> OTHER INFORMATION: Stat3(RT) sense primer

<400> SEQUENCE: 27
tttggaatga agggtacatc 20

<210> SEQ ID NO 28
<211> LENGTH: 20
<212> TYPE: DNA
<213> ORGANISM: Artificial Sequence
<220> FEATURE:
<223> OTHER INFORMATION: Stat3(RT) anti-sense primer

<400> SEQUENCE: 28
caaatgacat gttgttcagc 20

<210> SEQ ID NO 29
<211> LENGTH: 20
<212> TYPE: DNA
<213> ORGANISM: Artificial Sequence
<220> FEATURE:
<223> OTHER INFORMATION: Bmp4(RT) sense primer

<400> SEQUENCE: 29
tgagagaccc cagcctaaga 20

<210> SEQ ID NO 30
<211> LENGTH: 20
<212> TYPE: DNA
<213> ORGANISM: Artificial Sequence
<220> FEATURE:
<223> OTHER INFORMATION: Bmp4(RT) anti-sense primer

<400> SEQUENCE: 30
aaacttgctg gaaaggctca 20

<210> SEQ ID NO 31
<211> LENGTH: 20
<212> TYPE: DNA
<213> ORGANISM: Artificial Sequence
<220> FEATURE:
<223> OTHER INFORMATION: Fgf4(RT) sense primer

<400> SEQUENCE: 31
cagtcttctg gagctctctc 20

<210> SEQ ID NO 32
<211> LENGTH: 20
<212> TYPE: DNA
<213> ORGANISM: Artificial Sequence
<220> FEATURE:
<223> OTHER INFORMATION: Fgf4(RT) anti-sense primer

<400> SEQUENCE: 32
aggaagtggg ttaccttcat 20

<210> SEQ ID NO 33
<211> LENGTH: 19
<212> TYPE: DNA
<213> ORGANISM: Artificial Sequence
<220> FEATURE:
<223> OTHER INFORMATION: Foxd3(RT) sense primer

<400> SEQUENCE: 33
caagaacagc ctggtgaag 19

<210> SEQ ID NO 34
<211> LENGTH: 19
<212> TYPE: DNA
<213> ORGANISM: Artificial Sequence
<220> FEATURE:
<223> OTHER INFORMATION: Foxd3(RT) anti-sense primer

<400> SEQUENCE: 34
gtccagggtc cagtagttg 19

<210> SEQ ID NO 35
<211> LENGTH: 20

```
<212> TYPE: DNA
<213> ORGANISM: Artificial Sequence
<220> FEATURE:
<223> OTHER INFORMATION: Sox2(RT) sense primer

<400> SEQUENCE: 35

acgctcatga agaaggataa                                              20


<210> SEQ ID NO 36
<211> LENGTH: 20
<212> TYPE: DNA
<213> ORGANISM: Artificial Sequence
<220> FEATURE:
<223> OTHER INFORMATION: Sox2(RT) anti-sense primer

<400> SEQUENCE: 36

gtaggacatg ctgtaggtgg                                              20


<210> SEQ ID NO 37
<211> LENGTH: 20
<212> TYPE: DNA
<213> ORGANISM: Artificial Sequence
<220> FEATURE:
<223> OTHER INFORMATION: CD9(RT) sense primer

<400> SEQUENCE: 37

atgctaccac tgtttccaac                                              20


<210> SEQ ID NO 38
<211> LENGTH: 20
<212> TYPE: DNA
<213> ORGANISM: Artificial Sequence
<220> FEATURE:
<223> OTHER INFORMATION: CD9(RT) anti-sense primer

<400> SEQUENCE: 38

acaagttaaa ctggcagcat                                              20


<210> SEQ ID NO 39
<211> LENGTH: 20
<212> TYPE: DNA
<213> ORGANISM: Artificial Sequence
<220> FEATURE:
<223> OTHER INFORMATION: Gdf3(RT) sense primer

<400> SEQUENCE: 39

cgagtttcaa gactctgacc                                              20


<210> SEQ ID NO 40
<211> LENGTH: 20
<212> TYPE: DNA
<213> ORGANISM: Artificial Sequence
<220> FEATURE:
<223> OTHER INFORMATION: Gdf3(RT) anti-sense primer

<400> SEQUENCE: 40

tagaggacct tctggagaca                                              20


<210> SEQ ID NO 41
<211> LENGTH: 25
<212> TYPE: DNA
<213> ORGANISM: Artificial Sequence
<220> FEATURE:
<223> OTHER INFORMATION: Zfy1(gDNA) sense primer

<400> SEQUENCE: 41
```

-continued

```
gttactcatt ttcaggtgtt ctggg                                              25


<210> SEQ ID NO 42
<211> LENGTH: 25
<212> TYPE: DNA
<213> ORGANISM: Artificial Sequence
<220> FEATURE:
<223> OTHER INFORMATION: Zfy1(gDNA) anti-sense primer

<400> SEQUENCE: 42

gtgtcagctg ttataggatc agtga                                              25


<210> SEQ ID NO 43
<211> LENGTH: 20
<212> TYPE: DNA
<213> ORGANISM: Artificial Sequence
<220> FEATURE:
<223> OTHER INFORMATION: Xist(gDNA) sense primer

<400> SEQUENCE: 43

gagatacatt tatttgctca                                                    20


<210> SEQ ID NO 44
<211> LENGTH: 20
<212> TYPE: DNA
<213> ORGANISM: Artificial Sequence
<220> FEATURE:
<223> OTHER INFORMATION: Xist(gDNA) anti-sense primer

<400> SEQUENCE: 44

gacttagttt ggtttcttta                                                    20
```